(12) United States Patent
van der Weide et al.

(10) Patent No.: US 11,490,960 B2
(45) Date of Patent: *Nov. 8, 2022

(54) ENERGY DELIVERY SYSTEMS AND USES THEREOF

(71) Applicant: NEUWAVE MEDICAL, INC., Madison, WI (US)

(72) Inventors: Daniel Warren van der Weide, Madison, WI (US); Fred T. Lee, Jr., Madison, WI (US); Christopher Lee Brace, Madison, WI (US); Richard W. Schefelker, Madison, WI (US); Laura G. King, Brookfield, WI (US); Mark Thom, Madison, WI (US); Matthew Thiel, Verona, WI (US)

(73) Assignee: NEUWAVE MEDICAL, INC., Madison, WI (US)

( * ) Notice: Subject to any disclaimer, the term of this patent is extended or adjusted under 35 U.S.C. 154(b) by 357 days.

This patent is subject to a terminal disclaimer.

(21) Appl. No.: 16/796,610

(22) Filed: Feb. 20, 2020

(65) Prior Publication Data
US 2020/0197090 A1 Jun. 25, 2020

Related U.S. Application Data

(60) Division of application No. 15/845,785, filed on Dec. 18, 2017, now Pat. No. 10,603,106, which is a
(Continued)

(51) Int. Cl.
*A61B 18/18* (2006.01)
*A61B 17/32* (2006.01)
(Continued)

(52) U.S. Cl.
CPC .. *A61B 18/1815* (2013.01); *A61B 17/320068* (2013.01); *A61M 25/0021* (2013.01);
(Continued)

(58) Field of Classification Search
CPC ........ A61B 17/320068; A61B 18/1815; A61B 2018/00791; A61B 2018/183; A61M 25/0021; A61M 25/0105
See application file for complete search history.

(56) References Cited

U.S. PATENT DOCUMENTS

| 3,800,552 A | 4/1974 | Sollami |
| 3,838,242 A | 9/1974 | Goucher |

(Continued)

FOREIGN PATENT DOCUMENTS

| AU | 2015/202149 | 5/2015 |
| CN | 2579361 | 10/2003 |

(Continued)

OTHER PUBLICATIONS

Brace, C. et al. 'Analysis and experimental validation of triaxial antenna for microwave tumor ablation' IEEE MTTS Int Microw Symp Jun. 3, 2004 (6-11) 1437-1440.

(Continued)

*Primary Examiner* — Christopher A Flory
(74) *Attorney, Agent, or Firm* — Casimir Jones, SC; Robert A. Goetz

(57) ABSTRACT

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for delivering energy to difficult to access tissue regions (e.g. peripheral lung tissues), and/or reducing the amount of undesired heat given off during energy delivery.

15 Claims, 34 Drawing Sheets

Related U.S. Application Data continuation of application No. 14/867,986, filed on Sep. 28, 2015, now Pat. No. 9,872,729, which is a continuation of application No. 13/696,001, filed as application No. PCT/US2011/035000 on May 3, 2011, now Pat. No. 9,861,440.

(60) Provisional application No. 61/330,800, filed on May 3, 2010.

(51) Int. Cl.
| | |
|---|---|
| A61M 25/00 | (2006.01) |
| A61M 25/01 | (2006.01) |
| A61B 18/00 | (2006.01) |
| A61B 1/005 | (2006.01) |
| A61B 18/14 | (2006.01) |
| A61B 90/00 | (2016.01) |
| A61B 34/20 | (2016.01) |
| A61M 25/06 | (2006.01) |
| A61B 18/02 | (2006.01) |

(52) U.S. Cl.
CPC ....... *A61M 25/0105* (2013.01); *A61B 1/0051* (2013.01); *A61B 18/1487* (2013.01); *A61B 2017/32007* (2017.08); *A61B 2017/320069* (2017.08); *A61B 2018/00023* (2013.01); *A61B 2018/00071* (2013.01); *A61B 2018/00279* (2013.01); *A61B 2018/00285* (2013.01); *A61B 2018/00541* (2013.01); *A61B 2018/00577* (2013.01); *A61B 2018/00744* (2013.01); *A61B 2018/00791* (2013.01); *A61B 2018/00875* (2013.01); *A61B 2018/0212* (2013.01); *A61B 2018/183* (2013.01); *A61B 2018/1861* (2013.01); *A61B 2018/1892* (2013.01); *A61B 2034/2059* (2016.02); *A61B 2090/374* (2016.02); *A61B 2090/3762* (2016.02); *A61M 25/0133* (2013.01); *A61M 25/0136* (2013.01); *A61M 25/0147* (2013.01); *A61M 2025/0004* (2013.01); *A61M 2025/0681* (2013.01)

(56) References Cited

U.S. PATENT DOCUMENTS

| | | |
|---|---|---|
| 3,991,770 A | 11/1976 | LeVeen |
| 4,057,064 A | 11/1977 | Morrison |
| 4,074,718 A | 2/1978 | Morrison |
| 4,312,364 A | 1/1982 | Convert |
| 4,375,220 A | 3/1983 | Matvias |
| 4,446,874 A | 5/1984 | Vaguine |
| 4,494,539 A | 1/1985 | Zenitani |
| 4,534,347 A | 8/1985 | Taylor |
| 4,557,272 A | 12/1985 | Carr et al. |
| 4,586,491 A | 5/1986 | Carpenter |
| 4,589,424 A | 5/1986 | Vaguine |
| 4,601,296 A | 7/1986 | Yerushalmi |
| 4,621,642 A | 11/1986 | Chen |
| 4,627,435 A | 12/1986 | Hoskin |
| 4,641,649 A | 2/1987 | Walinsky |
| 4,643,186 A | 2/1987 | Rosen |
| 4,662,383 A | 5/1987 | Sogawa |
| 4,700,716 A | 10/1987 | Kasevich |
| 4,712,559 A | 12/1987 | Turner |
| 4,776,086 A | 10/1988 | Kasevich |
| 4,790,311 A | 12/1988 | Ruiz |
| 4,800,899 A | 1/1989 | Turner |
| 4,860,752 A | 8/1989 | Turner |
| 4,880,015 A | 11/1989 | Nierman |
| 4,901,719 A | 2/1990 | Trenconsky |
| 4,945,912 A | 8/1990 | Langberg |
| 4,974,587 A | 12/1990 | Turner et al. |
| 5,007,437 A | 4/1991 | Sterzer |
| 5,026,959 A | 6/1991 | Ito |
| 5,057,104 A | 10/1991 | Chess |
| 5,057,106 A | 10/1991 | Kasevich |
| 5,074,861 A | 12/1991 | Schneider |
| RE33,791 E | 1/1992 | Carr |
| 5,098,429 A | 3/1992 | Sterzer |
| 5,129,396 A | 7/1992 | Rosen |
| 5,150,717 A | 9/1992 | Rosen |
| 5,167,619 A | 12/1992 | Wuchinich |
| 5,211,625 A | 5/1993 | Sakurai |
| 5,213,561 A | 5/1993 | Weinstein et al. |
| 5,246,438 A | 9/1993 | Langberg |
| 5,248,312 A | 9/1993 | Langberg |
| 5,275,597 A | 1/1994 | Higgins |
| 5,277,201 A | 1/1994 | Stern |
| 5,281,213 A | 1/1994 | Milder |
| 5,281,217 A | 1/1994 | Edwards |
| 5,295,955 A | 3/1994 | Rosen |
| 5,300,099 A | 4/1994 | Rudie |
| 5,301,687 A | 4/1994 | Wong |
| 5,314,466 A | 5/1994 | Stern |
| 5,344,418 A | 9/1994 | Ghaffari |
| 5,344,435 A | 9/1994 | Turner |
| 5,348,554 A | 9/1994 | Imran |
| 5,358,515 A | 10/1994 | Hurter |
| 5,364,392 A | 11/1994 | Warner |
| 5,366,490 A | 11/1994 | Edwards |
| 5,369,251 A | 11/1994 | King |
| 5,370,678 A | 12/1994 | Edwards |
| 5,405,346 A | 4/1995 | Grundy |
| 5,431,649 A | 7/1995 | Mulier |
| 5,433,740 A | 7/1995 | Yamaguchi |
| 5,456,684 A | 10/1995 | Schmidt |
| 5,462,556 A | 10/1995 | Powers |
| 5,472,423 A | 12/1995 | Gronauer |
| 5,480,417 A | 1/1996 | Hascoet |
| 5,489,256 A | 2/1996 | Adair |
| 5,507,743 A | 4/1996 | Edwards |
| 5,531,677 A | 7/1996 | Lundquist |
| 5,540,649 A | 7/1996 | Bonnell et al. |
| 5,559,295 A | 9/1996 | Sheryll |
| 5,575,794 A | 11/1996 | Walus |
| 5,578,029 A | 11/1996 | Trelles |
| 5,597,146 A | 1/1997 | Putman |
| 5,591,227 A | 2/1997 | Dinh |
| 5,599,295 A | 2/1997 | Rosen |
| 5,599,352 A | 2/1997 | Dinh |
| 5,603,697 A | 2/1997 | Grundy |
| 5,620,479 A | 4/1997 | Diederich |
| 5,643,175 A | 7/1997 | Adair |
| 5,647,871 A | 7/1997 | Levine |
| 5,688,267 A | 11/1997 | Panescu |
| 5,693,082 A | 12/1997 | Warner |
| 5,697,949 A | 12/1997 | Giurtino |
| 5,716,389 A | 2/1998 | Walinsky |
| 5,737,384 A | 4/1998 | Fenn |
| 5,741,249 A | 4/1998 | Moss |
| 5,755,752 A | 5/1998 | Segal |
| 5,755,754 A | 5/1998 | Rudie |
| 5,759,200 A | 6/1998 | Azar |
| 5,776,129 A | 7/1998 | Mersch |
| 5,776,176 A | 7/1998 | Rudie |
| 5,782,827 A | 7/1998 | Gough |
| 5,788,692 A | 8/1998 | Campbell |
| 5,788,694 A | 8/1998 | Vancaillie |
| 5,800,494 A | 9/1998 | Campbell |
| 5,810,803 A | 9/1998 | Moss |
| 5,810,804 A | 9/1998 | Gough |
| 5,849,029 A | 12/1998 | Eckhouse |
| 5,902,251 A | 5/1999 | Vanhooydonk |
| 5,904,709 A | 5/1999 | Arndt et al. |
| 5,921,935 A | 7/1999 | Hickey |
| 5,957,969 A | 9/1999 | Warner |
| 5,963,082 A | 10/1999 | Dick |
| 5,995,875 A | 11/1999 | Blewett |
| 6,002,968 A | 12/1999 | Edwards |
| 6,012,457 A | 1/2000 | Lesh |
| 6,016,811 A | 1/2000 | Knopp |
| 6,026,331 A | 2/2000 | Feldberg |

(56) References Cited

U.S. PATENT DOCUMENTS

| | | |
|---|---|---|
| 6,044,846 A | 4/2000 | Edwards |
| 6,056,744 A | 5/2000 | Edwards |
| 6,067,475 A | 5/2000 | Graves |
| 6,073,052 A | 6/2000 | Zelickson |
| 6,083,255 A | 7/2000 | Laufer |
| 6,086,529 A | 7/2000 | Arndt |
| 6,091,995 A | 7/2000 | Ingle et al. |
| 6,097,985 A | 8/2000 | Kasevich |
| 6,102,885 A | 8/2000 | Bass |
| 6,104,959 A | 8/2000 | Spertell |
| 6,106,524 A | 8/2000 | Eggers |
| 6,120,496 A | 9/2000 | Whayne |
| 6,165,163 A | 12/2000 | Chien et al. |
| 6,174,307 B1 | 1/2001 | Daniel et al. |
| 6,182,666 B1 | 2/2001 | Dobak, III |
| 6,188,930 B1 | 2/2001 | Carson |
| 6,190,382 B1 | 2/2001 | Ormsby |
| 6,208,903 B1 | 3/2001 | Richards |
| 6,210,323 B1 | 4/2001 | Gilhuly et al. |
| 6,223,085 B1 | 4/2001 | Dann |
| 6,230,060 B1 | 5/2001 | Mawhinney |
| 6,235,022 B1 | 5/2001 | Hallock |
| 6,241,725 B1 | 6/2001 | Cosman |
| 6,245,062 B1 | 6/2001 | Berube |
| 6,246,784 B1 | 6/2001 | Summers |
| 6,246,905 B1 | 6/2001 | Mogul |
| 6,251,128 B1 | 6/2001 | Knopp |
| 6,254,598 B1 | 7/2001 | Edwards |
| 6,273,884 B1 | 8/2001 | Altshuler |
| 6,273,885 B1 | 8/2001 | Koop |
| 6,273,886 B1 | 8/2001 | Edwards |
| 6,277,113 B1 | 8/2001 | Berube |
| 6,287,302 B1 | 9/2001 | Berube |
| 6,306,130 B1 | 10/2001 | Anderson |
| 6,306,132 B1 | 10/2001 | Moorman |
| 6,312,427 B1 | 11/2001 | Berube |
| 6,325,796 B1 | 12/2001 | Berube |
| 6,347,251 B1 | 2/2002 | Deng |
| 6,355,033 B1 | 3/2002 | Moorman |
| 6,364,876 B1 | 4/2002 | Erb |
| 6,383,182 B1 | 5/2002 | Berube |
| 6,395,803 B1 | 5/2002 | Angeletakis |
| 6,398,781 B1 | 6/2002 | Goble |
| 6,402,742 B1 | 6/2002 | Blewett |
| 6,427,089 B1 | 7/2002 | Knowlton |
| 6,435,872 B1 | 8/2002 | Nagel |
| 6,461,351 B1 | 10/2002 | Woodruff et al. |
| 6,461,352 B2 | 10/2002 | Morgan |
| 6,471,696 B1 | 10/2002 | Berube |
| 6,500,174 B1 | 12/2002 | Maguire |
| 6,506,189 B1 | 1/2003 | Rittman |
| 6,514,249 B1 | 2/2003 | Maguire |
| 6,524,308 B1 | 2/2003 | Muller |
| 6,527,768 B2 | 3/2003 | Berube |
| 6,530,922 B2 | 3/2003 | Cosman |
| 6,546,077 B2 | 4/2003 | Chornenky |
| 6,575,969 B1 | 6/2003 | Rittman, III et al. |
| 6,577,903 B1 | 6/2003 | Cronin |
| 6,582,426 B2 | 6/2003 | Moorman et al. |
| 6,582,486 B1 | 6/2003 | Delpiano |
| 6,585,733 B2 | 7/2003 | Wellman |
| 6,593,395 B2 | 7/2003 | Angeletakis |
| 6,602,074 B1 | 8/2003 | Suh |
| 6,622,731 B2 | 9/2003 | Daniel |
| 6,635,055 B1 | 10/2003 | Cronin |
| 6,638,277 B2 | 10/2003 | Schaefer et al. |
| 6,652,520 B2 | 11/2003 | Moorman |
| 6,663,625 B1 | 12/2003 | Ormsby |
| 6,666,579 B2 | 12/2003 | Jensen |
| 6,673,068 B1 | 1/2004 | Berube |
| 6,683,625 B2 | 2/2004 | Vining |
| 6,694,163 B1 | 3/2004 | Francischelli |
| 6,699,240 B2 | 3/2004 | Delpiano |
| 6,702,576 B2 | 3/2004 | Fischer |
| 6,709,271 B2 | 3/2004 | Yin |
| 6,740,107 B2 | 5/2004 | Loeb |
| 6,749,606 B2 | 6/2004 | Keast |
| 6,752,767 B2 | 6/2004 | Turovskiy |
| D493,531 S | 7/2004 | Padain |
| 6,770,070 B1 | 8/2004 | Balbierz |
| 6,780,178 B2 | 8/2004 | Palanker |
| 6,802,840 B2 | 10/2004 | Chin |
| 6,817,976 B2 | 11/2004 | Rovegno |
| 6,817,999 B2 | 11/2004 | Berube |
| 6,823,218 B2 | 11/2004 | Berube |
| 6,837,712 B2 | 1/2005 | Qian |
| 6,847,848 B2 | 1/2005 | Sterzer |
| 6,849,075 B2 | 2/2005 | Bertolero |
| 6,852,091 B2 | 2/2005 | Edwards |
| 6,866,624 B2 | 3/2005 | Chornenky |
| 6,866,663 B2 | 3/2005 | Edwards |
| 6,869,431 B2 | 3/2005 | Maguire et al. |
| 6,878,147 B2 | 4/2005 | Prakash |
| D507,649 S | 5/2005 | Padain |
| 6,890,968 B2 | 5/2005 | Angeletakis |
| 6,893,436 B2 | 5/2005 | Woodard |
| 6,898,454 B2 | 5/2005 | Atalar |
| 6,918,905 B2 | 7/2005 | Neuberger |
| 6,924,325 B2 | 8/2005 | Qian |
| 6,957,108 B2 | 10/2005 | Turner |
| 6,962,586 B2 | 11/2005 | Berube |
| 6,972,016 B2 | 12/2005 | Hill |
| 6,976,986 B2 | 12/2005 | Berube |
| 6,994,546 B2 | 2/2006 | Fischer |
| 7,022,105 B1 | 4/2006 | Edwards |
| 7,033,352 B1 | 4/2006 | Gauthier |
| 7,097,641 B1 | 8/2006 | Arless |
| 7,101,369 B2 | 9/2006 | Van Der Welde |
| 7,115,126 B2 | 10/2006 | Berube |
| 7,128,739 B2 | 10/2006 | Prakash |
| 7,142,633 B2 | 11/2006 | Eberhard |
| 7,147,632 B2 | 12/2006 | Prakash |
| 7,153,298 B1 | 12/2006 | Cohen |
| 7,156,842 B2 | 1/2007 | Sartor |
| 7,160,289 B2 | 1/2007 | Cohen |
| 7,160,292 B2 | 1/2007 | Moorman |
| 7,182,762 B2 | 2/2007 | Bortkiewicz |
| 7,184,824 B2 | 2/2007 | Hashimshony |
| 7,197,363 B2 | 3/2007 | Prakash |
| 7,233,820 B2 | 6/2007 | Gilboa |
| 7,244,254 B2 | 7/2007 | Brace |
| 7,263,997 B2 | 9/2007 | Madsen et al. |
| 7,266,407 B2 | 9/2007 | Li et al. |
| 7,282,049 B2 | 10/2007 | Orszulak |
| 7,311,703 B2 | 12/2007 | Turovskiy |
| 7,318,824 B2 | 1/2008 | Prakash |
| 7,324,104 B1 | 1/2008 | Bitter |
| 7,331,960 B2 | 2/2008 | Schaer |
| 7,381,208 B2 | 2/2008 | Van der Walt |
| 7,400,929 B2 | 6/2008 | Zelickson et al. |
| 7,402,140 B2 | 7/2008 | Spero |
| 7,410,484 B2 | 7/2008 | Littrup |
| 7,467,015 B2 | 12/2008 | Van der Weide |
| 7,473,219 B1 | 1/2009 | Glenn |
| 7,527,623 B2 | 5/2009 | Prakash |
| 7,594,313 B2 | 9/2009 | Prakash |
| 7,601,149 B2 | 10/2009 | DiCarlo |
| 7,625,369 B2 | 12/2009 | Abboud |
| 7,722,620 B2 | 5/2010 | Truckai |
| 7,731,677 B2 | 6/2010 | Sakurai |
| 7,815,637 B2 | 10/2010 | Ormsby |
| 7,826,904 B2 | 11/2010 | Appling |
| 7,862,559 B2 | 1/2011 | Prakash |
| 7,875,024 B2 | 1/2011 | Turovskiy |
| 8,035,570 B2 | 1/2011 | Turovskiy |
| 8,059,059 B2 | 11/2011 | Bonn |
| 8,093,500 B2 | 1/2012 | Deborski |
| 8,109,895 B2 | 2/2012 | Williams et al. |
| 8,147,511 B2 | 4/2012 | Perry |
| 8,152,799 B2 | 4/2012 | Ormsby |
| 8,155,418 B2 | 4/2012 | Delso |
| 8,235,981 B2 | 8/2012 | Prakash |
| 8,292,881 B2 * | 10/2012 | Brannan .......... A61B 18/1815 606/33 |

(56) References Cited

U.S. PATENT DOCUMENTS

| | | |
|---|---|---|
| 8,357,148 B2 | 1/2013 | Boulais et al. |
| 8,403,924 B2 | 3/2013 | Behnke |
| 8,430,871 B2 | 4/2013 | Brannan |
| 8,454,589 B2 | 6/2013 | Deno |
| 8,515,554 B2 | 8/2013 | Carr |
| 8,523,854 B2 | 9/2013 | Willyard |
| 8,540,710 B2 | 9/2013 | Johnson |
| 8,574,227 B2 | 11/2013 | Hancock |
| 8,643,561 B2 | 2/2014 | Prakash |
| 8,653,828 B2 | 2/2014 | Hancock |
| 8,655,454 B2 | 2/2014 | Prakash |
| 8,672,932 B2 | 3/2014 | van der Weide |
| 8,747,398 B2 | 6/2014 | Behnke |
| 8,764,744 B2 | 7/2014 | Brannan |
| 8,932,281 B2 | 1/2015 | Brannan |
| 8,934,989 B2 | 1/2015 | Ormsby |
| 8,945,111 B2 | 2/2015 | Brannan |
| 8,968,290 B2 | 3/2015 | Brannan |
| 9,008,793 B1 | 4/2015 | Cosman |
| 9,011,421 B2 | 4/2015 | Brannan |
| 9,017,319 B2 | 4/2015 | Brannan |
| 9,041,616 B2 | 5/2015 | Prakash |
| 9,072,532 B2 | 7/2015 | Van Der Weide et al. |
| 9,113,926 B2 | 8/2015 | Brannan |
| 9,119,649 B2 | 9/2015 | van der Weide |
| 9,119,650 B2 | 9/2015 | Brannan |
| 9,161,811 B2 | 10/2015 | Cronin |
| 9,173,706 B2 | 11/2015 | Rossetto |
| 9,192,436 B2 | 11/2015 | Willyard |
| 9,192,438 B2 | 11/2015 | Thiel |
| 9,198,725 B2 | 12/2015 | Willyard |
| 9,220,441 B2 | 12/2015 | Yoo |
| 2001/0020166 A1 | 9/2001 | Daly et al. |
| 2001/0039416 A1 | 11/2001 | Moorman et al. |
| 2001/0049524 A1 | 12/2001 | Morgan et al. |
| 2002/0022836 A1 | 2/2002 | Goble |
| 2002/0026187 A1 | 2/2002 | Swanson et al. |
| 2002/0026188 A1 | 2/2002 | Balbierz et al. |
| 2002/0040185 A1 | 4/2002 | Atalar et al. |
| 2002/0072742 A1 | 6/2002 | Schaefer et al. |
| 2002/0087151 A1 | 7/2002 | Mody |
| 2002/0087157 A1 | 7/2002 | Sliwa, Jr. et al. |
| 2002/0173780 A1 | 11/2002 | Altshuler |
| 2002/0183740 A1 | 12/2002 | Edwards et al. |
| 2003/0032951 A1 | 2/2003 | Rittman et al. |
| 2003/0060813 A1 | 3/2003 | Loeb |
| 2003/0065317 A1 | 4/2003 | Rudie |
| 2003/0088242 A1 | 5/2003 | Prakash et al. |
| 2003/0120268 A1 | 6/2003 | Bertolero |
| 2003/0125720 A1 | 7/2003 | Woodard et al. |
| 2003/0130711 A1 | 7/2003 | Pearson et al. |
| 2004/0030367 A1 | 2/2004 | Yamaki et al. |
| 2004/0068208 A1 | 4/2004 | Cimino et al. |
| 2004/0082859 A1 | 4/2004 | Schaer |
| 2004/0116921 A1 | 6/2004 | Sherman |
| 2004/0133254 A1 | 8/2004 | Marwan |
| 2004/0158237 A1 | 8/2004 | Abboud et al. |
| 2004/0186517 A1 | 9/2004 | Hill et al. |
| 2004/0199154 A1 | 10/2004 | Nahon |
| 2004/0215131 A1 | 10/2004 | Sakurai et al. |
| 2004/0215294 A1 | 10/2004 | Littrup et al. |
| 2004/0243004 A1 | 12/2004 | Carr |
| 2004/0243200 A1 | 12/2004 | Turner et al. |
| 2004/0267248 A1 | 12/2004 | Duong |
| 2005/0011885 A1 | 1/2005 | Seghatol |
| 2005/0015081 A1 | 1/2005 | Turovskiy et al. |
| 2005/0075629 A1 | 4/2005 | Chapelon |
| 2005/0107870 A1 | 5/2005 | Wang |
| 2005/0109900 A1 | 5/2005 | Schilt et al. |
| 2005/0113824 A1 | 5/2005 | Sartor et al. |
| 2005/0143726 A1 | 5/2005 | Bortkiewicz |
| 2005/0149010 A1 | 7/2005 | Turovskiy |
| 2005/0165389 A1 | 7/2005 | Swain |
| 2005/0177209 A1 | 8/2005 | Leung et al. |
| 2005/0245919 A1 | 11/2005 | Van Der Welde |
| 2005/0245920 A1 | 11/2005 | Vitullo et al. |
| 2006/0064083 A1 | 3/2006 | Khalaj et al. |
| 2006/0079886 A1 | 4/2006 | Orszulak et al. |
| 2006/0094956 A1 | 5/2006 | Vismanathan |
| 2006/0106281 A1 | 5/2006 | Boulais et al. |
| 2006/0122625 A1 | 6/2006 | Truckai |
| 2006/0129140 A1 | 6/2006 | Todd et al. |
| 2006/0155270 A1 | 7/2006 | Hancock |
| 2006/0171506 A1 | 8/2006 | Lovoi et al. |
| 2006/0189973 A1 | 8/2006 | van der Weide |
| 2006/0200026 A1 | 9/2006 | Wallace et al. |
| 2006/0200120 A1 | 9/2006 | Dicarlo et al. |
| 2006/0224220 A1 | 10/2006 | Zelickson |
| 2006/0264921 A1 | 11/2006 | Deutsch |
| 2006/0276780 A1 | 12/2006 | Brace et al. |
| 2006/0289528 A1 | 12/2006 | Chiu et al. |
| 2007/0016180 A1 | 1/2007 | Lee, Jr. et al. |
| 2007/0021741 A1 | 1/2007 | Marwan et al. |
| 2007/0066972 A1 | 3/2007 | Ormsby |
| 2007/0185554 A1 | 8/2007 | Appling et al. |
| 2007/0203551 A1 | 8/2007 | Cronin |
| 2007/0208389 A1 | 9/2007 | Amundson et al. |
| 2007/0230757 A1 | 10/2007 | Trachtenberg |
| 2007/0270924 A1 | 11/2007 | McCann et al. |
| 2007/0276362 A1 | 11/2007 | Rioux |
| 2007/0282319 A1 | 12/2007 | van der Weide |
| 2007/0288079 A1 | 12/2007 | van der Weide |
| 2008/0033424 A1 | 2/2008 | Van Der Weide |
| 2008/0045938 A1 | 2/2008 | Weide et al. |
| 2008/0114345 A1 | 5/2008 | Arless et al. |
| 2008/0147056 A1 | 6/2008 | Van der Weide |
| 2008/0161890 A1 | 7/2008 | Lafontaine |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0195226 A1 | 8/2008 | Williams et al. |
| 2008/0221391 A1 | 9/2008 | Weitzner et al. |
| 2008/0243176 A1 | 10/2008 | Weitzner et al. |
| 2009/0005766 A1 | 1/2009 | Brannan |
| 2009/0054962 A1 | 2/2009 | Lefler |
| 2009/0076492 A1 | 3/2009 | Behnke |
| 2009/0118725 A1 | 5/2009 | Auth et al. |
| 2009/0187180 A1 | 7/2009 | Brannan |
| 2009/0187186 A1 | 7/2009 | Jakus |
| 2009/0196480 A1 | 8/2009 | Nields et al. |
| 2009/0222002 A1 | 9/2009 | Bonn et al. |
| 2009/0281536 A1 | 11/2009 | Beckman et al. |
| 2009/0306644 A1 | 12/2009 | Mayse |
| 2010/0023866 A1 | 1/2010 | Peck |
| 2010/0045558 A1 | 2/2010 | Rossetto |
| 2010/0045559 A1 | 2/2010 | Rossetto |
| 2010/0076424 A1 | 3/2010 | Carr |
| 2010/0081928 A1 | 4/2010 | Hyde et al. |
| 2010/0137796 A1 | 6/2010 | Perry et al. |
| 2010/0228244 A1 | 9/2010 | Hancock et al. |
| 2010/0268223 A1 | 10/2010 | Coe |
| 2010/0286791 A1 | 11/2010 | Goldsmith |
| 2010/0292766 A1 | 11/2010 | Duong |
| 2010/0305561 A1 | 12/2010 | Prakash et al. |
| 2010/0312095 A1 | 12/2010 | Jenkins |
| 2010/0312096 A1 | 12/2010 | Guttman |
| 2010/0317962 A1 | 12/2010 | Jenkins |
| 2011/0077635 A1 | 3/2011 | Bonn |
| 2011/0098696 A1 | 4/2011 | Brannan |
| 2011/0118723 A1 | 5/2011 | Turner et al. |
| 2011/0118725 A1 | 5/2011 | Mayse |
| 2011/0213352 A1 | 9/2011 | Lee et al. |
| 2011/0238060 A1 | 9/2011 | Lee, Jr. |
| 2011/0238061 A1 | 9/2011 | van der Weide |
| 2011/0257647 A1 | 10/2011 | Mayse |
| 2011/0301587 A1 | 12/2011 | Deem |
| 2012/0016358 A1 | 1/2012 | Mayse |
| 2012/0053577 A1 | 3/2012 | Lee et al. |
| 2012/0116286 A1 | 5/2012 | Williams et al. |
| 2012/0182134 A1 | 7/2012 | Doyle |
| 2012/0194409 A1 | 8/2012 | Brannan |
| 2012/0203216 A1 | 8/2012 | Mayse |
| 2012/0203222 A1 | 8/2012 | Mayse |

(56) References Cited

U.S. PATENT DOCUMENTS

| | | | |
|---|---|---|---|
| 2012/0209257 A1 | 8/2012 | Weide et al. | |
| 2012/0209261 A1 | 8/2012 | Mayse | |
| 2012/0209296 A1 | 8/2012 | Mayse | |
| 2012/0232544 A1 | 9/2012 | Willyard | |
| 2012/0232549 A1 | 9/2012 | Willyard | |
| 2012/0310228 A1 | 12/2012 | Bonn et al. | |
| 2012/0316551 A1 | 12/2012 | can der Weide | |
| 2012/0316552 A1 | 12/2012 | Mayse | |
| 2012/0316559 A1 | 12/2012 | Mayse | |
| 2013/0004037 A1 | 1/2013 | Scheuering | |
| 2013/0023866 A1 | 1/2013 | Stringham et al. | |
| 2013/0072924 A1 | 3/2013 | Burgener | |
| 2013/0116679 A1 | 5/2013 | van der Weide et al. | |
| 2013/0123598 A1 | 5/2013 | Jenkins | |
| 2013/0131496 A1 | 5/2013 | Jenkins | |
| 2013/0165915 A1 | 6/2013 | Thiel | |
| 2013/0259335 A1 | 10/2013 | Mallya et al. | |
| 2013/0306543 A1 | 11/2013 | Beisser | |
| 2013/0338530 A1 | 12/2013 | Kassab | |
| 2014/0005706 A1 | 1/2014 | Gelfand et al. | |
| 2014/0046176 A1 | 2/2014 | Ladtkow | |
| 2014/0152656 A1 | 6/2014 | Yoo | |
| 2014/0163664 A1 | 6/2014 | Goldsmith et al. | |
| 2014/0276033 A1 | 9/2014 | Brannan | |
| 2014/0276200 A1 | 9/2014 | Brannan | |
| 2014/0046174 A1 | 12/2014 | Ladtkow et al. | |
| 2015/0148792 A1 | 5/2015 | Kim | |
| 2015/0150628 A1 | 6/2015 | Buysse | |
| 2015/0164587 A1 | 6/2015 | Bonn et al. | |
| 2015/0190193 A1 | 7/2015 | Mayse | |
| 2015/0250540 A1 | 9/2015 | Behdad et al. | |
| 2015/0351839 A1 | 12/2015 | Brannan | |
| 2015/0374438 A1 | 12/2015 | van der weide | |

FOREIGN PATENT DOCUMENTS

| | | |
|---|---|---|
| CN | 1593353 | 3/2005 |
| CN | 1703168 | 11/2005 |
| CN | 2753408 | 1/2006 |
| CN | 201267529 | 7/2009 |
| CN | 101511295 | 8/2009 |
| CN | 101563042 | 10/2009 |
| CN | 101610735 A | 12/2009 |
| EP | 1186274 | 3/2002 |
| EP | 1265532 | 12/2002 |
| EP | 1395190 | 3/2004 |
| EP | 1450710 | 9/2004 |
| EP | 1499251 | 1/2005 |
| EP | 1542607 | 6/2005 |
| EP | 1659969 | 5/2006 |
| EP | 1723922 | 11/2006 |
| EP | 2098184 | 9/2009 |
| EP | 2295000 | 3/2011 |
| EP | 2316370 | 5/2011 |
| GB | 2388039 | 11/2003 |
| GB | 2406521 | 4/2005 |
| JP | 10-192286 | 7/1998 |
| JP | 2002-541884 | 12/2002 |
| JP | 2003-530139 | 10/2003 |
| JP | 2003-534037 | 11/2003 |
| JP | 2004-188179 | 7/2004 |
| JP | 2005-522274 | 7/2005 |
| JP | 2007-029457 | 2/2007 |
| JP | 2007-532024 | 11/2007 |
| JP | 2008-142467 | 6/2008 |
| JP | 2009-006150 | 1/2009 |
| JP | 2009-521264 | 6/2009 |
| JP | 2009-521967 | 6/2009 |
| JP | 2009-207898 | 9/2009 |
| JP | 2009-285463 | 12/2009 |
| JP | 2010-505573 | 2/2010 |
| JP | 2010-050975 | 3/2010 |
| JP | 2011-511538 | 4/2011 |
| JP | 2011-092720 | 5/2011 |
| JP | 2011-152414 | 8/2011 |
| WO | WO 1992/004934 | 4/1992 |
| WO | 93/02733 | 2/1993 |
| WO | WO 1993/009845 | 5/1993 |
| WO | WO 1995/004385 | 2/1995 |
| WO | WO 1997/048449 | 12/1997 |
| WO | WO 1999/056643 | 11/1999 |
| WO | WO 2000/057811 | 5/2000 |
| WO | WO 2001/070114 | 9/2001 |
| WO | WO 2003/039385 | 5/2003 |
| WO | WO 2003/086190 | 10/2003 |
| WO | WO 2003/086498 | 10/2003 |
| WO | WO 2003/088806 | 10/2003 |
| WO | WO 2003/088858 | 10/2003 |
| WO | WO 2004/004586 | 1/2004 |
| WO | WO 2004/026122 | 4/2004 |
| WO | WO 2004/033039 | 4/2004 |
| WO | WO 2004/084748 | 10/2004 |
| WO | WO 2004/112628 | 12/2004 |
| WO | WO 2005/011049 | 2/2005 |
| WO | WO 2005/034783 | 4/2005 |
| WO | WO 2005/110265 | 11/2005 |
| WO | WO 2006/002843 | 1/2006 |
| WO | WO 2006/002943 | 1/2006 |
| WO | WO 2006/004585 | 1/2006 |
| WO | WO 2006/005579 | 1/2006 |
| WO | WO 2006/008481 | 1/2006 |
| WO | WO 2006/084676 | 8/2006 |
| WO | WO 2006/127847 | 11/2006 |
| WO | WO 2007/076924 | 7/2007 |
| WO | WO 2007/112103 | 10/2007 |
| WO | WO 2006/122149 | 11/2007 |
| WO | WO 2008/008545 | 1/2008 |
| WO | WO 2008/044013 | 4/2008 |
| WO | WO 2008/142686 | 11/2008 |
| WO | 2010/048334 | 4/2010 |
| WO | 2010/048335 | 4/2010 |
| WO | WO 2010/067360 | 6/2010 |
| WO | WO 2011/008903 | 1/2011 |
| WO | WO 2011/017168 | 2/2011 |
| WO | WO 2011/140087 | 11/2011 |
| WO | WO 2013/173481 | 11/2013 |

OTHER PUBLICATIONS

Brace, C. et al. 'Microwave Ablation with Triaxial Antenna: Results in ex vivo Bovine Liver' IEEE Transactions on Microwave Theory and Techniques, vol. 53, No. 1 Jan. 2005.

English translation of Decision of Refusal from related Japanese Patent Application No. 2013-509179, dated Jun. 30, 2015.

Golio, 'The RF and microwave handbook' Edition 2 Published by CRC Press 2001 ISBN 0849338592X, 97808493859626.

Guy, Aw (1971) IEEE Trans. Microwave Theory Tech. 19 pp. 189-217.

Guy, Aw (1971) IEEE Trans. Microwave Theory Tech. 19 pp. 205-214.

Head, H.W. et al 'Thermal Ablation for Hepatocellular Carcinoma' Gastroenterology (2004) 127 pp. S167-S178.

Seki, T. et al. 'Ultrasonically Guided Percutaneous Microwave Coagulation Therapy for Small Hepatocellular Carcinoma' Cancer, Aug. 1, 1994, vol. 74, No. 3 pp. 817-825.

Carbon dioxide. Carbon dioxide—New World Encyclopedia. Web. <http://www.newworldencyclopedia.org/entry/Carbon_dioxide>.

European Search Report dated Mar. 3, 2009, EP Patent Application No. 06802385.2.

European Search Report dated Mar. 9, 2015, EP Patent Application No. 14189493.1.

Extended European Search Report re: 11778168 dated Sep. 24, 2013.

Notice Regarding Extended European Search Report re: 11778168 dated Oct. 2, 2013.

Extended European Search Report re: 17168163.8 dated Sep. 13, 2017.

International Preliminary Report on Patentability re: PCT/US2007/007408 dated Sep. 30, 2008.

International Preliminary Report on Patentability re: PCT/US2007/007464 dated Sep. 30, 2008.

(56) References Cited

OTHER PUBLICATIONS

International Preliminary Report on Patentability re: PCT/US2007/016082 dated Jan. 14, 2009.
International Preliminary Report on Patentability re: PCT/US2010/043558 dated Jan. 31, 2012.
International Preliminary Report on Patentability re: PCT/US2011/035000 dated Nov. 6, 2012.
International Preliminary Report on Patentability re: PCT/US2012/071310 dated Aug. 19, 2014.
International Preliminary Report on Patentability re: PCT/US2016/058888 dated Dec. 11, 2017.
International Preliminary Report on Patentability re: PCT/US2016/058890 dated May 1, 2018.
International Search Report PCT/US2005/014534 dated Nov. 29, 2005.
International Search Report PCT/US2006/017981 dated Sep. 7, 2006.
International Search Report PCT US/2006/028821 dated Mar. 21, 2007.
International Search Report PCT/US2006/031644 dated Aug. 17, 2007.
International Search Report PCT/US2006/033341 dated Aug. 17, 2007.
International Search Report PCT/US2006/032811 dated Jan. 25, 2007.
International Search Report re: PCT/US2007/007408 dated Aug. 31, 2007.
International Search Report on Patentability re: PCT/US2007/016082 dated Jul. 21, 2008.
International Search Report PCT/US2011/035000 dated Jan. 6, 2012.
International Search Report re: PCT/US2012/071310 dated Feb. 25, 2013.
International Search Report re: PCT/US2016/58888 dated Feb. 15, 2017.
International Search Report re: PCT/US2016/058890 dated Jan. 19, 2017.
International Search Report re: PCT/US2017/027424 dated Oct. 9, 2017.
Supplementary European Search Report re: EP07810483 dated Mar. 22, 2013.
Supplementary European Search Report re: EP10806929 dated Feb. 21, 2013.
Supplementary European Search Report re: EP11778168 dated Sep. 24, 2013.
Supplementary European Search Report re: EP12860249 dated Sep. 15, 2015.
U.S. Appl. No. 09/847,181, filed May 1, 2001.
U.S. Appl. No. 10/370,179, filed Feb. 19, 2003.
U.S. Appl. No. 10/834,802, filed Apr. 29, 2004.
U.S. Appl. No. 10/961,761, filed Oct. 7, 2004.
U.S. Appl. No. 10/961,994, filed Oct. 7, 2004.
U.S. Appl. No. 10/980,699, filed Nov. 3, 2004.
U.S. Appl. No. 11/053,987, filed Feb. 8, 2005.
U.S. Appl. No. 11/236,985, filed Sep. 28, 2005.
U.S. Appl. No. 11/237,136, filed Sep. 28, 2005.
U.S. Appl. No. 11/237,430, filed Sep. 28, 2005.
U.S. Appl. No. 11/440,331, filed May 24, 2006.
U.S. Appl. No. 11/452,637, filed Jun. 14, 2006.
U.S. Appl. No. 11/502,783, filed Aug. 11, 2006.
U.S. Appl. No. 11/514,628, filed Sep. 1, 2006.
U.S. Appl. No. 11/728,428, filed Mar. 26, 2007.
U.S. Appl. No. 11/728,457, filed Mar. 26, 2007.
U.S. Appl. No. 11/728,460, filed Mar. 26, 2007.
U.S. Appl. No. 60/679,722, filed May 10, 2005.
U.S. Appl. No. 60/785,466, filed Mar. 24, 2006.
U.S. Appl. No. 60/785,467, filed Mar. 24, 2006.
U.S. Appl. No. 60/785,690, filed Mar. 24, 2006.
U.S. Appl. No. 60/831,055, filed Jul. 14, 2006.
EP Search Report, EP Patent Application No. 20211854.3, dated Feb. 1, 2021, 3 pages.

* cited by examiner

FIG. 2
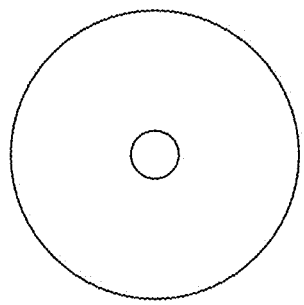 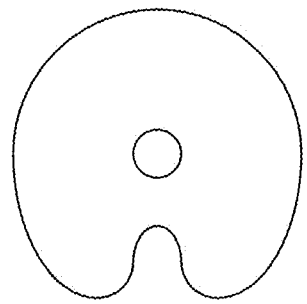 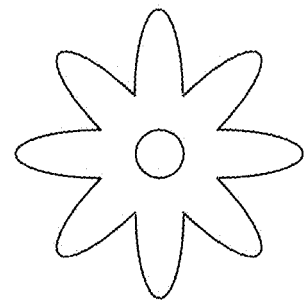
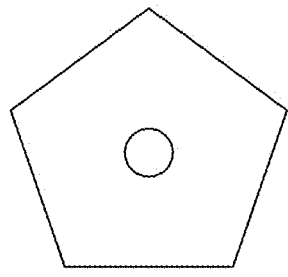 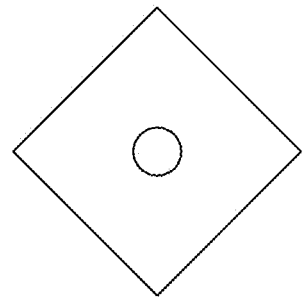 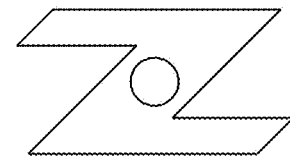
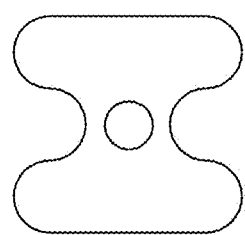  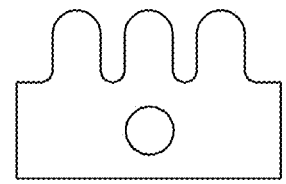

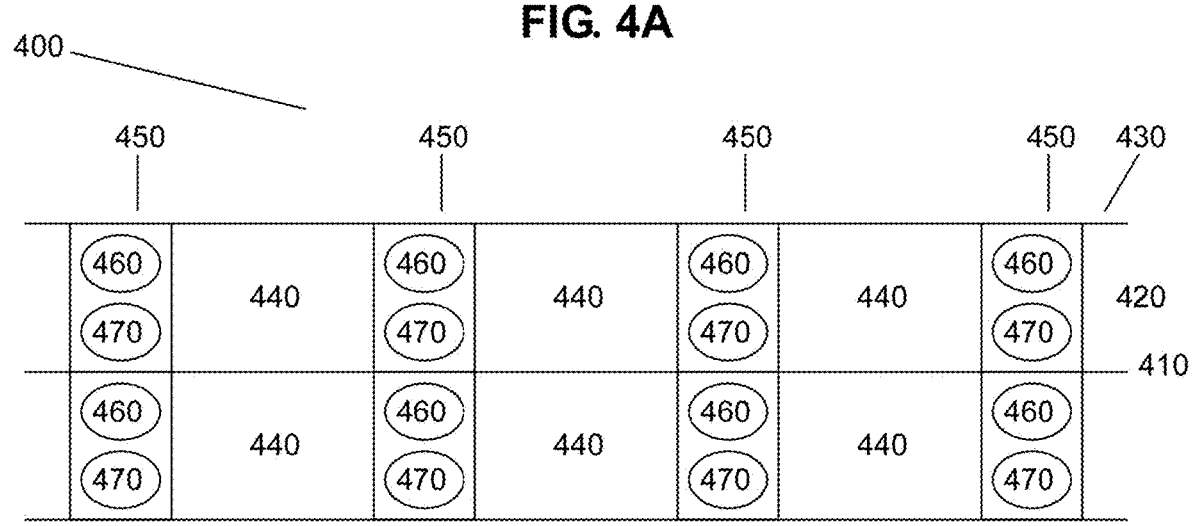
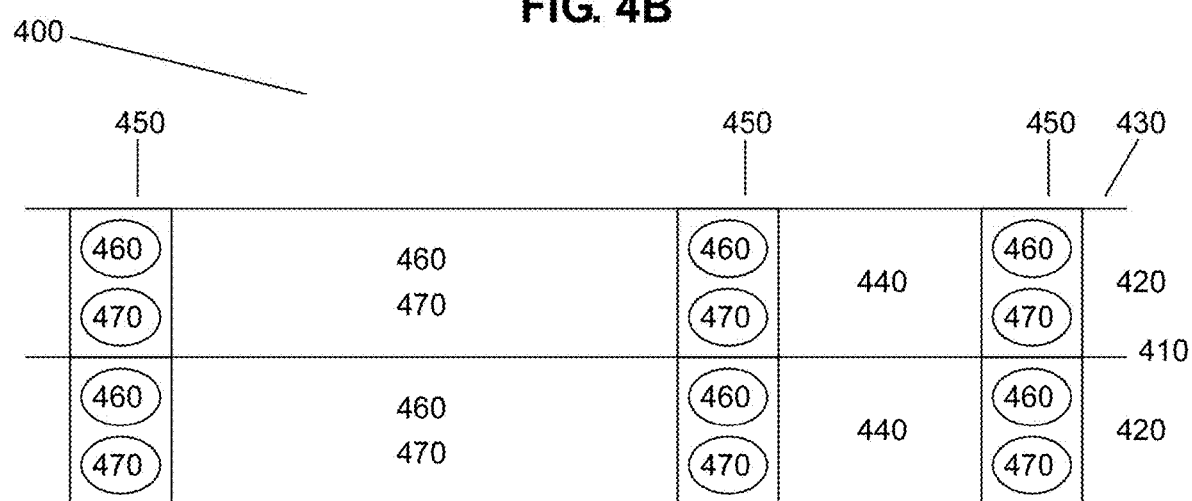

FIG. 6
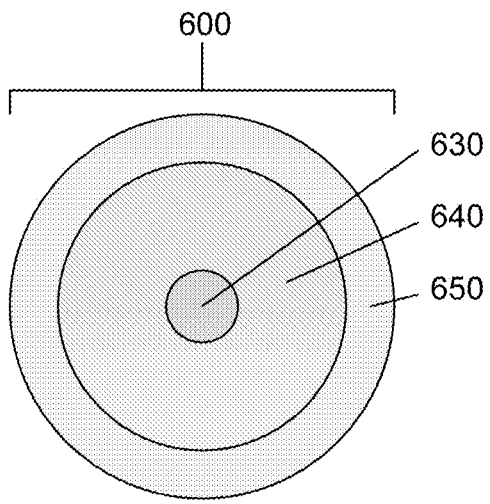
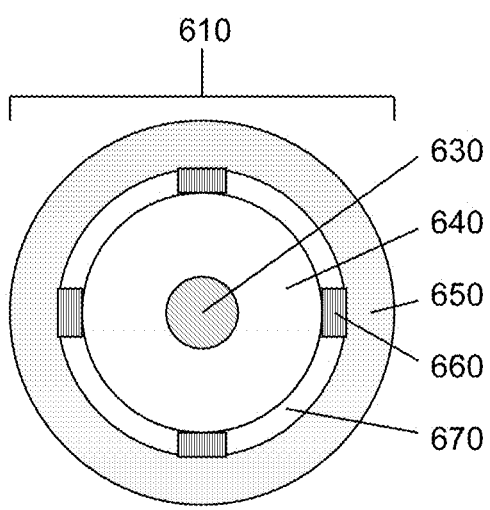
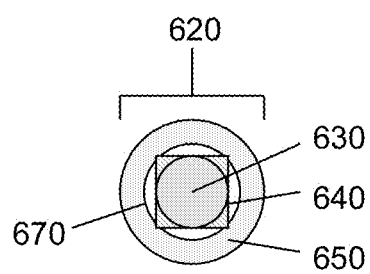

FIG. 21
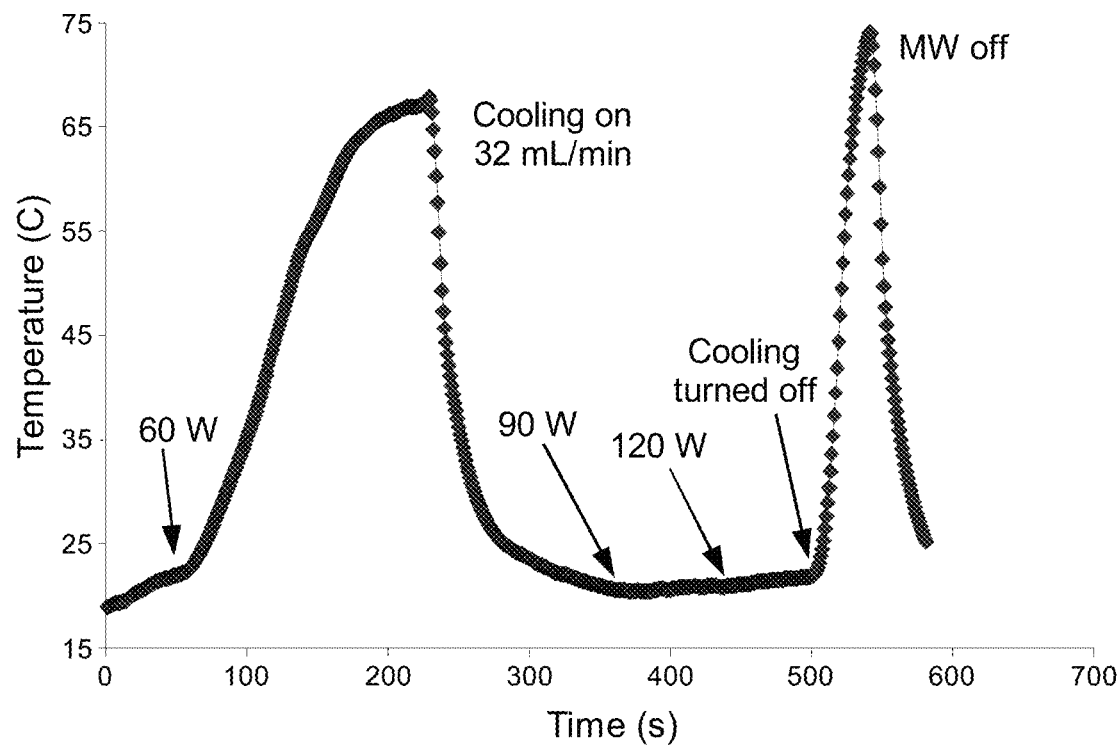
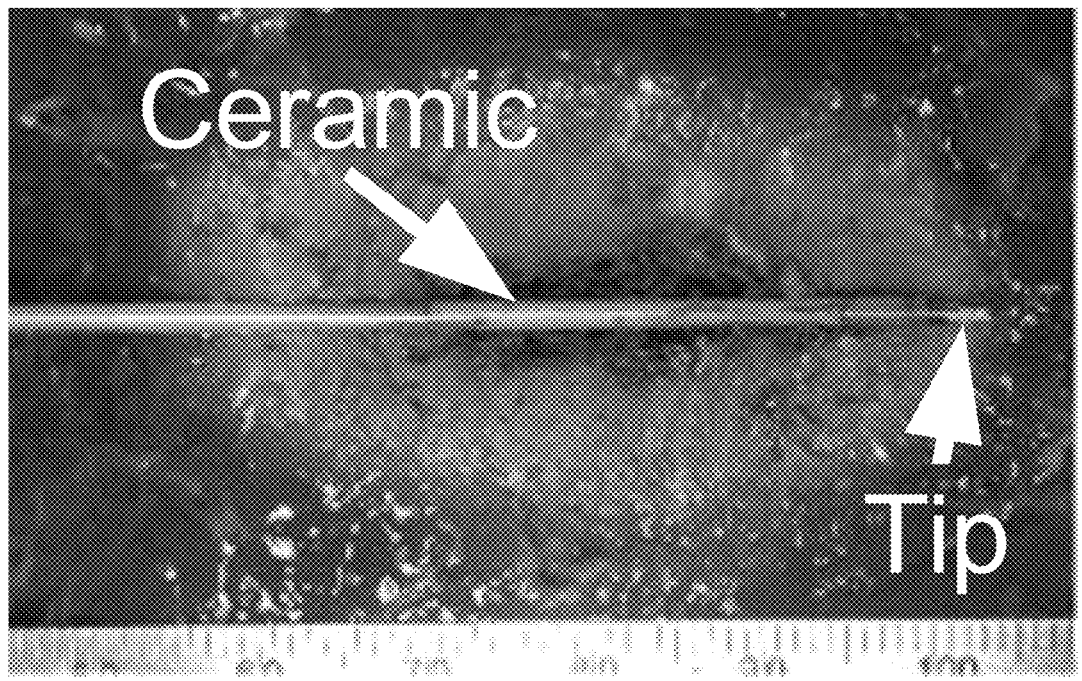

FIG. 25
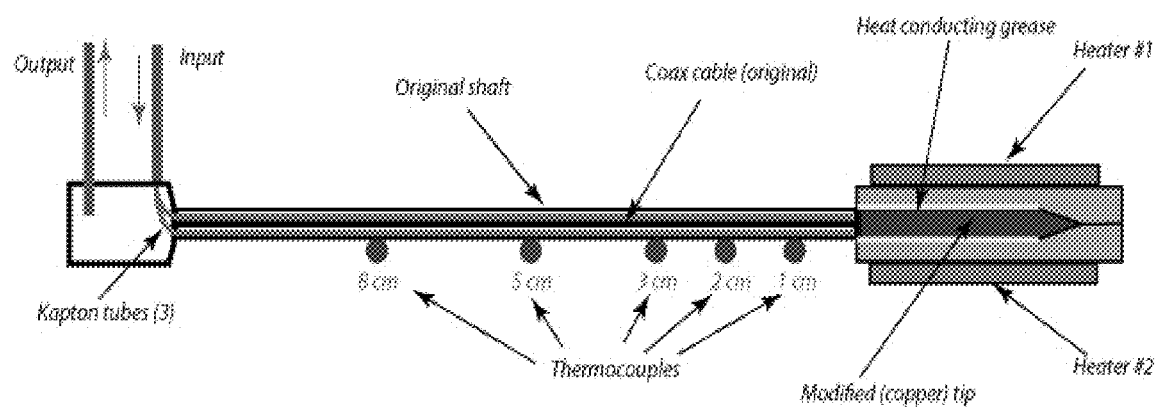
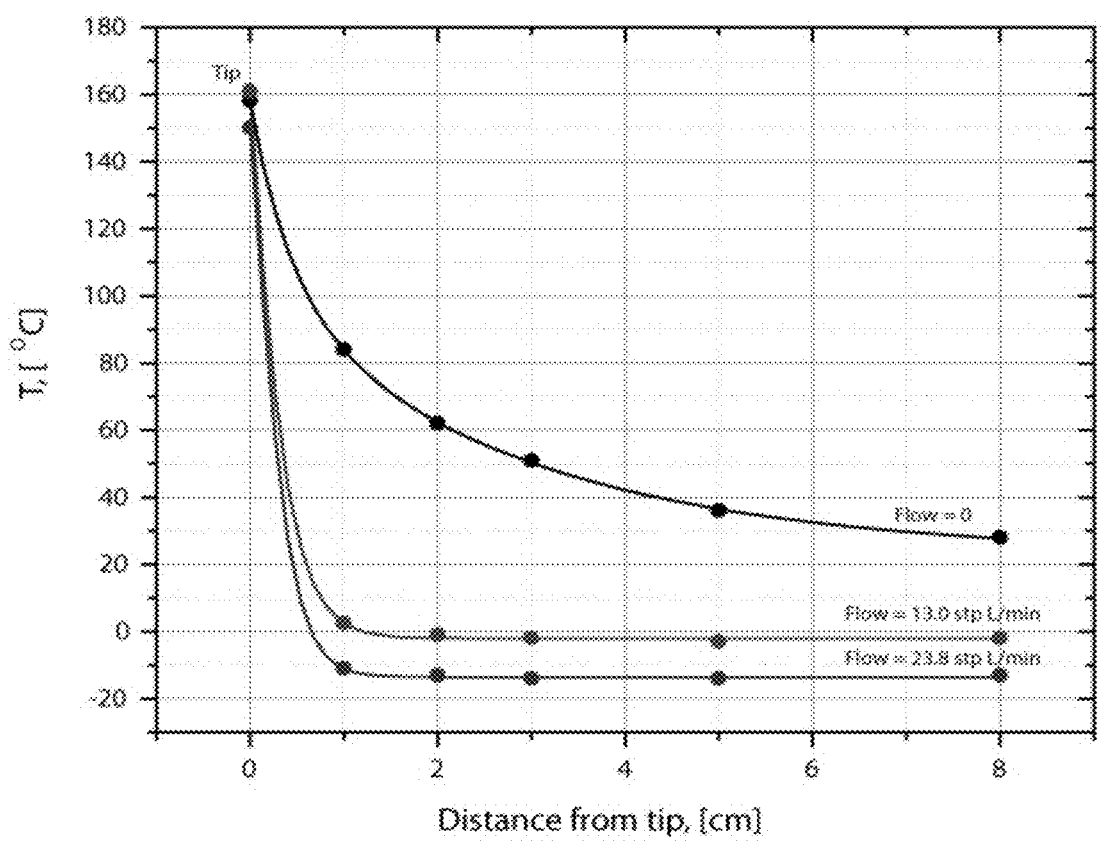

ENERGY DELIVERY SYSTEMS AND USES THEREOF

CROSS-REFERENCE TO RELATED APPLICATIONS

The present application is a divisional of U.S. Patent Application Serial Number which Ser. No. 15/845,785, filed Dec. 18, 2017, now issued as U.S. Pat. No. 10,603,106, which is a continuation of U.S. patent application Ser. No. 14/867,986, filed on Sep. 28, 2015, now issued allowed as U.S. Pat. No. 9,872,729, which is a continuation of U.S. patent application Ser. No. 13/696,001, filed on Jan. 17, 2013, now issued allowed as U.S. Pat. No. 9,861,440, which is a national phase application under 35 U.S.C. § 371 of PCT International Application No. PCT/US2011/035000, filed on May 3, 2011, which claims priority to U.S. Provisional Patent Application No. 61/330,800, filed May 3, 2010, each of which is hereby incorporated by reference in its entirety.

FIELD OF THE INVENTION

The present invention relates to comprehensive systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for delivering energy to difficult to access tissue regions (e.g. peripheral lung tissues), and/or reducing the amount of undesired heat given off during energy delivery.

BACKGROUND

Ablation is an important therapeutic strategy for treating certain tissues such as benign and malignant tumors, cardiac arrhythmias, cardiac dysrhythmias and tachycardia. Most approved ablation systems utilize radio frequency (RF) energy as the ablating energy source. Accordingly, a variety of RF based catheters and power supplies are currently available to physicians. However, RF energy has several limitations, including the rapid dissipation of energy in surface tissues resulting in shallow "burns" and failure to access deeper tumor or arrhythmic tissues. Another limitation of RF ablation systems is the tendency of eschar and clot formation to form on the energy emitting electrodes which limits the further deposition of electrical energy.

Microwave energy is an effective energy source for heating biological tissues and is used in such applications as, for example, cancer treatment and preheating of blood prior to infusions. Accordingly, in view of the drawbacks of the traditional ablation techniques, there has recently been a great deal of interest in using microwave energy as an ablation energy source. The advantage of microwave energy over RF is the deeper penetration into tissue, insensitivity to charring, lack of necessity for grounding, more reliable energy deposition, faster tissue heating, and the capability to produce much larger thermal lesions than RF, which greatly simplifies the actual ablation procedures. Accordingly, there are a number of devices under development that utilize electromagnetic energy in the microwave frequency range as the ablation energy source (see, e.g., U.S. Pat. Nos. 4,641, 649, 5,246,438, 5,405,346, 5,314,466, 5,800,494, 5,957,969, 6,471,696, 6,878,147, and 6,962,586; each of which is herein incorporated by reference in their entireties).

Unfortunately, current devices are limited, by size and flexibility, as to the body regions to which they are capable of delivering energy. For example, in the lungs, the air paths of the bronchial tree get progressively narrower as they branch with increasing depth into the periphery of the lungs. Accurate placement of energy delivery devices to such difficult to reach regions is not feasible with current devices. Improved systems and devices for delivering energy to difficult to reach tissue regions are needed.

SUMMARY OF THE INVENTION

The present invention relates to systems, devices and methods for delivering energy to tissue for a wide variety of applications, including medical procedures (e.g., tissue ablation, resection, cautery, vascular thrombosis, treatment of cardiac arrhythmias and dysrhythmias, electrosurgery, tissue harvest, etc.). In certain embodiments, systems, devices, and methods are provided for treating a tissue region (e.g., a tumor) through application of energy. In some embodiments, systems, devices, and methods are provided for accessing difficult to reach tissue regions with energy delivery devices. In some embodiments, systems, devices, and methods are provided for reducing heat release along energy transmission lines.

The present invention provides systems, devices, and methods that employ components for the delivery of energy to a tissue region (e.g., tumor, lumen, organ, etc.). In some embodiments, the system comprises an energy delivery device and one or more of: a processor, a power supply, a means of directing, controlling and delivering power (e.g., a power splitter), an imaging system, a tuning system, a temperature adjustment system, and a device placement system.

The present invention is not limited to a particular type of energy delivery device. The present invention contemplates the use of any known or future developed energy delivery device in the systems of the present invention. In some embodiments, existing commercial energy delivery devices are utilized. In other embodiments, improved energy delivery devices having an optimized characteristic (e.g., small size, optimized energy delivery, optimized impedance, optimized heat dissipation, etc.) are used. In some such embodiments, the energy delivery device is configured to deliver energy (e.g., microwave energy) to a tissue region. In some embodiments, the energy delivery devices are configured to deliver microwave energy at an optimized characteristic impedance (e.g., configured to operate with a characteristic impedance higher than 50Ω) (e.g., between 50 and 90Ω; e.g., higher than 50, . . . , 55, 56, 57, 58, 59, 60, 61, 62, . . . 90Ω, preferably at 77Ω) (see, e.g., U.S. patent application Ser. No. 11/728,428; herein incorporated by reference in its entirety).

In some embodiments, the present invention provides devices, systems, and methods for placing energy delivery devices in difficult to reach structures, tissue regions, and/or organs (e.g. a branched structure (e.g. human lungs). Accordingly, in some embodiments, the present invention provides a multiple-catheter system or device comprising: a primary catheter, which comprises an inner lumen (the primary lumen); a channel catheter, or sheath, which comprises an inner lumen (channel lumen), wherein the channel catheter is configured to fit within the primary lumen; and one or more insertable tools (e.g. steerable navigation catheter, therapeutic tools (e.g. energy delivery device, biopsy forceps, needles, etc.), etc.), wherein one or more insertable tools are configured to fit within the channel lumen. In some embodiments, the present invention provides a method for accessing difficult to access tissue regions (e.g. highly branched tissue, e.g. periphery of the lungs) comprising: providing a steerable navigation catheter within the channel lumen of a channel catheter, wherein the channel catheter is within the primary lumen of a primary catheter. In some embodiments, a steerable navigation catheter comprises: i) a steerable tip which allows manipulation of its position within a patient, organ, lumen, and/or tissue by a clinician or operator, and ii) a position sensor, which allows tracking of the steerable navigation catheter through a patient, organ, lumen, and/or tissue. In some embodiments, a steerable tip of a steerable navigation catheter functions by pointing tip of the catheter in the desired direction of motion. In some embodiments, manual or automated movement of the catheter results in movement directed in the direction of the tip. In some embodiments, a primary catheter, channel catheter, and steerable navigation catheter are inserted into a tissue region (e.g. bronchi) within a patient, and the primary catheter (e.g. bronchoscope) is inserted as far into the tissue region as the size of the available space (e.g. lumen (e.g. lumen of the brochia)) and the size of the primary catheter (e.g. bronchoscope) will allow. In some embodiments, the primary catheter, channel catheter and steerable navigation catheter are moved through the patient, organ, lumen, and/or tissue via the steerable tip of the steerable navigation catheter and/or steering mechanisms within the primary catheter. In some embodiments, the channel catheter and steerable navigation catheter are extended beyond the end of the primary catheter to access smaller, deeper, and/or more difficult to access tissue regions (e.g. peripheral bronchi, bronchioles, etc.). In some embodiments, the channel catheter and steerable navigation catheter are moved through the patient, organ, lumen, and/or tissue via the steerable tip of the steerable navigation catheter. In some embodiments, the position of the channel catheter and steerable navigation catheter are monitored via the position sensor of the steerable navigation catheter. In some embodiments, the distal ends of the channel catheter and steerable navigation catheter are placed at the target site (e.g. treatment site) in the patient, organ, lumen, and/or tissue (e.g. peripheral bronchi of the lung, peripheral lung nodule, etc.). In some embodiments, upon proper placement of the distal ends of the channel catheter and steerable navigation catheter at the target site (e.g. treatment site), the channel catheter (e.g. distal end of the channel catheter) is secured into position. In some embodiments, the distal end of the channel catheter is secured in proper place using any suitable stabilization mechanism (e.g. screws, clips, wings, etc.), as is understood in the art. In some embodiments, upon proper placement of the distal ends of the channel catheter and steerable navigation catheter at the target site (e.g. treatment site), the steerable navigation catheter is withdrawn through the channel catheter and out the proximal end of the channel catheter. In some embodiments, withdrawing the steerable catheter from the proximal end of the channel catheter leaves the channel catheter in place as a channel for accessing the target site (e.g. treatment site) with any suitable insertable tools (e.g. therapeutic tools (e.g. energy delivery device, biopsy device, etc.), etc.). In some embodiments, a properly positioned and secured channel catheter with the steerable navigation catheter removed comprises a guide channel for accessing the target site (e.g. peripheral bronchi of the lung) with insertable tools (e.g. energy delivery device, biopsy device, etc.) from outside a subject's body. In some embodiments, one or more insertable tools (e.g. therapeutic tools (e.g. energy delivery device, biopsy device, etc.) are inserted through the vacant channel catheter (e.g. guide channel) and the distal tip of the insertable tool is placed at the target site (e.g. treatment site). In some embodiments, an energy delivery device (e.g. microwave ablation device) is inserted through the vacant channel catheter (e.g. guide channel) and the distal tip of the energy delivery device is placed at the target site (e.g. treatment site). In some embodiments, energy (e.g. microwave energy) is delivered through the channel catheter via the inserted energy delivery device to delivery energy to the target site (e.g. to ablate tissue at the target site).

In some embodiments, the present invention provides a method for steering a catheter through a branched structure to a target location, comprising: (a) providing a steerable navigation catheter, wherein the steerable navigation catheter comprises a position sensor element located near a distal tip of the catheter, the position sensor element being part of a system measuring a position and a pointing direction of the tip of the catheter relative to a three-dimensional frame of reference; (b) designating the target location relative to the three-dimensional frame of reference; (c) advancing the catheter into the branched structure; and (d) displaying a representation of at least one parameter defined by a geometrical relation between the pointing direction of the tip of the catheter and a direction from the tip of the catheter towards the target location. In some embodiments, the steerable navigation catheter resides in the lumen of a channel catheter. In some embodiments, the steerable navigation catheter directs the movement of the channel catheter by the above mechanism. In some embodiments, the steerable navigation catheter and channel catheter reside in the lumen of a primary catheter (e.g. bronchoscope). In some embodiments, the steerable navigation catheter directs the movement of the channel catheter and primary catheter by the above mechanism. In some embodiments, a primary catheter has a separate direction control (steering) mechanism from the steerable navigation catheter.

In some embodiments, a representation of at least one parameter defined by a geometrical relation between (i) the pointing direction of the tip of the steerable navigation catheter and (ii) a direction from the tip of the steerable navigation catheter towards the target location is displayed (e.g. to provide users with information regarding the position and/or direction of the steerable navigation catheter). In some embodiments, the at least one parameter includes an angular deviation between the pointing direction of the tip of the steerable navigation catheter and a direction from the tip of the steerable navigation catheter towards the target location. In some embodiments, the at least one parameter includes a direction of deflection required to bring the pointing direction of the steerable navigation catheter into alignment with the target location. In some embodiments, the representation of at least one parameter is displayed in the context of a representation of a view taken along the pointing direction of the tip of the steerable navigation catheter. In some embodiments, the position sensor element is part of a six-degrees-of-freedom position measuring system measuring the position and attitude of the tip of the steerable navigation catheter in three translational and three rotational degrees of freedom. In some embodiments, the steerable navigation catheter is further provided with a multi-directional steering mechanism configured for selectively deflecting a distal portion of the catheter in any one of at least three different directions. In some embodiments, the steering mechanism is controlled by a user via a control device at the proximal end of the steerable navigation catheter. In some embodiments, the steering mechanism is controlled by a user via a remote control device. In some embodiments, a path traveled by the tip of the steerable navigation catheter is monitored by use of the position sensor element and a representation of the path traveled is displayed together with a current position of the tip, the representation being projected as viewed from at least one direction non-parallel to the pointing direction of the tip.

In some embodiments, the target location (e.g. treatment location (e.g. tumor)) is designated by: (a) designating a target location by use of computerized tomography data of a subject; and (b) registering the computerized tomography data with the three-dimensional frame of reference. In some embodiments, other mapping data (e.g. MRI, x-ray, PET, etc.) is substituted for computerized tomography data in any embodiments of the present invention described herein. In some embodiments, the registering is performed by: (a) providing the steerable catheter with a camera; (b) generating a camera view of each of at least three distinctive features within the subject; (c) generating from the computerized tomography data a simulated view of each of the at least three distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography data and the three-dimensional frame of reference. In some embodiments, an intended route through a subject (e.g. through a branched structure (e.g. a lung structure (e.g. bronchi)) within a subject) to a target location is designated by use of the computerized tomography data and a representation of the intended route is displayed together with a current position of the tip, the representation being projected as viewed from at least one direction non-parallel to the pointing direction of the tip. In some embodiments: (a) a current position of the position sensor element is detected; (b) a virtual endoscopy image is generated from the computerized tomography data corresponding to an image that would be viewed by a camera located in predefined spatial relationship and alignment relative to the position sensor element; and (c) displaying the virtual endoscopy image.

In some embodiments, a catheter system of the present invention comprises a steerable navigation catheter and a channel catheter having a lumen extending from a proximal insertion opening to a distal opening; and a guide element configured for insertion through the proximal opening of the sheath to an inserted position extending along the lumen to the distal opening. In some embodiments, a channel catheter is a sheath, through which a steerable navigation catheter (or an energy delivery device) can be inserted and/or withdrawn. In some embodiments, the steerable navigation catheter is used to position the channel catheter such that the distal tips of the steerable navigation catheter and channel catheter are adjacent to the target location (e.g. treatment site (e.g. tumor)). In some embodiments, the channel catheter is locked into proper position at the target location. In some embodiments, the steerable navigation catheter is withdrawn from the channel lumen leaving an open channel extending from the point of insertion into the subject to the target site. In some embodiments, the channel catheter is available for insertion of an insertable tool (e.g. medical tool (e.g. energy delivery device). In some embodiments, the present invention provides a method comprising: (a) guiding a steerable navigation catheter within a channel catheter to a position with the tip adjacent to the target location; and (b) withdrawing the steerable navigation catheter from the channel catheter to leave the channel lumen available for insertion of a medical tool (e.g. energy delivery device).

In some embodiments, a catheter system provides a primary catheter (e.g. flexible endoscope, flexible bronchoscope, etc.) having an operation handle and a primary lumen, a channel catheter deployed within the primary lumen and having a channel lumen, and a steerable navigation catheter deployed within the channel lumen. In some embodiments, the present invention provides a method comprising: inserting the primary catheter, housing the channel catheter and steerable navigation catheter, into a subject, organ, tissue, and/or lumen until the primary catheter reaches its maximum insertion distance (e.g. limited by size from further insertion; (b) locking the steerable navigation catheter within the channel lumen to prevent movement of the steerable navigation catheter relative to the channel catheter; (c) guiding the steerable navigation catheter and channel catheter beyond the distal end of the primary catheter to the target location; (d) locking the channel catheter within the primary lumen to prevent relative movement of the channel catheter relative to the primary catheter and/or operation handle; and (e) unlocking and withdrawing the steerable navigation element from the channel catheter so as to leave the channel in place as a guide for inserting a tool (e.g. energy delivery device) to the target location. In some embodiments, a system or device of the present invention comprises a stabilization and/or anchoring mechanism to hold one or more elements in place when deployed in a subject and/or body region. In some embodiments, a selectively actuatable anchoring mechanism is associated with a portion of the channel catheter. In some embodiments, the selectively actuatable anchoring mechanism includes an inflatable element. In some embodiments, the selectively actuatable anchoring mechanism includes a mechanically deployed element.

In some embodiments, a channel catheter and/or steerable navigation catheter includes an image sensor deployed for generating an image in the pointing direction of the catheter. In some embodiments, the image sensor is configured to be withdrawn with the steerable navigation catheter.

In some embodiments, the present invention provides a method for achieving registration between computerized tomography data (or other mapping data, e.g., MRI, PET, X-ray, etc.) and a three dimensional frame of reference of a position measuring system, the method comprising: (a) providing a catheter with: (i) a position sensor element which operates as part of the position measuring system to allow measurement of a position and a pointing direction of the tip of the catheter relative to the three-dimensional frame of reference, and (ii) an image sensor; (b) generating from the computerized tomography data at least three simulated views of distinctive features within the branched structure; (c) generating at least three camera views of the distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography image and the three-dimensional frame of reference. In some embodiments, designation of a reference point within each of the camera views by the operator is performed by the operator bringing the position sensor element into proximity with the reference point. In some embodiments, designation of a reference point within each simulated view by the operator is performed by: (a) the operator selecting a simulated image reference point within each simulated view; (b) calculating from the simulated image reference point a simulated-viewing-point-to-reference-point vector; and (c) calculating a point of intersection between the simulated-viewing-point-to-reference-point vector and a tissue surface in a numerical model of a portion of the body derived from the computerized tomography data. In some embodiments: (a) at least one location within the computerized tomography data is identified; (b) a position of the at least one location is calculated within the three-dimensional frame of reference; and (c) a representation of the at least one location is displayed together with a representation of a position of the position sensor element. In some embodiments, the at least one location includes a target location (e.g. treatment location (e.g. tumor, bronchi (e.g. peripheral bronchi), etc.)) to which a medical tool (e.g. energy delivery device (e.g. microwave ablation device), etc.) is to be directed. In some embodiments, the at least one location is a series of locations defining a planned path along which a medical tool is to be directed. In some embodiments, a method for achieving registration between computerized tomography data and a three dimensional frame of reference of a position measuring system, the method comprising: (a) providing a steerable navigation catheter with: (i) a position sensor element which operates as part of the position measuring system to allow measurement of a position and a pointing direction of the tip of the catheter relative to the three-dimensional frame of reference, and (ii) an image sensor; (b) moving the tip of the catheter along a first branch portion of a branched structure and deriving a plurality of images from the camera, each image being associated with corresponding position data of the position sensor in the three dimensional frame of reference; (c) processing the images and corresponding position data to derive a best-fit of a predefined geometrical model to the first branch portion in the three dimensional frame of reference; (d) repeating steps (b) and (c) for a second branch portion of the branched structure; and (e) correlating the geometrical models of the first and second branch portions with the computerized tomography data to derive a best fit registration between the computerized tomography data and the three dimensional frame of reference. In some embodiments, the processing the images and corresponding position data includes: (a) identifying visible features each of which is present in plural images taken at different positions; (b) for each of the visible features, deriving a camera-to-feature direction in each of a plurality of the images; (c) employing the camera-to-feature directions and corresponding position data to determine a feature position for each visible feature; and (d) deriving a best-fit of the predefined geometrical model to the feature positions. In some embodiments, the predefined geometrical model is a cylinder. In some embodiments: (a) at least one location within the computerized tomography data is identified; (b) a position of the at least one location within the three-dimensional frame of reference is calculated; and (c) a representation of the at least one location is displayed together with a representation of a position of the position sensor element. In some embodiments, the at least one location includes a target location (e.g. treatment location (e.g. tumor (e.g. tumor in the peripheral bronchi))) to which a medical tool (e.g. energy delivery device (e.g. microwave ablation device) is to be directed. In some embodiments, the at least one location is a series of locations defining a planned path along which a medical tool is to be directed.

In some embodiments, the present invention provides a steering mechanism for selectively deflecting a distal portion of a steerable navigation catheter in any one of at least two independent directions, the mechanism comprising: (a) at least three elongated tensioning elements extending along the catheter and configured such that tension applied to any one of the tensioning elements causes deflection of a tip of the catheter in a corresponding predefined direction; (b) an actuator displaceable from a first position to a second position; and (c) a selector mechanism configured for selectively mechanically interconnecting a selected at least one of the elongated tensioning elements and the actuator such that displacement of the actuator from the first position to the second position applies tension to the selected at least one of the elongated tensioning elements. In some embodiments, a first state of the selector mechanism mechanically interconnects a single one of the elongated tensioning elements with the actuator such that displacement of the actuator generates deflection of the tip in one of the predefined directions, and a second state of the selector mechanism mechanically interconnects two of the elongated tensioning elements with the actuator such that displacement of the actuator generates deflection of the tip in an intermediate direction between two of the predefined directions. In some embodiments, the at least three tensioning elements includes an even number of the tensioning elements, pairs of the tensioning elements being implemented as a single elongated element extending from the selector mechanism along the catheter to the tip and back along the steerable navigation catheter to the selector mechanism. In some embodiments, the at least three tensioning elements is implemented as four tensioning elements deployed such that each tensioning element, when actuated alone, causes deflection of the tip in a different one of four predefined directions separated substantially by multiples of 90°. In some embodiments, a first state of the selector mechanism mechanically interconnects a single one of the elongated tensioning elements with the actuator such that displacement of the actuator generates deflection of the tip in one of the four predefined directions, and a second state of the selector mechanism mechanically interconnects two of the elongated tensioning elements with the actuator such that displacement of the actuator generates deflection of the tip in one of four intermediate directions each lying between two of the four predefined directions. In some embodiments, the actuator includes a ring which is slidable relative to a handle associated with the catheter, and wherein the selector mechanism includes a slide attached to each of the tensioning elements and slidably deployed within the handle and at least one projection projecting from the ring such that, when the ring is rotated, the at least one projection selectively engages at least one of the slides such that displacement of the ring causes movement of the at least one slide.

In some embodiments, the present invention provides devices, systems, and methods for reducing overheating during energy delivery to tissues in a subject. One significant source of undesired overheating of the device is the dielectric heating of the insulator (e.g., the coaxial insulator), potentially resulting in collateral tissue damage. The energy delivery devices of the present invention are designed to prevent undesired overheating. The energy delivery devices are not limited to a particular manner of preventing undesired device heating. In some embodiments, the devices employ circulation of coolant. In some embodiments, the devices are configured to detect an undesired rise in temperature within the device (e.g., along the outer conductor) and automatically or manually reduce such an undesired temperature rise through flowing of coolant through coolant passage channels. In some embodiments, devices employ a porous insulator as a dielectric material, thereby allowing coolant to flow through the dielectric material. In some embodiments, one or more coolant channels provide a means for reducing heat loss from transmission lines to the surrounding tissue. In some embodiments, constant low-power or pulsed high-power energy is delivered to reduce overheating. In some embodiments, coolant channels run through the dielectric material. In some embodiments, coolant serves as a dielectric material. In some embodiments, the dielectric space is all or partially filled with coolant material.

In some embodiments, the energy delivery devices have improved cooling characteristics. For example, in some embodiments, the devices permit the use of coolant without increasing the diameter of the device. This is in contrast to existing devices that flow coolant through an external sleeve or otherwise increase the diameter of the device to accommodate the flow of a coolant. In some embodiments, the energy delivery devices have therein one or more coolant passage channels for purposes of reducing unwanted heat dissipation (see, e.g., U.S. patent application Ser. No. 11/728,460; herein incorporated by reference in its entirety). In some embodiments, energy delivery devices have therein a tube (e.g., needle, plastic tube, etc.) that runs the length of or partially runs the length of the device, designed to prevent device overheating through circulation of coolant material. In some embodiments, channels or tubes displace material from a dielectric component located between the inner and outer conductors of a coaxial cable. In some embodiments, coolant material (e.g. air, $CO_2$, etc.) is the dielectric material. In some embodiments, coolant material comprises all or part of the dielectric space (e.g. the space between the inner conductor and outer conductor of a coaxial transmission line). In some embodiments, channels or tubes replace the dielectric material or substantially replace the dielectric material. In some embodiments, a porous dielectric material is used to accommodate the flow of coolant through the dielectric material. In some embodiments, channel or tubes displace a portion of the outer conductor. For example, in some embodiments, a portion of the outer conductor is removed or shaved off to generate a passageway for the flow of coolant. One such embodiment is shown in FIG. 12. A coaxial cable 900 has an outer conductor 910, an inner conductor 920, and a dielectric material 930. A region 940 of the outer conductor is removed, creating space for coolant flow. The only remaining outer conductor material circumscribes or substantially circumscribes the coaxial cable is at distal 950 and proximal 960 end regions. A thin strip of conductive material 970 connects the distal 950 and proximal 960 end regions. A thin channel 980 is cut from the conductive material at the proximal end region 960 to permit coolant flow into the region where the outer conductive material was removed (or was manufacture to be absent) 940. The present invention is not limited by the size or shape of the passageway, so long as coolant can be delivered. For example, in some embodiments, the passageway is a linear path that runs the length of the coaxial cable. In some embodiments, spiral channels are employed. In some embodiments, the tube or channel displaces or replaces at least a portion of the inner conductor. For example, large portions of the inner conductor may be replaced with a coolant channel, leaving only small portions of metal near the proximal and distal ends of the device to permit tuning, wherein the portions are connected by a thin strip of conducting material. In some embodiments, a region of interior space is created within the inner or outer conductor to create one or more channels for coolant. For example, the inner conductor may be provided as a hollow tube of conductive material, with a coolant channel provided in the center. In such embodiments, the inner conductor can be used either for inflow or outflow (or both) of coolant. In some embodiments, a coolant channel displaces a portion of the dielectric material. In some embodiments, channels are formed by gaps within the dielectric material.

In some embodiments in which a coolant tube is placed within the device, the tube has multiple channels for intake and outtake of coolant through the device. The device is not limited to a particular positioning of the tube (e.g., coolant needle) within the dielectric material. In some embodiments, the tube is positioned along the outside edge of the dielectric material, the middle of the dielectric material, or at any location within the dielectric material. In some embodiments, the dielectric material is pre-formed with a channel designed to receive and secure the tube. In some embodiments, a handle is attached with the device, wherein the handle is configured to, for example, control the passing of coolant into and out of the tube. In some embodiments, the tube is flexible. In some embodiments, the tube is inflexible (e.g. regions of inflexibility). In some embodiments, the portions of the tube are flexible, while other portions are inflexible. In some embodiments, the tube is compressible. In some embodiments, the tube is incompressible. In some embodiments, portions of the tube are compressible, while other portions are incompressible. The tube is not limited to a particular shape or size. In some embodiments, wherein the tube is a coolant needle (e.g., a 29 gauge needle or equivalent size) that fits within a coaxial cable having a diameter equal or less than a 12 gauge needle. In some embodiments, the exterior of the tube has a coating of adhesive and/or grease so as to secure the tube or permit sliding movement within the device. In some embodiments, the tube has one or more holes along its length that permit release of coolant into desired regions of the device. In some embodiments, the holes are initially blocked with a meltable material, such that a particular threshold of heat is required to melt the material and release coolant through the particular hole or holes affected. As such, coolant is only released in areas that have reached the threshold heat level.

In some embodiments, coolant is preloaded into the antenna, handle or other component of the devices of the present invention. In other embodiments, the coolant is added during use. In some pre-loaded embodiments, a liquid coolant is preloaded into, for example, the distal end of the antenna under conditions that create a self-perpetuating vacuum. In some such embodiments, as the liquid coolant vaporizes, more fluid is drawn in by the vacuum.

The present invention is not limited by the nature of the coolant material employed. Coolants included, but are not limited to, liquids and gases. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, the coolant fluid also serves as the dielectric material. In some embodiments, the coolant is a gas compressed at or near its critical point. In some embodiments, cooling occurs, at least in part, by changing concentrations of coolant, pressure, or volume. For example, cooling can be achieved via gas coolants using the Joule-Thompson effect. In some embodiments, the cooling is provided by a chemical reaction. The devices are not limited to a particular type of temperature reducing chemical reaction. In some embodiments, the temperature reducing chemical reaction is an endothermic reaction. The devices are not limited to a particular manner of applying endothermic reactions for purposes of preventing undesired heating. In some embodiments, first and second chemicals are flowed into the device such that they react to reduce the temperature of the device. In some embodiments, the device is prepared with the first and second chemicals preloaded in the device. In some embodiments, the chemicals are separated by a barrier that is removed when desired. In some embodiments, the barrier is configured to melt upon exposure to a predetermined temperature or temperature range. In such embodiments, the device initiates the endothermical reaction only upon reaching a heat level that merits cooling. In some embodiments, multiple different barriers are located throughout the device such that local cooling occurs only at those portions of the device where undesired heating is occurring. In some embodiment, the barriers used are beads that encompass one of the two chemicals. In some embodiments, the barriers are walls (e.g., discs in the shape of washers) that melt to combine the two chemicals. In some embodiments, the barriers are made of wax that is configured to melt at a predetermined temperature. The devices are not limited to a particular type, kind or amount of meltable material. In some embodiments, the meltable material is biocompatible. The devices are not limited to a particular type, kind, or amount of first and second chemicals, so long as their mixture results in a temperature reducing chemical reaction. In some embodiments, the first material includes barium hydroxide octahydrate crystals and the second material is dry ammonium chloride. In some embodiments, the first material is water and the second material is ammonium chloride. In some embodiments, the first material is thionyl chloride ($SOCl_2$) and the second material is cobalt(II) sulfate heptahydrate. In some embodiments, the first material is water and the second material is ammonium nitrate. In some embodiments, the first material is water and the second material is potassium chloride. In some embodiments, the first material is ethanoic acid and the second material is sodium carbonate. In some embodiments, a meltable material is used that, itself, reduces heat by melting an flowing in a manner such that the heat at the outer surface of the device is reduced.

In some embodiments, the energy delivery devices prevent undesired heating and/or maintain desired energy delivery properties through adjusting the amount of energy emitted from the device (e.g., adjusting the energy wavelength resonating from the device) as temperatures increase. The devices are not limited to a particular method of adjusting the amount of energy emitted from the device. In some embodiments, the devices are configured such that as the device reaches a certain threshold temperature or as the device heats over a range, the energy wavelength resonating from the device is adjusted. The devices are not limited to a particular method for adjusting energy wavelength resonating from the device. In some embodiments, the device has therein a material that changes in volume as the temperature increases. The change in volume is used to move or adjust a component of the device that affects energy delivery. For example, in some embodiments, a material is used that expands with increasing temperature. The expansion is used to move the distal tip of the device outward (increasing its distance from the proximal end of the device), altering the energy delivery properties of the device. This finds particular use with the center-fed dipole embodiments of the present invention. In some embodiments, the energy delivery devices prevent undesired heating and/or maintain desired energy delivery properties through adjusting the energy delivery program without lowering the energy wavelength. In some embodiments, pulsed programs deliver bursts of energy to the treatment site (e.g. bursts of energy sufficient to perform the desired task (e.g. ablation)) without inducing undesired heating along the transmission path. In some embodiments, pulsed programs reduce heat along the transmission pathway when compared to continuous delivery programs. In some embodiments, different patterns of pulse programs effectively balance the potentially conflicting desires of large amounts of energy delivered to the treatment site and reduced heat along the delivery path. In some embodiments, different pulse patterns (e.g. length of time delivering energy, length of time between energy pulses) and different energy levels (e.g. energy wavelengths) are utilized to optimize energy-delivery and path-heating.

In certain embodiments, the present invention provides a device comprising an antenna configured for delivery of energy to a tissue, wherein a distal end of the antenna comprises a center-fed dipole component comprising a rigid hollow tube encompassing a conductor, wherein a stylet is secured within the hollow tube. In some embodiments, the hollow tube has a diameter equal to or less than a 20-gauge needle. In some embodiments, the hollow tube has a diameter equal to or less than a 17-gauge needle. In some embodiments, the hollow tube has a diameter equal to or less than a 12-gauge needle. In some embodiments, the device further comprises a tuning element for adjusting the amount of energy delivered to the tissue. In some embodiments, the device is configured to deliver a sufficient amount of energy to ablate the tissue or cause thrombosis. In some embodiments, the conductor extends halfway through the hollow tube. In some embodiments, the hollow tube has a length $\lambda/2$, wherein $\lambda$ is the electromagnetic field wavelength in the medium of the tissue. In some embodiments, an expandable material is positioned near the stylet such that as the device increases in temperature the expandable material expands and pushes onto the stylet moving the stylet and changes the energy delivery properties of the device. In some embodiments, the expandable material is positioned behind (proximal to) a metal disc that provides the resonant element for the center-fed dipole device. As the material expands, the disc is pushed distally, adjusting the tuning of the device. The expandable material is preferably selected so that the rate of expansion coincides with a desired change in energy delivery for optimal results. However, it should be understood that any change in the desired directions finds use with the invention. In some embodiments, the expandable material is wax.

In some embodiments, the device has a handle attached with the device, wherein the handle is configured to, for example, control the passing of coolant into and out of coolant channels. In some embodiments, only the handle is cooled. In some embodiments, the handle is configured to deliver a gaseous coolant compressed at or near its critical point. In other embodiments, the handle and an attached antenna are cooled. In some embodiments, the handle automatically passes coolant into and out of the coolant channels after a certain amount of time and/or as the device reaches a certain threshold temperature. In some embodiments, the handle automatically stops passage of coolant into and out of the coolant channels after a certain amount of time and/or as the temperature of the device drops below a certain threshold temperature. In some embodiments, coolant flowed through the handle is manually controlled. In some embodiments, the handle has thereon one or more (e.g., 1, 2, 3, 4, 5, 6, 7, 8, 9, 10, etc.) lights (e.g., display lights (e.g., LED lights)). In some embodiments, the lights are configured to for identification purposes. For example, in some embodiments, the lights are used to differentiate between different probes (e.g., activation of a first probe displays one light; a second probe two lights, a third probe three lights, or each probe has its own designated light, etc.). In some embodiments, the lights are used to identify the occurrence of an event (e.g., the transmission of coolant through the device, the transmission of energy through the device, a movement of the respective probe, a change in a setting (e.g., temperature, positioning) within the device, etc.). The handles are not limited to a particular manner of display (e.g., blinking, alternate colors, solid colors, etc).

In some embodiments, the energy delivery devices have therein a center fed dipole component (see, e.g., U.S. patent application Ser. No. 11/728,457; herein incorporated by reference in its entirety). In some embodiments, the energy delivery devices comprise a catheter with multiple segments for transmitting and emitting energy (see, e.g., U.S. patent application Ser. Nos. 11/237,430, 11/237,136, and 11/236,985; each herein incorporated by reference in their entireties). In some embodiments, the energy delivery devices comprise a triaxial microwave probe with optimized tuning capabilities to reduce reflective heat loss (see, e.g., U.S. Pat. No. 7,101,369; see, also, U.S. patent application Ser. Nos. 10/834,802, 11/236,985, 11/237,136, 11,237,430, 11/440, 331, 11/452,637, 11/502,783, 11/514,628; and International Patent Application No. PCT/US05/14534; herein incorporated by reference in its entirety). In some embodiments, the energy delivery devices emit energy through a coaxial transmission line (e.g., coaxial cable) having air or other gases as a dielectric core (see, e.g., U.S. patent application Ser. No. 11/236,985; herein incorporated by reference in its entirety). In some such embodiments, materials that support the structure of the device between the inner and outer conductors may be removed prior to use. For example, in some embodiments, the materials are made of a dissolvable or meltable material that is removed prior to or during use. In some embodiments, the materials are meltable and are removed during use (upon exposure to heat) so as to optimize the energy delivery properties of the device over time (e.g., in response to temperature changes in tissue, etc.).

The present invention is not limited to a particular coaxial transmission line shape. Indeed, in some embodiments, the shape of the coaxial transmission line and/or the dielectric element is adjustable to fit a particular need. In some embodiments, the cross-sectional shape of the coaxial transmission line and/or the dielectric element is circular. In some embodiments, the cross-sectional shape is non-circular (e.g., oval, etc.). Such shapes may apply to the coaxial cable as a whole, or may apply to one or more sub-components only. For example, an oval dielectric material may be placed in a circular outer conductor. This, for example, has the advantage of creating two channels that may be employed, for example, to circulate coolant. As another example, square/rectangular dielectric material may be placed in a circular conductor. This, for example, has the advantage of creating four channels. Different polygonal shapes in the cross-section (e.g., pentagon, hexagon, etc.) may be employed to create different numbers and shapes of channels. The cross-sectional shape need not be the same throughout the length of the cable. In some embodiments, a first shape is used for a first region (e.g., a proximal region) of the cable and a second shape is used for a second region (e.g., a distal region) of the cable. Irregular shapes may also be employed. For example, a dielectric material having an indented groove running its length may be employed in a circular outer conductor to create a single channel of any desired size and shape. In some embodiments, the channel provides space for feeding coolant, a needle, or other desired components into the device without increasing the ultimate outer diameter of the device.

Likewise, in some embodiments, an antenna of the present invention has a non-circular cross-sectional shape along its length or for one or more subsections of its length. In some embodiments, the antenna is non-cylindrical, but contains a coaxial cable that is cylindrical. In other embodiments, the antenna is non-cylindrical and contains a coaxial cable that is non-cylindrical (e.g., matching the shape of the antenna or having a different non-cylindrical shape). In some embodiments, having any one or more components (e.g., cannula, outer shell of antenna, outer conductor of coaxial cable, dielectric material of coaxial cable, inner conductor of coaxial cable) possessing a non-cylindrical shape permits the creation of one or more channels in the device that may be used, among other reasons, to circulate coolant. Non-circular shapes, particularly in the outer diameter of the antenna also find use for certain medical or other applications. For example, a shape may be chosen to maximize flexibility or access to particular inner body locations. Shape may also be chosen to optimize energy delivery. Shape (e.g., non-cylindrical shape) may also be selected to maximize rigidity and/or strength of the device, particularly for small diameter devices.

In certain embodiments, the present invention provides a device comprising an antenna, wherein the antenna comprises an outer conductor enveloped around an inner conductor, wherein the inner conductor is designed to receive and transmit energy, wherein the outer conductor has therein at least one gap positioned circumferentially along the outer conductor, wherein multiple energy peaks are generated along the length of the antenna, the position of the energy peaks controlled by the location of the gap. In some embodiments, the energy is microwave energy and/or radiofrequency energy. In some embodiments, the outer conductor has therein two of the gaps. In some embodiments, the antenna comprises a dielectric layer disposed between the inner conductor and the outer conductor. In some embodiments, the dielectric layer has near-zero conductivity. In some embodiments, the device further comprises a stylet. In some embodiments, the inner conductor has a diameter of approximately 0.013 inches or less.

In some embodiments, any gaps or inconsistencies or irregularities in the outer conductor or outer surface of the device are filled with a material to provide a smooth, even, or substantially smooth, even outer surface. In some embodiments, a heat-resistant, resin is used to fill gaps, inconsistencies, and/or irregularities. In some embodiments, the resin is biocompatible. In other embodiments, it is not biocompatible, but, for example, can be coated with a biocompatible material. In some embodiments, the resin is configurable to any desired size or shape. As such, the resin, when hardened, may be used to provide a sharp stylet tip to the devices or any other desired physical shape.

In some embodiments, the device comprises a sharp stylet tip. The tip may be made of any material. In some embodiments, the tip is made from hardened resin. In some embodiments, the tip is metal. In some such embodiments, the metal tip is an extension of a metal portion of an antenna and is electrically active. In some embodiments, the distal tip of a device comprises a cutting trocar.

In some embodiments, the energy delivery devices are configured to delivery energy to a tissue region within a system comprising a processor, a power supply, a means of directing, controlling and delivering power (e.g., a power splitter with the capability of individual control of power delivery to each antenna), an imaging system, a tuning system, a temperature measurement adjustment system, and/or a device placement system.

The present invention is not limited to a particular type of processor. In some embodiments, the processor is designed to, for example, receive information from components of the system (e.g., temperature monitoring system, energy delivery device, tissue impedance monitoring component, etc.), display such information to a user, and manipulate (e.g., control) other components of the system. In some embodiments, the processor is configured to operate within a system comprising an energy delivery device, a power supply, a means of directing, controlling and delivering power (e.g., a power splitter), an imaging system, a tuning system, and/or a temperature adjustment system.

The present invention is not limited to a particular type of power supply. In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the power supply utilizes a power splitter to permit delivery of energy to two or more energy delivery devices. In some embodiments, the power supply is configured to operate within a system comprising a power splitter, a processor, an energy delivery device, an imaging system, a tuning system, and/or a temperature adjustment system.

The present invention is not limited to a particular type of imaging system. In some embodiments, the imaging system utilizes imaging devices (e.g., endoscopic devices, stereotactic computer assisted neurosurgical navigation devices, thermal sensor positioning systems, motion rate sensors, steering wire systems, intraprocedural ultrasound, fluoroscopy, computerized tomography magnetic resonance imaging, nuclear medicine imaging devices triangulation imaging, interstitial ultrasound, microwave imaging, acoustic tomography, dual energy imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention. In some embodiments, the imaging system is configured to provide location information of particular components of the energy delivery system (e.g., location of the energy delivery device). In some embodiments, the imaging system is configured to operate within a system comprising a processor, an energy delivery device, a power supply, a tuning system, and/or a temperature adjustment system. In some embodiments, the imaging system is located within the energy delivery device. In some embodiments, the imaging system provides qualitative information about the ablation zone properties (e.g., the diameter, the length, the cross-sectional area, the volume). The imaging system is not limited to a particular technique for providing qualitative information. In some embodiments, techniques used to provide qualitative information include, but are not limited to, time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices. In some embodiments, the interstitial device provides a signal and/or detection for imaging (e.g., electro-acoustic imaging, electromagnetic imaging, electrical impedance tomography).

The present invention is not limited to a particular tuning system. In some embodiments, the tuning system is configured to permit adjustment of variables (e.g., amount of energy delivered, frequency of energy delivered, energy delivered to one or more of a plurality of energy devices that are provided in the system, amount of or type of coolant provided, etc.) within the energy delivery system. In some embodiments, the tuning system comprises a sensor that provides feedback to the user or to a processor that monitors the function of an energy delivery device continuously or at time points. The sensor may record and/or report back any number of properties, including, but not limited to, heat (e.g., temperature) at one or more positions of a components of the system, heat at the tissue, property of the tissue, qualitative information of the region, and the like. The sensor may be in the form of an imaging device such as CT, ultrasound, magnetic resonance imaging, fluoroscopy, nuclear medicine imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.). In some embodiments, the tuning system is configured to operate within a system comprising a processor, an energy delivery device, a power supply, an imaging, and/or a temperature adjustment system. In some embodiments, the imaging or other control components provide feedback to the ablation device so that the power output (or other control parameter) can be adjusted to provide an optimum tissue response.

The present invention is not limited to a particular temperature adjustment system. In some embodiments, the temperature adjustment systems are designed to reduce unwanted heat of various components of the system (e.g., energy delivery devices) during medical procedures (e.g., tissue ablation) or keep the target tissue within a certain temperature range. In some embodiments, the temperature adjustment systems are configured to operate within a system comprising a processor, an energy delivery device, a power supply, a means of directing, controlling and delivering power (e.g., a power splitter), a tuning system, and/or an imaging system. In some embodiments, the temperature adjustment system is designed to cool the energy delivery device to a temperature that is sufficient to temporarily adhere the device to internal patient tissue so as to prevent the energy device from moving during a procedure (e.g., the ablation procedure).

In some embodiments, the systems further comprise temperature monitoring or reflected power monitoring systems for monitoring the temperature or reflected power of various components of the system (e.g., energy delivery devices) and/or a tissue region. In some embodiments, the monitoring systems are designed to alter (e.g., prevent, reduce) the delivery of energy to a particular tissue region if, for example, the temperature or amount of reflected energy, exceeds a predetermined value. In some embodiments, the temperature monitoring systems are designed to alter (e.g., increase, reduce, sustain) the delivery of energy to a particular tissue region so as to maintain the tissue or energy delivery device at a preferred temperature or within a preferred temperature range.

In some embodiments, the systems further comprise an identification or tracking system configured, for example, to prevent the use of previously used components (e.g., non-sterile energy delivery devices), to identify the nature of a component of the system so the other components of the system may be appropriately adjusted for compatibility or optimized function. In some embodiments, the system reads a bar code or other information-conveying element associated with a component of the systems of the invention. In some embodiments, the connections between components of the system are altered (e.g., broken) following use so as to prevent additional uses. The present invention is not limited by the type of components used in the systems or the uses employed. Indeed, the devices may be configured in any desired manner. Likewise, the systems and devices may be used in any application where energy is to be delivered. Such uses include any and all medical, veterinary, and research applications. However, the systems and devices of the present invention may be used in agricultural settings, manufacturing settings, mechanical settings, or any other application where energy is to be delivered.

In some embodiments, the systems are configured for percutaneous, intravascular, intracardiac, laparoscopic, or surgical delivery of energy. Likewise, in some embodiments, the systems are configured for delivery of energy through a catheter, through a surgically developed opening, and/or through a body orifice (e.g., mouth, ear, nose, eyes, vagina, penis, anus) (e.g., a N.O.T.E.S. procedure). In some embodiments, the systems are configured for delivery of energy to a target tissue or region. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the brain, neck, chest, lung (e.g. peripheral lung), abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising: providing a tissue region and a system described herein (e.g., an energy delivery device, and at least one of the following components: a processor, a power supply, a means of directing, controlling and delivering power (e.g., a power splitter), a temperature monitor, an imager, a tuning system, a temperature reduction system, and/or a device placement system); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the heart, liver, genitalia, stomach, lung (e.g. periphery of the lung), large intestine, small intestine, brain, neck, bone, kidney, muscle, tendon, blood vessel, prostate, bladder, spinal cord, skin, veins, finger nails, and toe nails. In some embodiments, the processor receives information from sensors and monitors and controls the other components of the systems. In some embodiments, the energy output of the power supply is altered, as desired, for optimized therapy. In some embodiments, where more than one energy delivery component is provided, the amount of energy delivered to each of the delivery components is optimized to achieve the desired result. In some embodiments, the temperature of the system is monitored by a temperature sensor and, upon reaching or approaching a threshold level, is reduced by activation of the temperature reduction system. In some embodiments the imaging system provides information to the processor, which is displayed to a user of the system and may be used in a feedback loop to control the output of the system.

In some embodiments, energy is delivered to the tissue region in different intensities and from different locations within the device. For example, certain regions of the tissue region may be treated through one portion of the device, while other regions of the tissue may be treated through a different portion of the device. In addition, two or more regions of the device may simultaneously deliver energy to a particular tissue region so as to achieve constructive phase interference (e.g., wherein the emitted energy achieves a synergistic effect). In other embodiments, two or more regions of the device may deliver energy so as to achieve a destructive interference effect. In some embodiments, the method further provides additional devices for purposes of achieving constructive phase interference and/or destructive phase interference. In some embodiments, phase interference (e.g., constructive phase interference, destructive phase interference), between one or more devices, is controlled by a processor, a tuning element, a user, and/or a power splitter.

The systems, devices, and methods of the present invention may be used in conjunction with other systems, device, and methods. For example, the systems, devices, and methods of the present invention may be used with other ablation devices, other medical devices, diagnostic methods and reagents, imaging methods and reagents, device placement systems, and therapeutic methods and agents. Use may be concurrent or may occur before or after another intervention. The present invention contemplates the use systems, devices, and methods of the present invention in conjunction with any other medical interventions.

Additionally, integrated ablation and imaging systems are needed that provide feedback to a user and permit communication between various system components. System parameters may be adjusted during the ablation to optimize energy delivery. In addition, the user is able to more accurately determine when the procedure is successfully completed, reducing the likelihood of unsuccessful treatments and/or treatment related complications.

In certain embodiments, the present invention provides devices comprising an antenna configured for delivery of energy to a tissue, the antenna comprising one or more cooling tubes or channels within a coaxial cable, the tubes configured to deliver coolant to the antenna, wherein the coolant is a gas compressed at or near its critical point. In some embodiments, the coolant comprises the dielectric material of the coaxial cable. In some embodiments, the coolant channels comprises all or part of the dielectric space. The devices are not limited to a particular gas. In some embodiments, the gas is $CO_2$. In some embodiments, the one or more coolant tubes or channels are between an outer conductor and dielectric material of the coaxial cable. In some embodiments, the one or more coolant tubes or channels are between an inner conductor and dielectric material of the coaxial cable. In some embodiments, a porous dielectric material allows coolant to be flowed directly through the dielectric material. In some embodiments, the one or more coolant tubes or channels are within an inner or outer conductor. In some embodiments, the device has therein a proximal region, a central region, and a distal region. In some embodiments, the distal region is configured to deliver the energy to the tissue. In some embodiments, the proximal and/or central regions have therein the coolant tubes or channels. In some embodiments, the distal portion does not have the coolant tubes or channels.

In some embodiments, the device has therein one or more "stick" regions configured to facilitate adherence of the tissue onto the stick region, for example, to stabilize the device in a desired position during energy delivery. In some embodiments, the stick region is configured to attain and maintain a temperature causing freezing of the tissue to the stick region. In some embodiments, the stick region is positioned within the central region and/or the proximal region. The stick region is not limited to any particular temperature for facilitating adherence of a tissue region. In some embodiments, the stick region attains and maintains a temperature for facilitating adherence of a tissue region through contacting a region of the energy delivery device having circulated coolant. In some embodiments, the temperature of the stick region is maintained at temperature low enough such that adherence of a tissue region occurs upon contact with the stick region (e.g., such that a tissue region freezes onto the stick region). The stick region is not limited to a particular material composition. In some embodiments, the stick region is, for example, a metal material, a ceramic material, a plastic material, and/or any combination of such substances.

In some embodiments, the distal region and the central region are separated by a plug region designed to prevent cooling of the distal region. The plug region is not limited to a particular manner of preventing cooling of the distal region. In some embodiments, the plug region is designed to be in contact with a region having a reduced temperature (e.g., the central region of the energy delivery device having circulated coolant) without having its temperature reduced. In some embodiments, the material of the plug region is such that it is able to be in contact with a material having a low temperature without having its temperature substantially reduced (e.g., an insulating material). The plug region is not limited to a particular type of insulating material (e.g., a synthetic polymer (e.g., polystyrene, polyicynene, polyurethane, polyisocyanurate), aerogel, fibre-glass, cork). In some embodiments, a device having a plug region permits simultaneous exposure of a tissue to a cooled region (e.g., the region of the device proximal to the plug region) and an uncooled region (e.g., the region of the device distal to the plug region).

In certain embodiments, the present invention provides devices comprising an antenna configured for delivery of energy to a tissue, the antenna comprising one or more cooling tubes or channels within a coaxial cable, the coaxial cable having a dielectric region, the dielectric region having flexible and inflexible regions. In some embodiments, the flexible region is plastic, and the inflexible region is ceramic. In some embodiments, the inflexible region is positioned at the location of highest power emission.

In certain embodiments, the present invention provides devices comprising an antenna configured for delivery of energy to a tissue, the antenna comprising one or more cooling tubes or channels within a coaxial cable, the device having therein one or more pullwires connected to a pullwire anchor. In some embodiments, contraction of the one or more pullwires connected to the pullwire anchor reduces flexibility of the device. In some embodiments, the one or more pullwires are designed to bend at particular temperatures (e.g., super elastic nitinol wires).

In some embodiments, the present invention provides systems, devices, and methods for delivering energy (e.g. microwave energy) to a treatment site in a subject. In some embodiments, the present invention provides methods to deliver energy to difficult to access regions of a subject. In some embodiments, the present invention provides access to the peripheral lung through the bronchial tree. In some embodiments, the present invention provides access to lung nodules, tumors, and/or lesions on peripheral lung tissue (e.g. without incision into the lung) or without entry from the outside of the lung. In some embodiments, the present invention provides access to lung nodules, tumors, and/or lesions on peripheral lung tissue through the trachea and/or bronchial tree (e.g. primary, secondary, and tertiary bronchia, and bronchioles). In some embodiments, the present invention delivers energy (e.g. microwave energy) through the bronchial tree to the peripheral lung without damaging (e.g. without significantly damaging the tissue along the path).

BRIEF DESCRIPTION OF THE DRAWINGS

FIG. 2 shows various shapes of coaxial transmission lines and/or the dielectric elements in some embodiments of the present invention.

FIG. 4A and FIG. 4B display a coaxial transmission line embodiment having partitioned segments segregated by meltable walls containing first and second materials (e.g., materials configured to generate a temperature reducing chemical reaction upon mixing) preventing undesired device heating (e.g., heating along the outer conductor).

FIG. 6 shows a transverse cross-section schematic of coaxial cable embodiments having coolant passages.

FIG. 21 demonstrates cooling with an energy delivery device. A temperature profile during ablation measured 7 cm proximal to the tip of the antenna showed that cooling with chilled water can remove heating caused by more than 120 W input power (upper). A ~3 cm ablation created with the cooled antenna (125 W, 5 min) shows no "tail" along the antenna. The ceramic tube and faceted tip make percutaneous introduction possible (lower).

FIG. 25 shows the experimental setup (top) and results for temperatures measured along the antenna shaft while the antenna tip is maintained at 150° C. for 0, 13 and 23.8 stp L/min NC—$CO_2$ flow (bottom). Note that heating was only considered for thermal conduction from the antenna tip—no internal heating was considered in this test.

DETAILED DESCRIPTION

Figure 1:
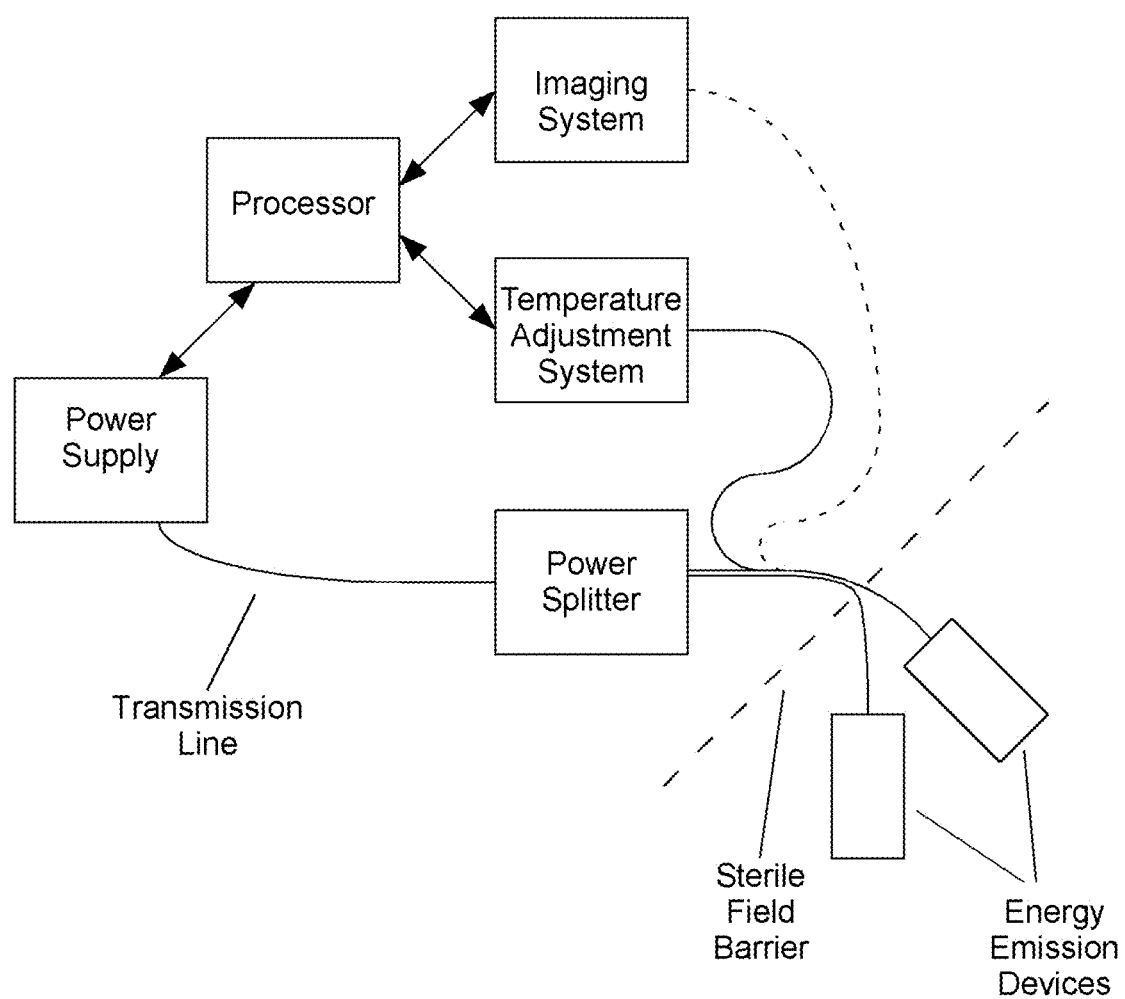
FIG. 1 shows a schematic view of an energy delivery system in an embodiment of the invention.

The present invention relates to comprehensive systems, devices and methods for delivering energy (e.g., microwave energy, radiofrequency energy) to tissue for a wide variety of applications, including medical procedures (e.g., tissue ablation (e.g. tumor ablation), resection, cautery, vascular thrombosis, intraluminal ablation of a hollow viscus, cardiac ablation for treatment of arrhythmias, electrosurgery, tissue harvest, cosmetic surgery, intraocular use, etc.). In some embodiments, the present invention provides systems for the delivery of microwave energy comprising a power supply, a means of directing, controlling and delivering power (e.g., a power splitter), a processor, an energy emitting device, a cooling system, an imaging system, a temperature monitoring system, a device placement system, and/or a tracking system. In particular, systems, devices, and methods are provided for treating a difficult to access tissue region (e.g., a peripheral lung tumor) through use of the energy delivery systems of the present invention.

The systems of the present invention may be combined within various system/kit embodiments. For example, the present invention provides systems comprising one or more of a generator, a power distribution system, a means of directing, controlling and delivering power (e.g., a power splitter), an energy applicator, device placement systems (e.g. multiple catheter system), along with any one or more accessory component (e.g., surgical instruments, software for assisting in procedure, processors, temperature monitoring devices, etc.). The present invention is not limited to any particular accessory component.

The systems of the present invention may be used in any medical procedure (e.g., percutaneous or surgical) involving delivery of energy (e.g., radiofrequency energy, microwave energy, laser, focused ultrasound, etc.) to a tissue region. The systems are not limited to treating a particular type or kind of tissue region (e.g., brain, liver, heart, blood vessels, foot, lung, bone, etc.). For example, the systems of the present invention find use in ablating tumor regions (e.g. lung tumors (e.g. peripheral lung tumors)). Additional treatments include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, primary or metastatic tumors or peripheral lung nodules. In some embodiments, the surgical application comprises the control of hemorrhage (e.g. electrocautery). In some embodiments, the surgical application comprises tissue cutting or removal. In some embodiments, the device is configured for movement and positioning, with minimal damage to the tissue or organism, at any desired location, including but not limited to, the brain, neck, chest, abdomen, pelvis, and extremities. In some embodiments, the device is configured for guided delivery, for example, by computerized tomography, ultrasound, magnetic resonance imaging, fluoroscopy, and the like.

In some embodiments, the present invention provides devices, systems, and methods for placing energy delivery devices in difficult to reach structures, tissue regions, and/or organs (e.g. a branched structure (e.g. human lungs). The power generation and distribution systems; means of directing, controlling and delivering power (e.g., a power splitter); energy applicators; and accessory components (e.g., surgical instruments, software for assisting in procedure, processors, temperature monitoring devices, etc.) described herein find use with systems (e.g. multiple catheter systems (e.g. primary catheter, channel catheter, and steerable navigation catheter)) for accurate placement of energy delivery devices in difficult to access tissue regions.

In some embodiments, the present invention provides devices, systems, and methods for reducing heat loss from devices delivering energy (e.g. microwave energy) to a tissue region of a subject, and/or to reduce undesired heating within and along an energy delivery device. In some embodiments, undesired heat loss form energy delivery devices and/or undesired heating within and along an energy delivery device compromises the efficiency of energy-delivery procedures, results in damage to tissues surrounding the target site and/or along the delivery path, and requires increased energy to achieve efficacious energy delivery at the target site. In some embodiments, reduces heating and/or heat loss through: insulator materials (e.g. porous insulators), coolant delivery along the energy delivery device, specialized cable configurations (e.g. one or more coolant channels, inflatable coolant channels, etc.), low-heat energy delivery programs (e.g. low energy, pulsed programs, etc.), and other suitable heat-loss-reduction and/or temperature-reduction devices, systems, and methods find use with the present invention.

The illustrated embodiments provided below describe the systems of the present invention in terms of medical applications (e.g., ablation of tissue through delivery of microwave energy). However, it should be appreciated that the systems of the present invention are not limited to medical applications. The systems may be used in any setting requiring delivery of energy to a load (e.g., agricultural settings, manufacture settings, research settings, etc.). The illustrated embodiments describe the systems of the present invention in terms of microwave energy. It should be appreciated that the systems of the present invention are not limited to a particular type of energy (e.g., radiofrequency energy, microwave energy, focused ultrasound energy, laser, plasma).

The systems of the present invention are not limited to any particular component or number of components. In some embodiments, the systems of the present invention include, but are not limited to including, a power supply, a means of directing, controlling and delivering power (e.g., a power splitter), a processor, an energy delivery device with an antenna, a cooling system, an imaging system, a device placement system, and/or a tracking system. When multiple antennas are in use, the system may be used to individually control each antenna separately.

FIG. 1 shows an exemplary system of the invention. As shown, the energy delivery system comprises a power supply, a transmission line, a power distribution component (e.g., power splitter), a processor, an imaging system, a temperature monitoring system and an energy delivery device. In some embodiments, as shown, the components of the energy delivery systems are connected via a transmission line, cables, etc. In some embodiments, the energy delivery device is separated from the power supply, a means of directing, controlling and delivering power (e.g., a power splitter), processor, imaging system, temperature monitoring system across a sterile field barrier.

Exemplary components of the energy delivery systems are described in more detail in the following sections: I. Power Supply; II. Energy delivery devices; III. Processor; IV. Imaging Systems; V. Tuning Systems; VI. Temperature Adjustment Systems; VII. Identification Systems; VIII. Temperature Monitoring Devices; IX. Procedure Device Hubs; X. Uses, and XI. Device Placement Systems.

I. Power Supply

The energy utilized within the energy delivery systems of the present invention is supplied through a power supply. The present invention is not limited to a particular type or kind of power supply. In some embodiments, the power supply is configured to provide energy to one or more components of the energy delivery systems of the present invention (e.g., ablation devices). The power supply is not limited to providing a particular type of energy (e.g., radiofrequency energy, microwave energy, radiation energy, laser, focused ultrasound, etc.). The power supply is not limited to providing particular amounts of energy or at a particular rate of delivery. In some embodiments, the power supply is configured to provide energy to an energy delivery device for purposes of tissue ablation.

The present invention is not limited to a particular type of power supply. In some embodiments, the power supply is configured to provide any desired type of energy (e.g., microwave energy, radiofrequency energy, radiation, cryo energy, electroporation, high intensity focused ultrasound, and/or mixtures thereof). In some embodiments, the type of energy provided with the power supply is microwave energy. In some some embodiments, the power supply provides microwave energy to ablation devices for purposes of tissue ablation. The use of microwave energy in the ablation of tissue has numerous advantages. For example, microwaves have a broad field of power density (e.g., approximately 2 cm surrounding an antenna depending on the wavelength of the applied energy) with a correspondingly large zone of active heating, thereby allowing uniform tissue ablation both within a targeted zone and in perivascular regions (see, e.g., International Publication No. WO 2006/004585; herein incorporated by reference in its entirety). In addition, microwave energy has the ability to ablate large or multiple zones of tissue using multiple probes with more rapid tissue heating. Microwave energy has an ability to penetrate tissue to create deep lesions with less surface heating. Energy delivery times are shorter than with radiofrequency energy and probes can heat tissue sufficiently to create an even and symmetrical lesion of predictable and controllable depth. Microwave energy is generally safe when used near vessels. Also, microwaves do not rely on electrical conduction as it radiates through tissue, fluid/blood, as well as air. Therefore, microwave energy can be used in tissue, lumens, lungs, and intravascularly.

In some embodiments, the power supply is an energy generator. In some embodiments, the generator is configured to provide as much as 100 watts of microwave power of a frequency of from 915 MHz to 5.8 GHz, although the present invention is not so limited. In some embodiments, a conventional magnetron of the type commonly used in microwave ovens is chosen as the generator. In some embodiments, a single-magnetron based generator (e.g., with an ability to output 300 W through a single channel, or split into multiple channels) is utilized. It should be appreciated, however, that any other suitable microwave power source can substituted in its place. In some embodiments, the types of generators include, but are not limited to, those available from Cober-Muegge, LLC, Norwalk, Conn., USA, Sairem generators, and Gerling Applied Engineering generators. In some embodiments, the generator has at least approximately 60 Watts available (e.g., 50, 55, 56, 57, 58, 59, 60, 61, 62, 65, 70, 100, 500, 1000 Watts). For a higher-power operation, the generator is able to provide approximately 300 Watts (e.g., 200 Watts, 280, 290, 300, 310, 320, 350, 400, 750 Watts). In some embodiments, wherein multiple antennas are used, the generator is able to provide as much energy as necessary (e.g., 400 Watts, 500, 750, 1000, 2000, 10,000 Watts). In some embodiments, the generator comprises solid state amplifier modules which can be operated separately and phase-controlled. In some embodiments, generator outputs are combined constructively to increase total output power. In some embodiments, the power supply distributes energy (e.g., collected from a generator) with a power distribution system. The present invention is not limited to a particular power distribution system. In some embodiments, the power distribution system is configured to provide energy to an energy delivery device (e.g., a tissue ablation catheter) for purposes of tissue ablation. The power distribution system is not limited to a particular manner of collecting energy from, for example, a generator. The power distribution system is not limited to a particular manner of providing energy to ablation devices. In some embodiments, the power distribution system is con-figured to transform the characteristic impedance of the generator such that it matches the characteristic impedance of an energy delivery device (e.g., a tissue ablation catheter).

In some embodiments, the power distribution system is configured with a variable power splitter so as to provide varying energy levels to different regions of an energy delivery device or to different energy delivery devices (e.g., a tissue ablation catheter). In some embodiments, the power splitter is provided as a separate component of the system. In some embodiments, the power splitter is used to feed multiple energy delivery devices with separate energy signals. In some embodiments, the power splitter electrically isolates the energy delivered to each energy delivery device so that, for example, if one of the devices experiences an increased load as a result of increased temperature deflection, the energy delivered to that unit is altered (e.g., reduced, stopped) while the energy delivered to alternate devices is unchanged. The present invention is not limited to a particular type or kind of power splitter. In some embodiments, the power splitter is designed by SM Electronics. In some embodiments, the power splitter is configured to receive energy from a power generator and provide energy to additional system components (e.g., energy delivery devices). In some embodiments the power splitter is able to connect with one or more additional system components (e.g., 1, 2, 3, 4, 5, 7, 10, 15, 20, 25, 50, 100, 500 . . . ). In some embodiments, the power splitter is configured to deliver variable amounts of energy to different regions within an energy delivery device for purposes of delivering variable amounts of energy from different regions of the device. In some embodiments, the power splitter is used to provide variable amounts of energy to multiple energy delivery devices for purposes of treating a tissue region. In some embodiments, the power splitter is configured to operate within a system comprising a processor, an energy delivery device, a temperature adjustment system, a power splitter, a tuning system, and/or an imaging system. In some embodiments, the power splitter is able to handle maximum generator outputs plus, for example, 25% (e.g., 20%, 30%, 50%). In some embodiments, the power splitter is a 1000-watt-rated 2-4 channel power splitter.

In some embodiments, where multiple antennas are employed, the system of the present invention may be configured to run them simultaneously or sequentially (e.g., with switching). In some embodiments, the system is configured to phase the fields for constructive or destructive interference. Phasing may also be applied to different elements within a single antenna. In some embodiments, switching is combined with phasing such that multiple antennas are simultaneously active, phase controlled, and then switched to a new set of antennas (e.g., switching does not need to be fully sequential). In some embodiments, phase control is achieved precisely. In some embodiments, phase is adjusted continuously so as to move the areas of constructive or destructive interference in space and time. In some embodiments, the phase is adjusted randomly. In some embodiments, random phase adjustment is performed by mechanical and/or magnetic interference.

II. Energy Delivery Devices

The energy delivery systems of the present invention contemplate the use of any type of device configured to deliver (e.g., emit) energy (e.g., ablation device, surgical device, etc.) (see, e.g., U.S. Pat. Nos. 7,101,369, 7,033,352, 6,893,436, 6,878,147, 6,823,218, 6,817,999, 6,635,055, 6,471,696, 6,383,182, 6,312,427, 6,287,302, 6,277,113, 6,251,128, 6,245,062, 6,026,331, 6,016,811, 5,810,803, 5,800,494, 5,788,692, 5,405,346, 4,494,539, U.S. patent application Ser. Nos. 11/728,460, 11/728,457, 11/728,428, 11/237,136, 11/236,985, 10/980,699, 10/961,994, 10/961, 761, 10/834,802, 10/370,179, 09/847,181; Great Britain Patent Application Nos. 2,406,521, 2,388,039; European Patent No. 1395190; and International Patent Application Nos. WO 06/008481, WO 06/002943, WO 05/034783, WO 04/112628, WO 04/033039, WO 04/026122, WO 03/088858, WO 03/039385 WO 95/04385; each herein incorporated by reference in their entireties). Such devices include any and all medical, veterinary, and research applications devices configured for energy emission, as well as devices used in agricultural settings, manufacturing settings, mechanical settings, or any other application where energy is to be delivered.

In some embodiments, the systems utilize energy delivery devices having therein antennae configured to emit energy (e.g., microwave energy, radiofrequency energy, radiation energy). The systems are not limited to particular types or designs of antennae (e.g., ablation device, surgical device, etc.). In some embodiments, the systems utilize energy delivery devices having linearly shaped antennae (see, e.g., U.S. Pat. Nos. 6,878,147, 4,494,539, U.S. patent application Ser. Nos. 11/728,460, 11/728,457, 11/728,428, 10/961,994, 10/961,761; and International Patent Application No., WO 03/039385; each herein incorporated by reference in their entireties). In some embodiments, the systems utilize energy delivery devices having non-linearly shaped antennae (see, e.g., U.S. Pat. Nos. 6,251,128, 6,016,811, and 5,800,494, U.S. patent application Ser. No. 09/847,181, and International Patent Application No. WO 03/088858; each herein incorporated by reference in their entireties). In some embodiments, the antennae have horn reflection components (see, e.g., U.S. Pat. Nos. 6,527,768, 6,287,302; each herein incorporated by reference in their entireties). In some embodiments, the antenna has a directional reflection shield (see, e.g., U.S. Pat. No. 6,312,427; herein incorporated by reference in its entirety). In some embodiments, the antenna has therein a securing component so as to secure the energy delivery device within a particular tissue region (see, e.g., U.S. Pat. Nos. 6,364,876, and 5,741,249; each herein incorporated by reference in their entireties).

In some embodiments, antennae configured to emit energy comprise coaxial transmission lines. The devices are not limited to particular configurations of coaxial transmission lines. Examples of coaxial transmission lines include, but are not limited to, coaxial transmission lines developed by Pasternack, Micro-coax, and SRC Cables. In some embodiments, the coaxial transmission line has a center conductor, a dielectric element, and an outer conductor (e.g., outer shield). In some embodiments, the systems utilize antennae having flexible coaxial transmission lines (e.g., for purposes of positioning around, for example, pulmonary veins or through tubular structures) (see, e.g., U.S. Pat. Nos. 7,033,352, 6,893,436, 6,817,999, 6,251,128, 5,810,803, 5,800,494; each herein incorporated by reference in their entireties). In some embodiments, the systems utilize antennae having rigid coaxial transmission lines (see, e.g., U.S. Pat. No. 6,878,147, U.S. patent application Ser. Nos. 10/961, 994, 10/961,761, and International Patent Application No. WO 03/039385; each herein incorporated by reference in their entireties).

Figure 16:
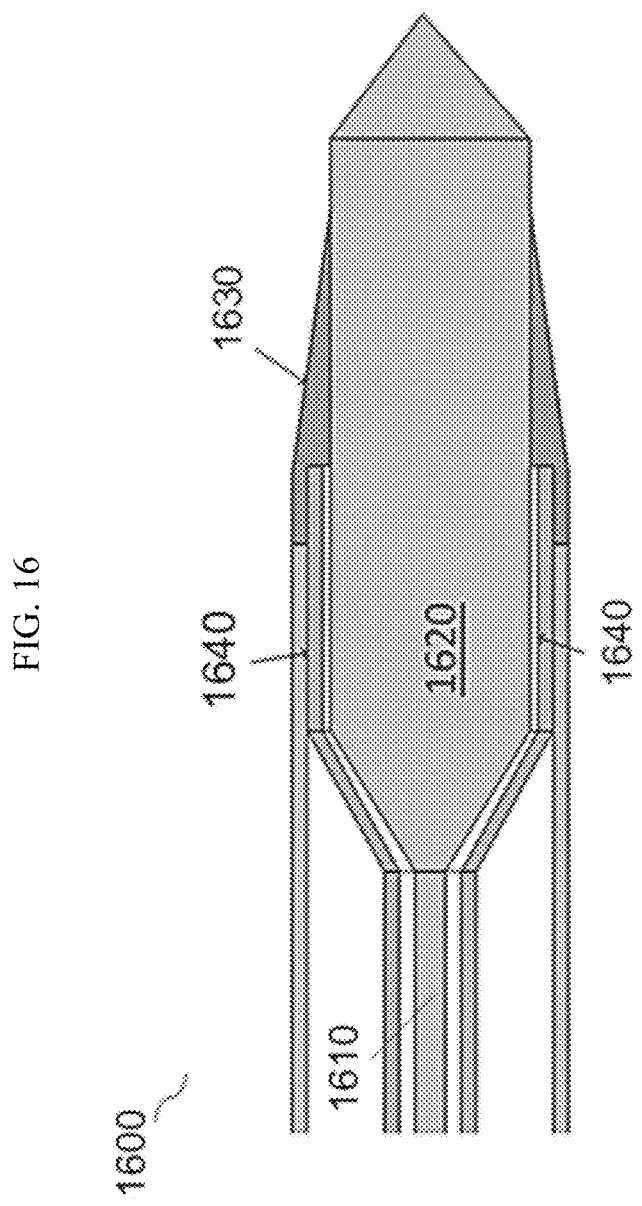
FIG. 16 shows an energy delivery device having a narrow coaxial transmission line connected with a larger coaxial transmission line positioned within an antenna, which is connected with an inner conductor.

In some embodiments, the energy delivery devices have a coaxial transmission line positioned within the antenna, and a coaxial transmission line connecting with the antenna. In some embodiments, the size of the coaxial transmission line within the antenna is larger than the coaxial transmission line connected with the antenna. The coaxial transmission line within the antenna and the coaxial transmission line connecting with the antenna are not limited to particular sizes. For example, in some embodiments, whereas the coaxial transmission line connected with the antenna is approximately 0.032 inches, the size of the coaxial transmission line within the antenna is larger than 0.032 inches (e.g., 0.05 inches, 0.075 inches, 0.1 inches, 0.5 inches). In some embodiments, the coaxial transmission line within the antenna has an inner conductor that is stiff and thick. In some embodiments, the end of the coaxial transmission line within the antenna is sharpened for percutaneous use. In some embodiments, the dielectric coating of the coaxial transmission line within the antenna is PTFE (e.g., for purposes of smoothing transitions from a cannula to an inner conductor (e.g., a thin and sharp inner conductor)). FIG. 16 shows an energy delivery device 1600 having a narrow coaxial transmission line 1610 connected with a larger coaxial transmission line 1620 positioned within an antenna 1630, which is connected with an inner conductor 1640.

The present invention is not limited to a particular coaxial transmission line shape. Indeed, in some embodiments, the shape of the coaxial transmission line and/or the dielectric element is selected and/or adjustable to fit a particular need. FIG. 2 shows some of the various, non-limiting shapes the coaxial transmission line and/or the dielectric element may assume.

In some embodiments, the outer conductor is a 20-gauge needle or a component of similar diameter to a 20-gauge needle. Preferably, for percutaneous use, the outer conductor is not larger than a 17-gauge needle (e.g., no larger than a 16-gauge needle). In some embodiments, the outer conductor is a 17-gauge needle. However, in some embodiments, larger devices are used, as desired. For example, in some embodiments, a 12-gauge diameter is used. The present invention is not limited by the size of the outer conductor. In some embodiments, the outer conductor is configured to fit within series of larger needles for purposes of assisting in medical procedures (e.g., assisting in tissue biopsy) (see, e.g., U.S. Pat. Nos. 6,652,520, 6,582,486, 6,355,033, 6,306, 132; each herein incorporated by reference in their entireties). In some embodiments, the center conductor is configured to extend beyond the outer conductor for purposes of delivering energy to a desired location. In some embodiments, some or all of the feedline characteristic impedance is optimized for minimum power dissipation, irrespective of the type of antenna that terminates at its distal end.

In some embodiments, the energy delivery devices have a triaxial transmission line. In some embodiments, the present invention provides a triaxial microwave probe design where the outer conductor allows improved tuning of the antenna to reduce reflected energy through the transmission line. This improved tuning reduces heating of the transmission line allowing more power to be applied to the tissue and/or a smaller transmission line (e.g. narrower) to be used. Further, the outer conductor may slide with respect to the inner conductors to permit adjustment of the tuning to correct for effects of the tissue on the tuning. In some embodiments, and outer conductor is stationary with respect to the inner conductors. In some embodiments, the present invention provides a probe having a first conductor and a tubular second conductor coaxially around the first conductor but insulated therefrom (e.g. insulated by a dielectric material and/or coolant). A tubular third conductor is fit coaxially around the first and second conductors. The first conductor may extend beyond the second conductor into tissue when a proximal end of the probe is inserted into a body. The second conductor may extend beyond the third conductor into the tissue to provide improved tuning of the probe limiting power dissipated in the probe outside of the exposed portions of the first and second conductors. The third tubular conductor may be a channel catheter for insertion into the body or may be separate from a channel catheter. In some embodiments, a device comprising first, second, and third conductors is sufficiently flexible to navigate a winding path (e.g. through a branched structure within a subject (e.g. through the brachial tree)). In some embodiments, the first and second conductors may fit slidably within the third conductor. In some embodiments, the present invention provides a probe that facilitates tuning of the probe in tissue by sliding the first and second conductors inside of the third conductor. In some embodiments, the probe includes a lock attached to the third conductor to adjustably lock a sliding location of the first and second conductors with respect to the third conductor. In some embodiments, the present invention provides a triaxial transmission line, as described in U.S. Pat. No. 7,101,369, U.S. Pat. App. No. 2007/0016180, U.S. Pat. App. No. 2008/0033424, U.S. Pat. App. No. 20100045558, U.S. Pat. App. No. 20100045559, herein incorporated by reference in their entireties.

Figure 32:
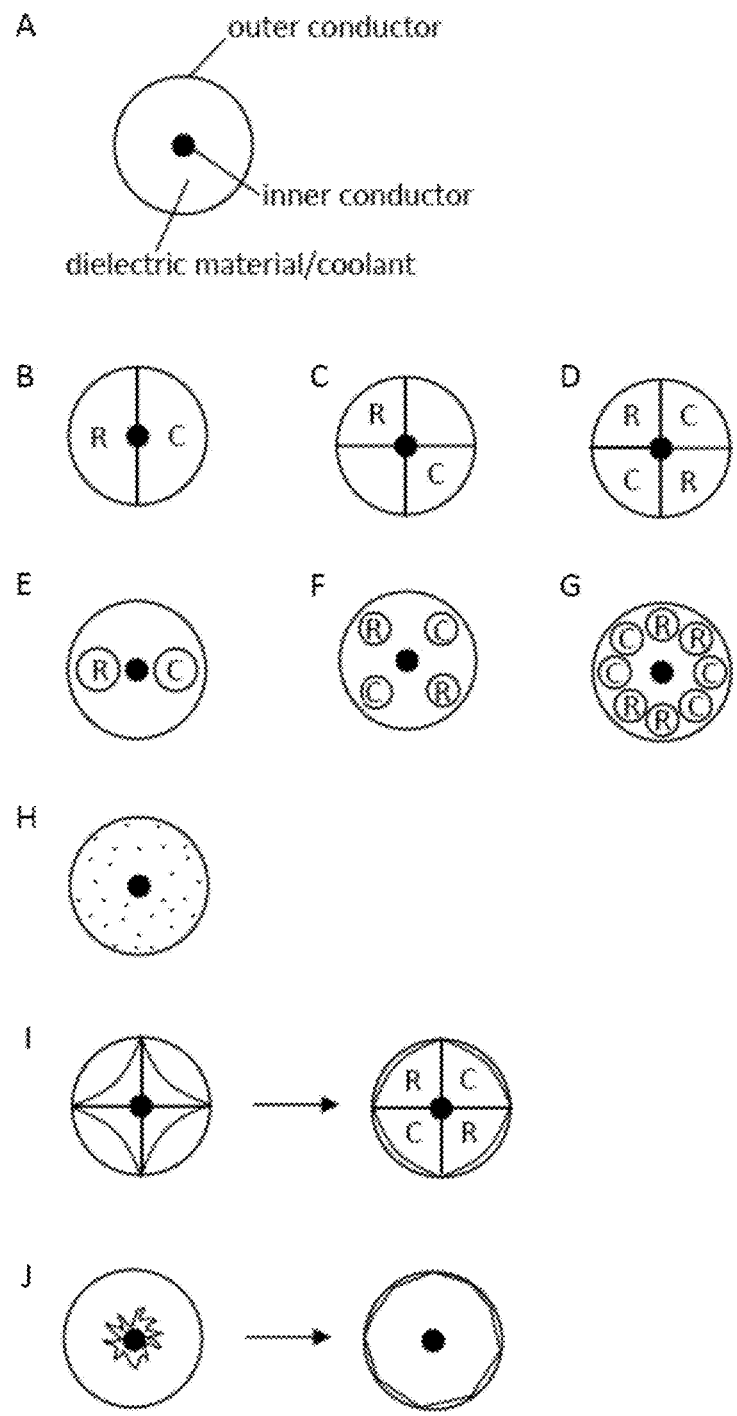
FIG. 32A-J shows a variety of exemplary configurations for using the dielectric material of coaxial transmission lines as coolant: a) conventional coaxial configuration; b) the dielectric space is divided into one coolant channel and one return channel; c) the dielectric space is divided into for chambers, one coolant channel, one return channel, and two non-flow channels; d) the dielectric space is divided into for chambers, two coolant channels and two return channels; e) one coolant channel and one return channel within the dielectric space; f) two coolant channels and two return channels within the dielectric space; g) four coolant channels and four return channels within the dielectric space; h) porous dielectric material allows coolant to flow through the dielectric material; i) the dielectric space is divided into four chambers, flow of coolant into the chambers expands the collapsible channels, increasing the cross-sectional profile of the channels; and j) a collapsible channel adopts a collapsed conformation, reducing its cross-sectional profile in the absence of coolant flow, coolant flow expands the coolant channel, increasing the cross-sectional profile of the channel ("C" and "R" designate potential coolant (C) and return (R) channels.

In some embodiments, one or more components of a coaxial transmission line or triaxial transmission line comprise a flexible and/or collapsible material (e.g. biaxially-oriented polyethylene terephthalate (boPET) (e.g. MYLAR, MELINEX, HOSTAPHAN, etc.), etc.). In some embodiments, the outer conductor of the coaxial transmission line (or second (middle) conductor of a triaxial transmission line) comprises a flexible and/or collapsible material (e.g. boPET). In some embodiments, a component of a coaxial transmission line (e.g. outer conductor) comprises boPET coated in one or more films to provide desired characteristics (e.g. electric conductivity, heat insulation, etc.). In some embodiments, a collapsible outer conductor allows the transmission line to adopt variable cross-sectional profile (e.g. variable diameter, variable shape, etc.) (SEE, e.g., FIGS. 32I and 32J). In some embodiments, a collapsible outer conductor encircles the inner conductor. In some embodiments, a collapsible outer conductor forms a closed sack around the inner conductor. In some embodiments, fluid (e.g. dielectric material, and/or coolant) can be flowed through the collapsible outer conductor to adjust its variable cross-sectional profile. In some embodiments, a collapsible outer conductor adopts a collapsed conformation when fluid is withdrawn from the area within the outer conductor, thereby decreasing the pressure within the outer conductor. In some embodiments, in a collapsed conformation the outer conductor displays a minimized cross-sectional profile (SEE, e.g., FIGS. 32I and 32J). In some embodiments, in a collapsed conformation the outer conductor closely hugs the periphery of the inner conductor (SEE 32J). In some embodiments, the collapsed conformation provides decreased cross-sectional profile and/or increased flexibility to aid in insertion, placement, and/or withdrawal of the coaxial transmission line. In some embodiments, a collapsible outer conductor adopts an expanded conformation when fluid is flowed into the area within the outer conductor, thereby increasing the pressure within the outer conductor. In some embodiments, in an expanded conformation the outer conductor displays a maximized cross-sectional profile. In some embodiments, in an expanded conformation the distance between the inner conductor and the outer conductor is maximized. In some embodiments, the expanded conformation provides increased cross-sectional profile and/or optimized conduction to aid in energy delivery along the coaxial transmission line. In some embodiments, the expanded conformation provides an increased volume of coolant along the coaxial transmission line. In some embodiments, the collapsible outer conductor adopts any suitable shape in the expanded conformation. In some embodiments, the coaxial transmission line runs through a lumen, the shape of which dictates the expanded shape of the collapsible outer conductor. In some embodiments, the collapsible outer conductor adopts any suitable shape in the collapsed conformation. In some embodiments, the shape or configuration of the dielectric material dictates the collapsed shape of the collapsible outer conductor. In some embodiments, a collapsible outer conductor also comprises a coolant sheath, as described herein.

Figure 33:
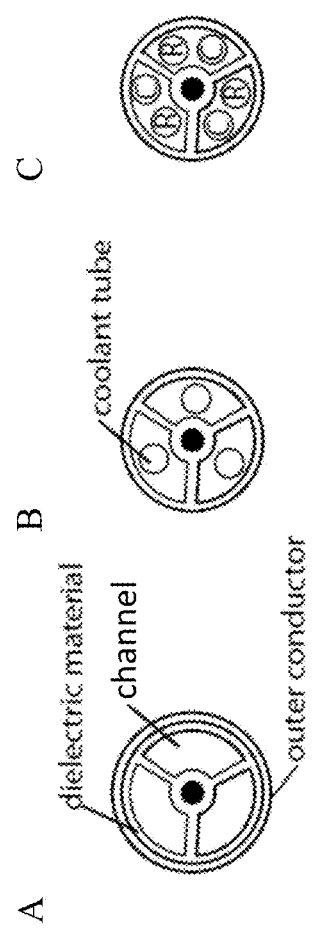
FIG. 33A-C shows exemplary "wagon wheel" cross-sections of coaxial transmission lines in which the dielectric material divides the space between the inner and outer conductors in channels.
Figure 34:
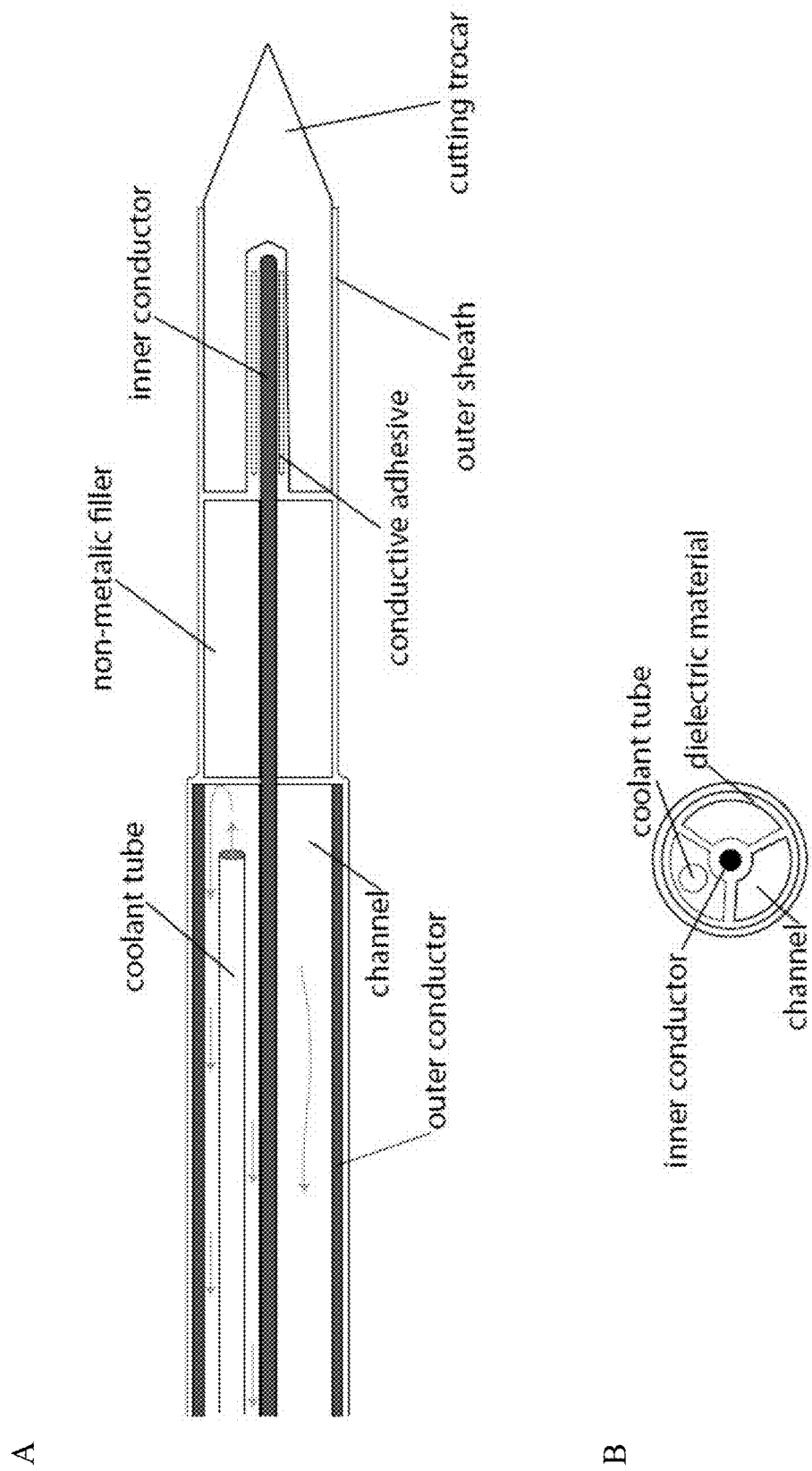
FIG. 34A-B shows an exemplary "wagon wheel" transmission line mounted with an outer sheath and cutting trocar; coolant flow through the coolant tube and channel is indicated.

In some embodiments, the dielectric material is shaped to provide to provide channels within the dielectric space (e.g. air channels, coolant channels, vacant channels, etc.) (SEE FIG. 33). In some embodiments, channels are completely or partially encompassed by the dielectric material. In some embodiments, the dielectric material divides the dielectric space into channels to create a "wagon wheel" conformation (SEE FIGS. 33 and 34). In some embodiments, the dielectric material divides the dielectric space (e.g. the space between the inner and outer conductors) into 1 or more channels (e.g. 1, 2, 3, 4, 5, 6, 7, 8, 9, 10, or more channels). In some embodiments, the channels within the dielectric space serve as coolant channels. In some embodiments, the channels within the dielectric space house coolant tubes. In some embodiments, a coolant tube within a channel delivers coolant along the transmission line, and a coolant channel provides the return path, to the proximal end of the transmission line (SEE, e.g., FIG. 34). In some embodiments, a channel comprises multiple coolant tubes (e.g. coolant and return). In some embodiment, channels formed by the dielectric material comprise a non-metallic filler. In some embodiments, non-metallic filler resides in the channels in the distal region of the transmission line (e.g. beyond the end of the outer conductor).

In some embodiments, the energy delivery devices are provided with a proximal portion and a distal portion, wherein the distal portion is detachable and provided in a variety of different configurations that can attach to a core proximal portion. For example, in some embodiments, the proximal portion comprises a handle and an interface to other components of the system (e.g., power supply) and the distal portion comprises a detachable antenna having desired properties. A plurality of different antenna configured for different uses may be provided and attached to the handle unit for the appropriate indication.

In some embodiments, multiple (e.g., more than 1) (e.g., 2, 3, 4, 5, 10, 20, etc.) coaxial transmission lines and/or triaxial transmission lines are positioned within each energy delivery device for purposes of delivery high amounts of energy over an extended period of time. In experiments conducted during the course of developing embodiments for the present invention, it was determined that an energy delivery device having three lower power coaxial transmission lines (e.g., positioned within the same probe) (e.g., within a 13 gauge needle) was able to deliver higher amounts of energy for a longer period of time than an energy delivery device having a higher power coaxial transmission line.

In some embodiments, the device is configured to attach with a detachable handle. The present invention is not limited to a particular type of detachable handle. In some embodiments, the detachable handle is configured to connect with multiple devices (e.g., 1, 2, 3, 4, 5, 10, 20, 50 . . . ) for purposes of controlling the energy delivery through such devices. In some embodiments, the handle is designed with a power amplifier for providing power to an energy delivery device.

In some embodiments, the device is designed to physically surround a particular tissue region for purposes of energy delivery (e.g., the device may be flexibly shaped around a particular tissue region). For example, in some embodiments, the device may be flexibly shaped around a blood vessel (e.g., pulmonary vein) for purposes of delivering energy to a precise region within the tissue.

Figure 14:
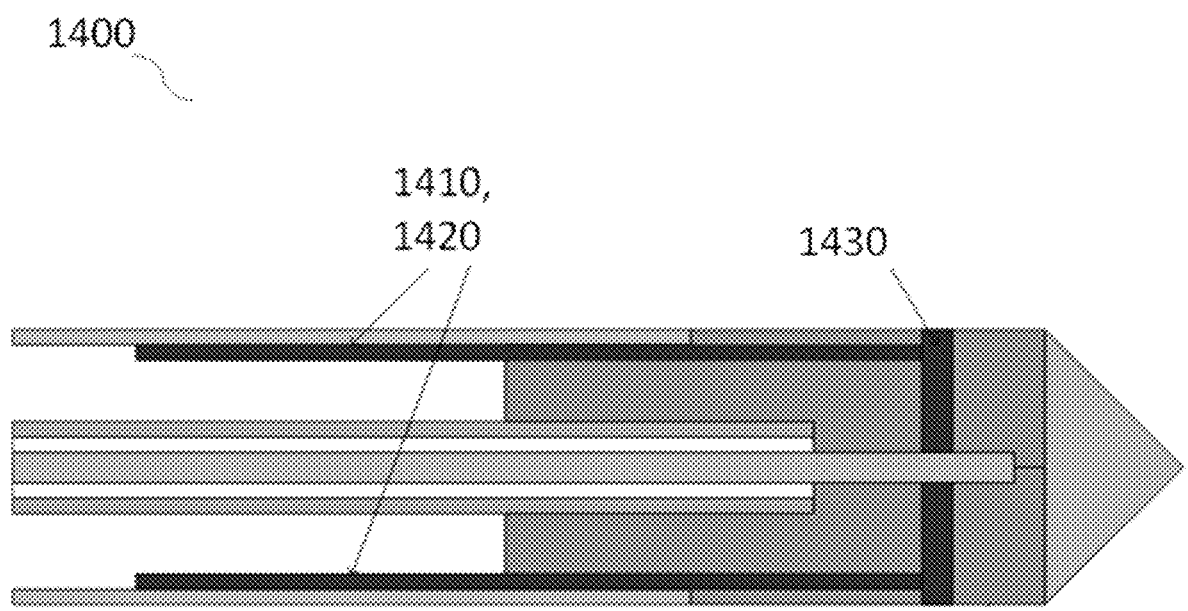
FIG. 14 shows an energy delivery device having two pullwires connected with a pullwire anchor.

In some embodiments, the energy delivery devices are configured for shape retention upon exposure to a compressive force. The energy delivery devices are not limited to a particular configuration for retaining shape upon exposure to a compressive force. In some embodiments, the energy delivery devices have therein a pullwire system for purposes of shape retention upon compression. The present invention is not limited to a particular type of pullwire system. In some embodiments, the pullwire system comprises one or more pullwires (e.g., 1 pullwire, 2 pullwires, 5 pullwires, 10 pullwires, 50 pullwires) connected with a pullwire anchor. In some embodiments, contraction (e.g., pushing, pulling) of the one or more pullwires connected to the pullwire anchor (e.g., contraction by a user) results in the assumption of an inflexible state by the energy delivery device such that upon exposure to a compressive force the energy delivery device retains its shape. In some embodiments, the pullwires can be locked in a contracted position. In some embodiments, the energy delivery devices having one or more pullwires connected with a pullwire anchor retains flexibility in the absence pullwire contraction. FIG. 14 shows an energy delivery device 1400 having two pullwires 1410, 1420 connected with a pullwire anchor 1430. In some embodiments, the energy delivery devices have three or more pullwires arranged in a symmetrical pattern which are pre-stressed thereby providing a constant inflexible shape. In some embodiments, the pullwires are configured to automatically contract in response to a stimulation (e.g., an electrical stimulation, a compressive stimulation) (e.g., muscle wires). In some embodiments, the pullwires are configured to provide a balancing force in response to a compressive force (e.g., a counteracting force). In some embodiments, the pullwires are designed to bend at particular temperatures (e.g., super elastic nitinol wires). In some embodiments, the bending of pullwires at particular temperatures is a detectable event that can be used to monitor the status of a procedure.

Figure 15:
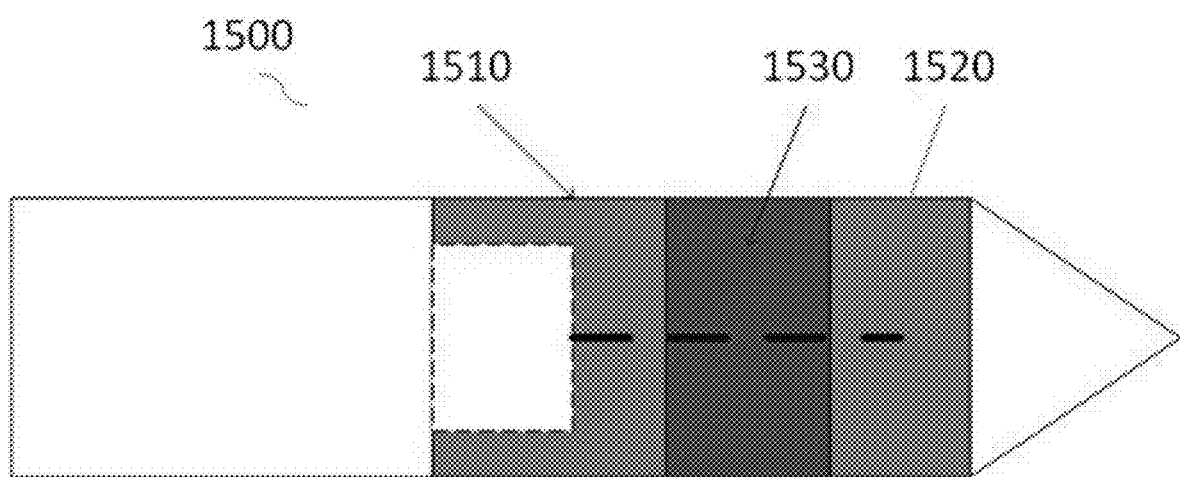
FIG. 15 shows an external perspective of an energy delivery device having inflexible regions and a flexible region.
Figure 17:
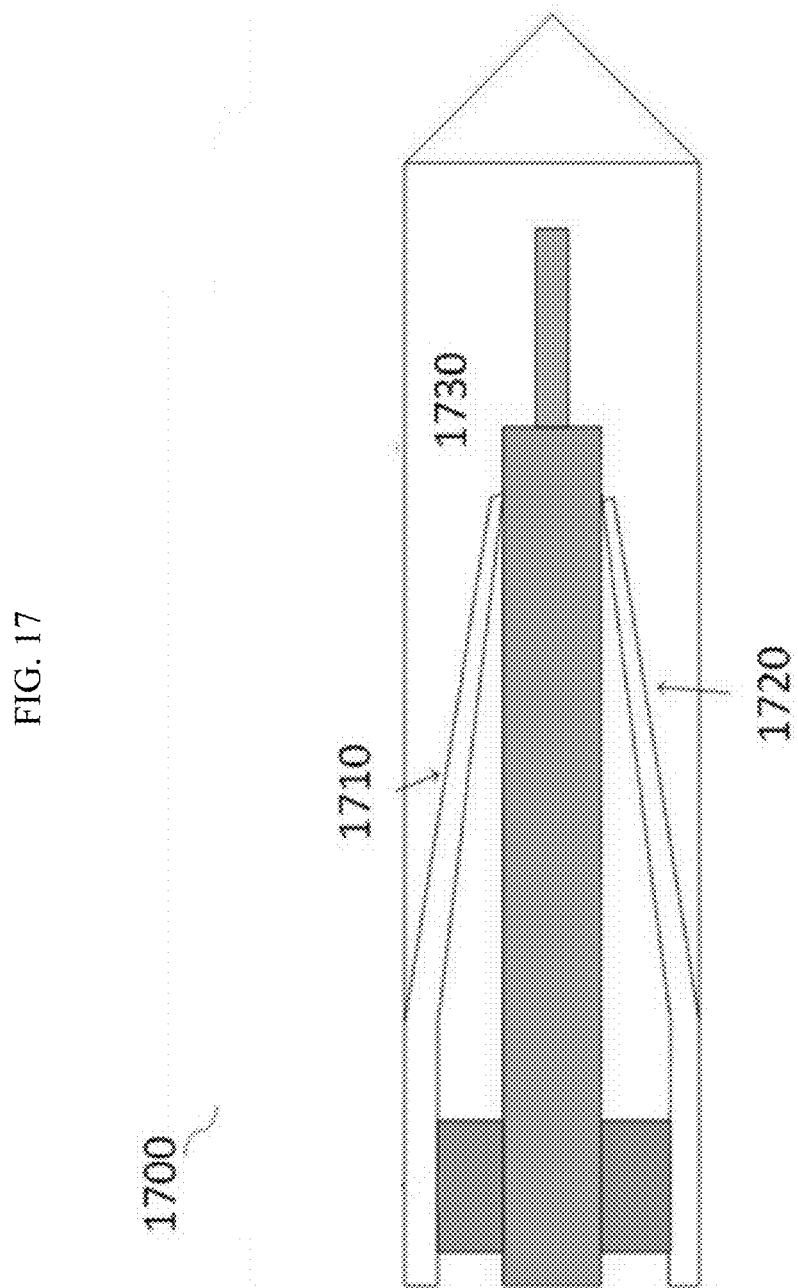
FIG. 17 shows a cross section of an energy delivery device having inflexible regions and a flexible region.

In some embodiments, the energy delivery devices are configured to have both flexible and inflexible regions. The energy delivery devices are not limited to particular configurations for having both flexible and inflexible regions. In some embodiments, the flexible regions comprise plastic (e.g., PEEK). In some embodiments, the inflexible regions comprise ceramic. The flexible and inflexible regions are not limited to particular positions within the energy delivery devices. In some embodiments, the flexible region is positioned in a region experiencing lower amounts of microwave field emission. In some embodiments, the inflexible region is positioned in a region experiencing high amounts of microwave field emission (e.g., located over the proximal portion of the antenna to provide dielectric strength and mechanical rigidity). FIG. 15 shows an external perspective of an energy delivery device 1500 having inflexible regions 1510 and 1520 (e.g., ceramic), and a flexible region 1530 (e.g., PEEK). FIG. 17 shows a cross section of an energy delivery device 1700 having inflexible regions 1710 and 1720, and a flexible region 1730. As shown, the inflexible regions 1710 and 1720 are gradually tapered so as to, for example, provide a larger surface area for bonding with the cannula, and so as to, for example, distribute stresses from bending forces over a larger surface area. As shown, the flexible region 1730 is positioned on the outside of the joint for purposes of improving strength due to its large diameter size. In some embodiments, the gradual taper of the inflexible regions are filled with a bonding material to provide additional strength. In some embodiments, the energy delivery devices have a heat shrink over the distal portion (e.g., the antenna) for providing additional durability.

In some embodiments, the material of the antenna is durable and provides a high dielectric constant. In some embodiments, the material of the antenna is zirconium and/or a functional equivalent of zirconium. In some embodiments, the energy delivery device is provided as two or more separate antenna attached to the same or different power supplies. In some embodiments, the different antennas are attached to the same handle, while in other embodiments different handles are provided for each antenna. In some embodiments, multiple antennae are used within a patient simultaneously or in series (e.g., switching) to deliver energy of a desired intensity and geometry within the patient. In some embodiments, the antennas are individually controllable. In some embodiments, the multiple antennas may be operated by a single user, by a computer, or by multiple users.

In some embodiments, the energy delivery devices are designed to operate within a sterile field. The present invention is not limited to a particular sterile field setting. In some embodiments, the sterile field includes a region surrounding a subject (e.g., an operating table). In some embodiments, the sterile field includes any region permitting access only to sterilized items (e.g., sterilized devices, sterilized accessory agents, sterilized body parts). In some embodiments, the sterile field includes any region vulnerable to pathogen infection. In some embodiments, the sterile field has therein a sterile field barrier establishing a barrier between a sterile field and a non-sterile field. The present invention is not limited to a particular sterile field barrier. In some embodiments, the sterile field barrier is the drapes surrounding a subject undergoing a procedure involving the systems of the present invention (e.g., tissue ablation). In some embodiments, a room is sterile and provides the sterile field. In some embodiments, the sterile field barrier is established by a user of the systems of the present invention (e.g., a physician). In some embodiments, the sterile field barrier hinders entry of non-sterile items into the sterile field. In some embodiments, the energy delivery device is provided in the sterile field, while one or more other components of the system (e.g., the power supply) are not contained in the sterile field.

In some embodiments, the energy delivery devices have therein protection sensors designed to prevent undesired use of the energy delivery devices. The energy delivery devices are not limited to a particular type or kind of protection sensors. In some embodiments, the energy delivery devices have therein a temperature sensor designed to measure the temperature of, for example, the energy delivery device and/or the tissue contacting the energy delivery device. In some embodiments, as a temperature reaches a certain level the sensor communicates a warning to a user via, for example, the processor. In some embodiments, the energy delivery devices have therein a skin contact sensor designed to detect contact of the energy delivery device with skin (e.g., an exterior surface of the skin). In some embodiments, upon contact with undesired skin, the skin contact sensor communicates a warning to a user via, for example, the processor. In some embodiments, the energy delivery devices have therein an air contact sensor designed to detect contact of the energy delivery device with ambient air (e.g., detection through measurement of reflective power of electricity passing through the device). In some embodiments, upon contact with undesired air, the skin contact sensor communicates a warning to a user via, for example, the processor. In some embodiments, the sensors are designed to prevent use of the energy delivery device (e.g., by automatically reducing or preventing power delivery) upon detection of an undesired occurrence (e.g., contact with skin, contact with air, undesired temperature increase/descrease). In some embodiments, the sensors communicate with the processor such that the processor displays a notification (e.g., a green light) in the absence of an undesired occurrence. In some embodiments, the sensors communicate with the processor such that the processor displays a notification (e.g., a red light) in the presence of an undesired occurrence and identifies the undesired occurrence.

In some embodiments, the energy delivery devices are used above a manufacturer's recommended power rating. In some embodiments, cooling techniques described herein are applied to permit higher power delivery. The present invention is not limited to a particular amount of power increase. In some embodiments, power ratings exceed manufacturer's recommendation by 5× or more (e.g., 5×, 6×, 10×, 15×, 20×, etc.).

In addition, the devices of the present invention are configured to deliver energy from different regions of the device (e.g., outer conductor segment gaps, described in more detail below) at different times (e.g., controlled by a user) and at different energy intensities (e.g., controlled by a user). Such control over the device permits the phasing of energy delivery fields for purposes of achieving constructive phase interference at a particular tissue region or destructive phase interference at a particular tissue region. For example, a user may employ energy delivery through two (or more) closely positioned outer conductor segments so as to achieve a combined energy intensity (e.g., constructive phase interference). Such a combined energy intensity may be useful in particularly deep or dense tissue regions. In addition, such a combined energy intensity may be achieved through utilization of two (or more) devices. In some embodiments, phase interference (e.g., constructive phase interference, destructive phase interference), between one or more devices, is controlled by a processor, a tuning element, a user, and/or a power splitter. Thus, the user is able to control the release of energy through different regions of the device and control the amount of energy delivered through each region of the device for purposes of precisely sculpting an ablation zone.

In some embodiments, the energy delivery systems of the present invention utilize energy delivery devices with optimized characteristic impedance, triaxial design, energy delivery devices having cooling passage channels, "wagon wheel" cross-section, coolant fluid which serves as dielectric material, porous dielectric material, energy delivery devices with a center fed dipole, and/or energy delivery devices having a linear array of antennae components (each described in more detail above and below).

Figure 3A:
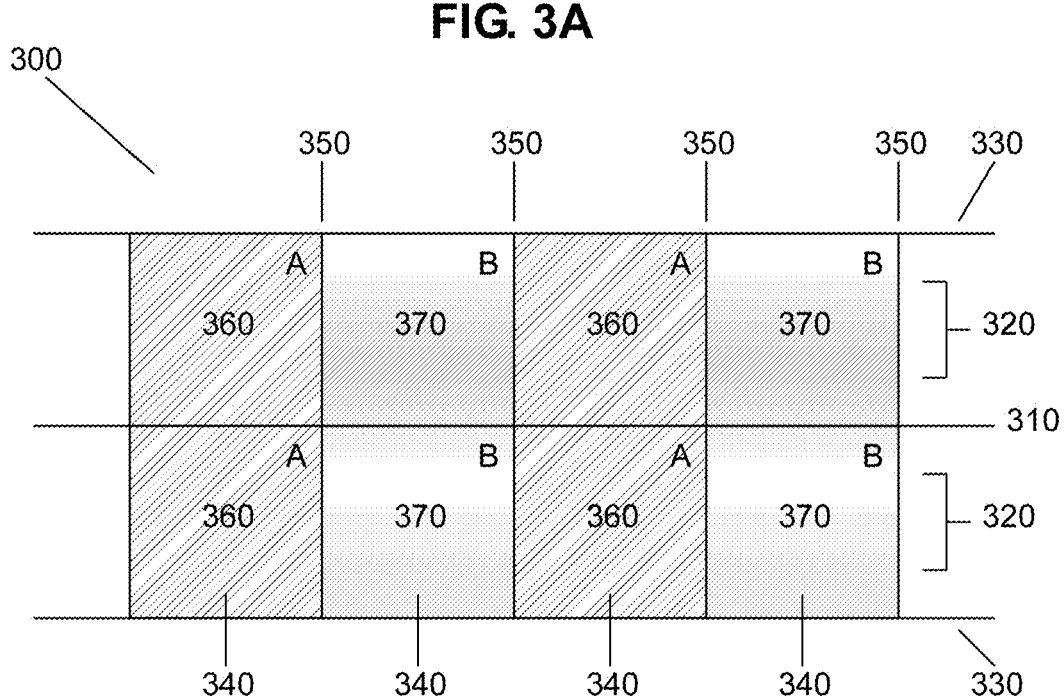
FIG. 3A and FIG. 3B display a coaxial transmission line embodiment having partitioned segments with first and second materials blocked by meltable walls for purposes of preventing undesired device heating (e.g., heating along the outer conductor).
Figure 3B:
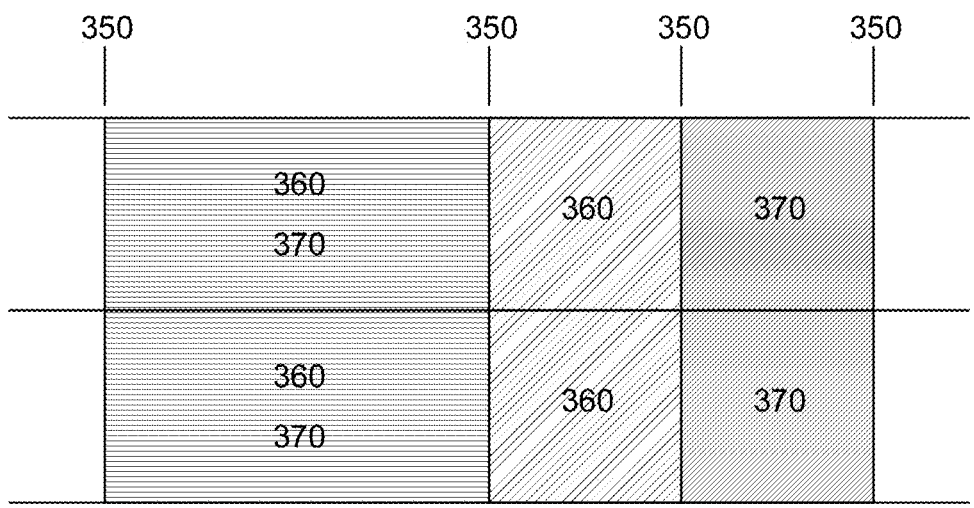

The present invention provides a wide variety of methods for cooling the devices. Some embodiments employ meltable barriers that, upon melting, permit the contact of chemicals that carry out an endothermic reaction. An example of such an embodiment is shown in FIG. 3. FIGS. 3A and 3B display a region of a coaxial transmission line (e.g., a channel) having partitioned segments with first and second materials blocked by meltable walls for purposes of preventing undesired device heating (e.g., heating along the outer conductor). FIGS. 3A and 3B depict a standard coaxial transmission line 300 configured for use within any of the energy delivery devices of the present invention. As shown in FIG. 3A, the coaxial transmission line 300 has a center conductor 310, a dielectric material 320, and an outer conductor 330. In addition, the coaxial transmission line 300 has therein four partitioned segments 340 segregated by walls 350 (e.g., meltable wax walls). The partitioned segments 340 are divided into first partitioned segments 360 and second partitioned segments 370. In some embodiments, as shown in FIG. 3A, the first partitioned segments 360 and second partitioned segments 370 are successively staggered. As shown in FIG. 3A, the first partitioned segments 360 contain a first material (shading type one) and the second partitioned segments 370 contain a second material (shading type two). The walls 350 prevent the first material and second material from mixing. FIG. 3B shows the coaxial transmission line 300 described in FIG. 3A following an event (e.g., a temperature increase at one of the partitioned segments 340). As shown, one of the walls 350 has melted thereby permitting mixing of the first material contained in a region 360 and second material contained in a region 370. FIG. 3B further shows non-melted walls 350 where the temperature increase did not rise above a certain temperature threshold.

FIG. 4 shows an alternative embodiment. FIGS. 4A and 4B display a coaxial transmission line embodiment having partitioned segments segregated by meltable walls containing first and second materials (e.g., materials configured to generate a temperature reducing chemical reaction upon mixing) preventing undesired device heating (e.g., heating along the outer conductor). FIGS. 4A and 4B show a coaxial transmission line 400 configured for use within any of the energy delivery devices of the present invention. As shown in FIG. 4A, the coaxial transmission line 400 has a center conductor 410, a dielectric material 420, and an outer conductor 430. In addition, the coaxial transmission line 400 has therein four partitioned segments 440 segregated by walls 450. The walls 450 each contain a first material 460 separated from a second material 470. FIG. 4B shows the coaxial transmission line 400 described in FIG. 4A following an event (e.g., a temperature increase at one of the partitioned segments 440). As shown, one of the walls 450 has melted thereby permitting mixing of the first material 460 and second material 470 within the adjacent partitioned segments 440. FIG. 4B further demonstrates non-melted walls 450 where the temperature increase did not rise above a certain temperature threshold.

In some embodiments, the device further comprises an anchoring element for securing the antenna at a particular tissue region. The device is not limited to a particular type of anchoring element. In some embodiments, the anchoring element is an inflatable balloon (e.g., wherein inflation of the balloon secures the antenna at a particular tissue region). An additional advantage of utilizing an inflatable balloon as an anchoring element is the inhibition of blood flow or air flow to a particular region upon inflation of the balloon. Such air or blood flow inhibition is particularly useful in, for example, cardiac ablation procedures and ablation procedures involving lung tissue, vascular tissue, and gastrointestinal tissue. In some embodiments, the anchoring element is an extension of the antenna designed to engage (e.g., latch onto) a particular tissue region. Further examples include, but are not limited to, the anchoring elements described in U.S. Pat. Nos. 6,364,876, and 5,741,249; each herein incorporated by reference in their entireties. In some embodiments, the anchoring element has a circulating agent (e.g. a gas delivered at or near its critical point; $CO_2$) that freezes the interface between antenna and tissue thereby sticking the antenna in place. In such embodiments, as the tissue melts the antenna remains secured to the tissue region due to tissue desiccation.

In some embodiments, the devices of the present invention are used in the ablation of a tissue region having high amounts of air and/or blood flow (e.g., pulmonary tissue, cardiac tissue, gastrointestinal tissue, vascular tissue). In some embodiments involving ablation of tissue regions having high amounts of air and/or blood flow, an element is further utilized for inhibiting the air and/or blood flow to that tissue region. The present invention is not limited to a particular air and/or blood flow inhibition element. In some embodiments, the device is combined with an endotracheal/endobronchial tube. In some embodiments, a balloon attached with the device may be inflated at the tissue region for purposes of securing the device(s) within the desired tissue region, and inhibiting blood and/or air flow to the desired tissue region.

Thus, in some embodiments, the systems, devices, and methods of the present invention provide an ablation device coupled with a component that provides occlusion of a passageway (e.g., bronchial occlusion). The occlusion component (e.g., inflatable balloon) may be directly mounted on the ablation system or may be used in combination with another component (e.g., an endotracheal or endobronchial tube) associated with the system.

In some embodiments, the devices of the present invention may be mounted onto additional medical procedure devices. For example, the devices may be mounted onto endoscopes, intravascular catheters, bronchoscopes, or laproscopes. In some embodiments, the devices are mounted onto steerable catheters. In some embodiments, a flexible catheter is mounted on an endoscope, intravascular catheter or laparoscope. For example, the flexible catheter, in some embodiments, has multiple joints (e.g., like a centipede) that permits bending and steering as desired to navigate to the desired location for treatment. In some embodiments, devices of the present invention are deployed through endoscopes, intravascular catheters, bronchoscopes, or laproscopes.

In some embodiments, the energy delivery devices have therein a plug region designed to separate interior portion of the energy delivery device so as to, for example, prevent cooling or heating of a portion or portions of the device while permitting cooling or heating of other portions. The plug region may be configured to segregate any desired region or regions of an energy delivery device from any other. In some embodiments, the plug region is designed to prevent cooling of one or more regions of an energy delivery device. In some embodiments, the plug region is designed to prevent cooling of the portion of the energy delivery device configured to deliver ablative energy. The plug region is not limited to a particular manner of preventing cooling of a portion of the device. In some embodiments, the plug region is designed to be in contact with a region having a reduced temperature (e.g., a region of the energy delivery device having circulated coolant). In some embodiments, the material of the plug region is such that it is able to be in contact with a material or region having a low temperature without having its temperature significantly reduced (e.g., an insulating material). The plug region is not limited to a particular type of insulating material (e.g., a synthetic polymer (e.g., polystyrene, polyicynene, polyurethane, polyisocyanurate), aerogel, fibre-glass, cork). The plug region is not limited to particular size dimensions. In some embodiments, the size of the plug region is such that it is able to prevent the cooling effect of a circulating coolant from reducing the temperature of other regions of the energy delivery device. In some embodiments, the plug region is positioned along the entire cannula portion of an energy delivery device. In some embodiments, the plug region is positioned at a distal portion of the cannula portion of an energy delivery device. In some embodiments, the plug region wraps around the external portion of the cannula portion of an energy delivery device.

In some embodiments, the energy delivery devices have therein a "stick" region designed for securing the energy delivery device to a tissue region. The stick region is not limited to a particular manner of facilitating association of an energy delivery device to a tissue region. In some embodiments, the stick region is configured to attain and maintain a reduced temperature such that upon contact with a tissue region, the tissue region adheres to the stick region thereby resulting in attachment of the energy delivery device with the tissue region. The stick region is not limited to a particular material composition. In some embodiments, the stick region is, for example, a metal material, a ceramic material, a plastic material, and/or any combination of such substances. In some embodiments, the stick region comprises any kind of material able to attain and maintain a temperature such that upon contact with a tissue region induces adherence of the tissue region onto the stick region. The stick region is not limited to particular size dimensions. In some embodiments, the size of the stick region is such that it is able to maintain adherence of a tissue region during simultaneous tissue ablation and/or simultaneous movement (e.g., positioning) of the energy delivery device. In some embodiments, two or more stick regions are provided.

Figure 29:
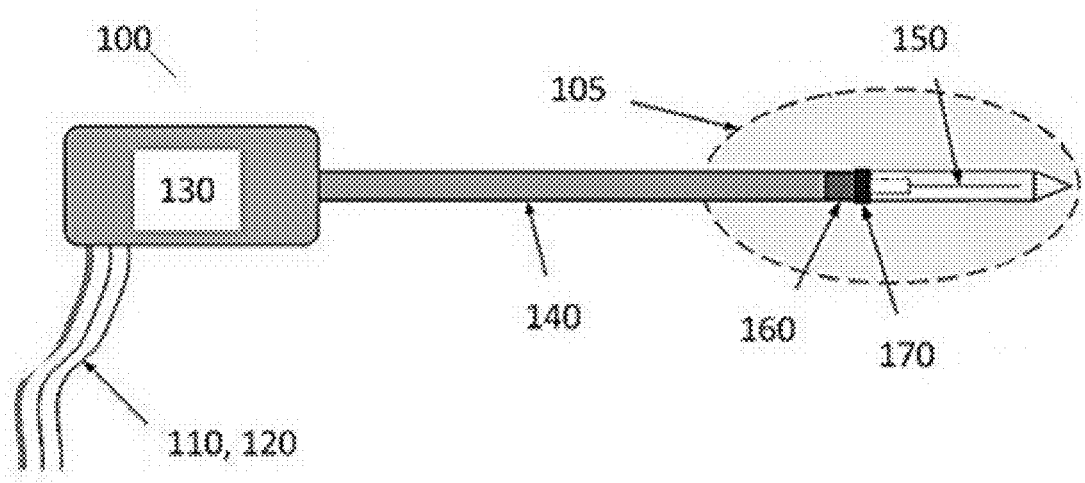
FIG. 29 shows an energy delivery device embodiment.

FIG. 29 shows an energy delivery device embodiment of the present invention. As shown, an energy delivery device 100 is positioned in the vicinity of an ablation zone 105. As shown, the energy delivery device 100 has a cooling tube 110 and cable assembly 120 connected with a handle 130, which is connected with a cooled probe cannula 140 connected with an antenna region 150. As shown, the region between the cooled probe cannula 140 and the antenna region 150 has therein a stick region 160 and a plug region 170. The stick region 160 is designed to attain and maintain a temperature accommodating adherence of a tissue region onto its surface. The plug region 170 is designed to prevent a reduction in temperature resulting from the cooled probe cannula 140 and the stick region 160 from affecting (e.g., reducing) the temperature within the antenna region 150. As shown, in these embodiments, the ablation zone 105, encompasses both a cooled region of the energy delivery device 100 (e.g., the cooled probe cannula 140 and the stick region 160) and a non-cooled region of the energy delivery device 100 (e.g., the plug region 170 and the antenna region 150).

In some embodiments, the energy delivery systems of the present invention utilize devices configured for delivery of microwave energy with an optimized characteristic impedance (see, e.g., U.S. patent application Ser. No. 11/728,428; herein incorporated by reference in its entirety). Such devices are configured to operate with a characteristic impedance higher than 50Ω (e.g., between 50 and 90Ω; e.g., higher than 50, . . . , 55, 56, 57, 58, 59, 60, 61, 62, . . . 90Ω, preferably at 77Ω). In some embodiments, optimized characteristic impedance is achieved through selection of (or absence of) an appropriate dielectric material. Energy delivery devices configured to operate with optimized characteristic impedance are particularly useful in terms of tissue ablation procedures, and provide numerous advantages over non-optimized devices. For example, a major drawback with currently available medical devices that utilize microwave energy is the undesired dissipation of the energy through transmission lines onto a subject's tissue resulting in undesired burning. Such microwave energy loss results from limitations within the design of currently available medical devices. Standard impedance for coaxial transmission lines within medical devices is 50Ω or lower. Generally, coaxial transmission lines with impedance lower than 50Ω have high amounts of heat loss due to the presence of dielectric materials with finite conductivity values. As such, medical devices with coaxial transmission lines with impedance at 50Ω or lower have high amounts of heat loss along the transmission lines. In particular, medical devices utilizing microwave energy transmit energy through coaxial cables having therein a dielectric material (e.g., polyfluorothetra-ethylene or PTFE) surrounding an inner conductor. Dielectric materials such as PTFE have a finite conductivity, which result in the undesired heating of transmission lines. This is particularly true when one supplies the necessary amounts of energy for a sufficient period of time to enable tissue ablation. Energy delivery devices configured to operate with optimized characteristic impedance overcome this limitation by lacking, or substantially lacking, a solid dielectric insulator. For example, using air in place of a traditional dielectric insulator results in an efficient device operating at 77Ω. In some embodiments, the devices employ a near-zero conductivity dielectric material (e.g., air, water, inert gases, vacuum, partial vacuum, or combinations thereof). The overall temperature of the transmission lines within such devices are greatly reduced through use of coaxial of triaxial transmission lines or with near-zero conductivity dielectric materials, and therefore, greatly reduce undesired tissue heating.

In addition, by providing a coaxial or triaxial transmission line with a dielectric material having near-zero conductivity, and avoiding the use of typical dielectric polymers, the coaxial transmission line may be designed such that it can fit within small needles (e.g., 18-20 gauge needles) or similarly small or smaller catheters. Typically, medical devices configured to delivery microwave energy are designed to fit within large needles due to bulky dielectric materials. Microwave ablation has not been extensively applied clinically due to the large probe size (14 gauge) and relatively small zone of necrosis (1.6 cm in diameter) (Seki T et al., Cancer 74:817 (1994)) that is created by the only commercial device (Microtaze, Nippon Shoji, Osaka, Japan. 2.450 MHz, 1.6 mm diameter probe, 70 W for 60 seconds). Other devices use a cooling external water jacket that also increases probe size and can increase tissue damage. These large probe sizes increase the risk of complications when used in the chest and abdomen.

In some embodiments, the energy delivery systems of the present invention utilize energy delivery devices having coolant passage channels (see, e.g., U.S. Pat. No. 6,461,351, and U.S. patent application Ser. No. 11/728,460; herein incorporated by reference in its entirety). In particular, the energy delivery systems of the present invention utilize devices with coaxial or triaxial transmission lines that allow cooling by flowing a cooling material through the dielectric and/or the inner or outer conductor of the coaxial component. In some embodiments, coolant channels comprise part of or all of the dielectric space. In some embodiments, the devices are configured to minimize the diameter of the device, while permitting the passage of the coolant. In some embodiments, coolant fluid comprises dielectric material. In some embodiments, space required for a cooled transmission line is minimized by using the dielectric material as a coolant (e.g. flowable coolant). This is accomplished, in some embodiments, by replacing strips of the inner or outer conductor and/or solid dielectric material with channels through which a coolant is transferred. In some embodiments, the channels are generated by stripping the outer or inner conductor and/or solid dielectric material along the length of the coaxial cable from one or more (e.g., two, three, four) zones. With the removed portions of the outer or inner conductor and/or solid dielectric material creating channels for transfer of the coolant, the stripped component fits within a smaller outer conductor than it did prior to removal of the outer or inner conductor and/or solid dielectric material. In other embodiments, a portion of the dielectric space is used as a coolant channel. These embodiments provide for smaller devices with all of the advantages derived therefrom. In some embodiments where multiple channels are employed, coolant transfer may be in alternative directions through one or more of the channels. An advantage of such devices is that the diameter of the coaxial or triaxial cable does not need to be increased to accommodate coolant. Other embodiments utilize porous dielectric material through with coolant can be flowed to achieve reduced temperature without increasing diameter. Likewise, flowing the dielectric material itself as a coolant permits cooling the coaxial or triaxial transmission line without increasing the cross-sectional profile. This permits the use of cooled devices that are minimally invasive and permit access to regions of a body that are otherwise inaccessible or accessible only with undesired risk. The use of coolant also permits greater energy delivery and/or energy deliver for prolonged periods of time. Additional cooling embodiments are described above in the Summary of the Invention.

In some embodiments, the device has a handle attached to the device, wherein the handle is configured to, for example, control the passing of coolant into and out of the coolant channels. In some embodiments, the handle automatically passes coolant into and out of the coolant channels after a certain amount of time and/or as the device reaches a certain threshold temperature. In some embodiments, the handle automatically stops passage of coolant into and out of the coolant channels after a certain amount of time and/or as the temperature of the device drops below a certain threshold temperature. In some embodiments, the handle is manually controlled to adjust coolant flow.

Figure 30:
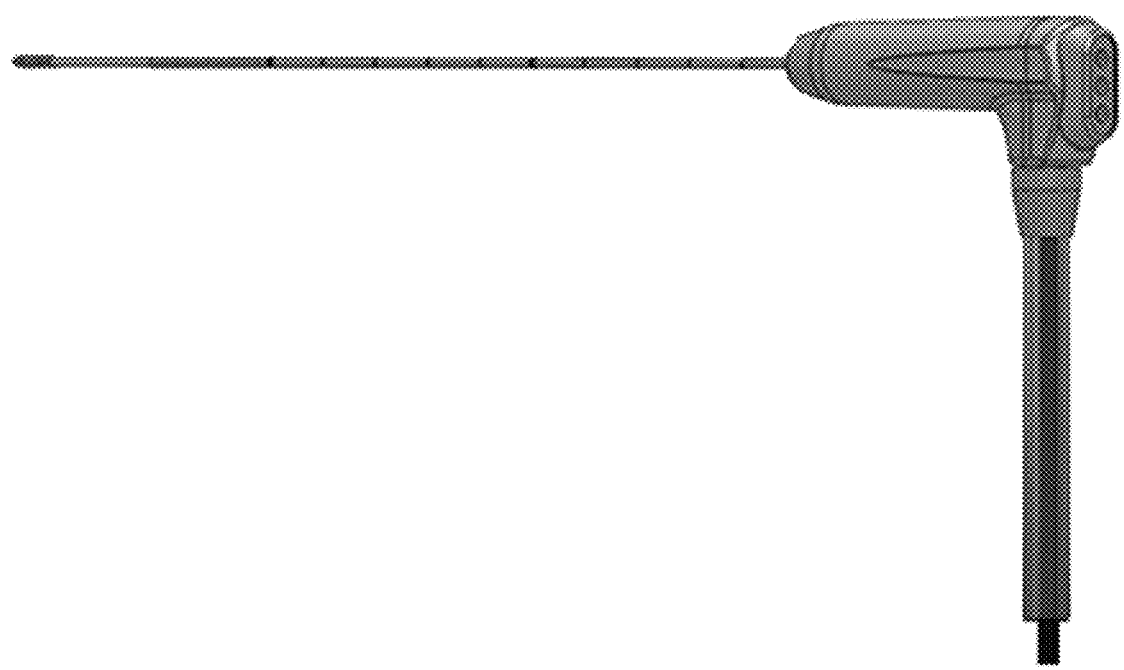
FIG. 30 shows an energy delivery device embodiment.
Figure 31:
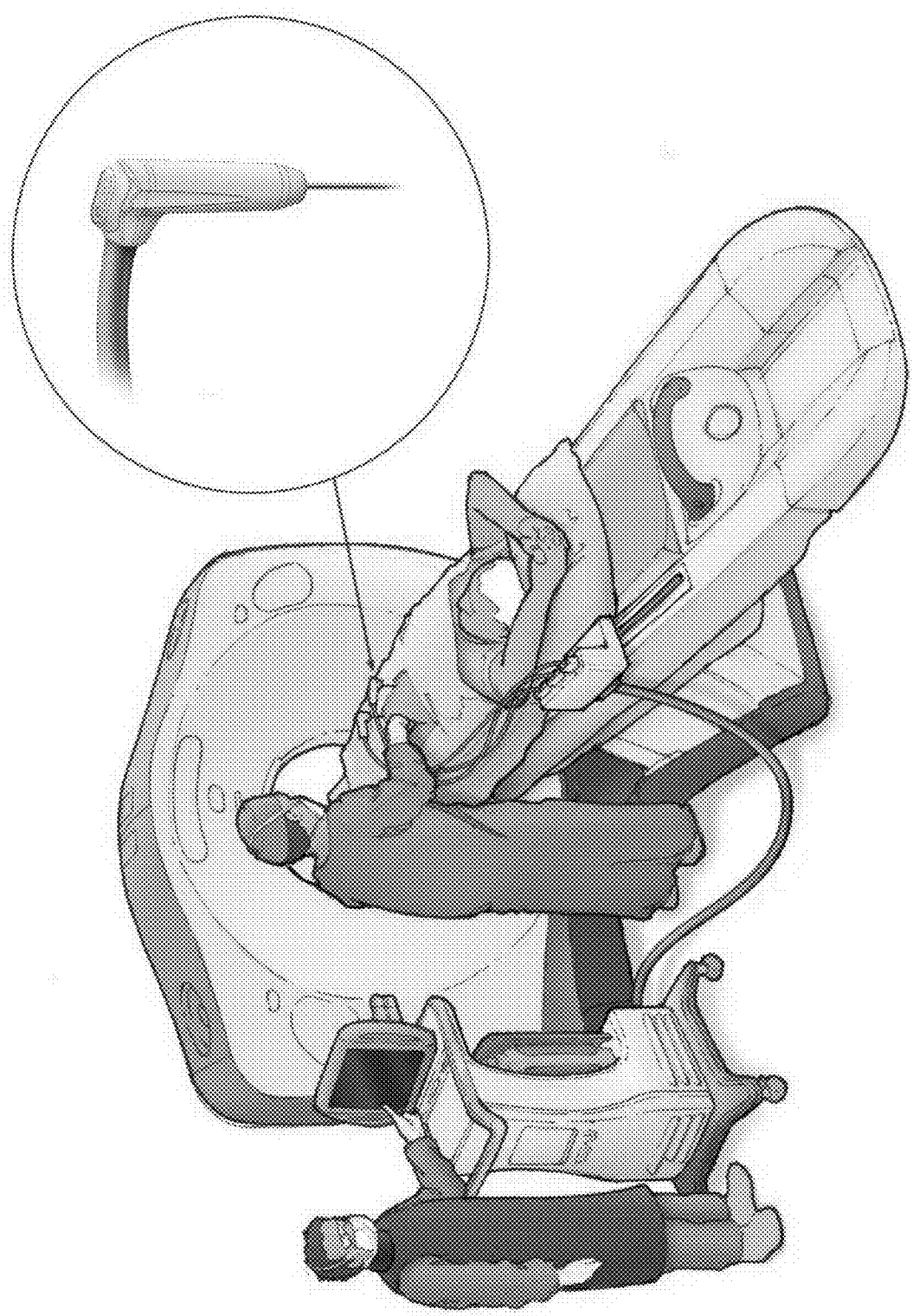
FIG. 31 shows an energy delivery device embodiment within a procedure setting.

In some embodiments, the handle has thereon one or more (e.g., 1, 2, 3, 4, 5, 6, 7, 8, 9, 10, etc.) lights (e.g., display lights (e.g., LED lights)). In some embodiments, the lights are configured to for identification purposes. For example, in some embodiments, the lights are used indicate whether a particular function of the device is active or inactive. For example, where devices have multiple probes, one or more lights is used to indicate whether any individual probe is powered or unpowered. In some embodiments, the lights are used to identify the occurrence of an event (e.g., the transmission of coolant through the device, the transmission of energy through the device, a movement of the respective probe, a change in a setting (e.g., temperature, positioning) within the device, etc.). The handles are not limited to a particular manner of display (e.g., blinking, alternate colors, solid colors, etc). FIG. 30 shows a device 30000 with three LED lights 31000, 32000, and 33000. FIG. 31 shows such a device 30000 in use wherein the device has three LED lights 31000, 32000, and 33000.

Figure 5:
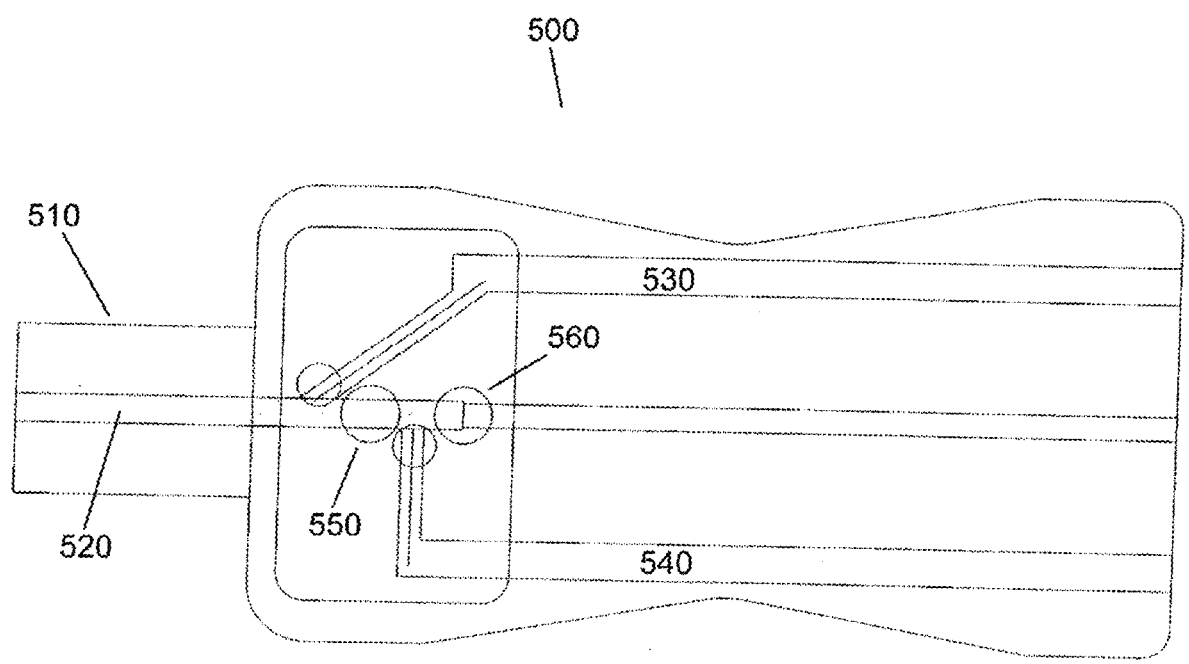
FIG. 5 shows a schematic drawing of a handle configured to control the passing of coolant into and out of the coolant channels.

FIG. 5 shows a schematic drawing of a handle configured to control the passing of coolant into and out of the coolant channels. As shown in FIG. 5, the handle 500 is engaged with a coaxial transmission line 510 having a coolant channel 520. The handle 500 has therein a coolant input channel 530, a coolant output channel 540, a first blocking component 550 (e.g., a screw or pin) configured to prevent flow through channel 520 behind the blocking component and a second blocking component 560. The coolant input channel 530 is configured to provide coolant to the coolant channel 520. The coolant output channel 540 is configured to remove coolant from the coolant channel 520 (e.g., coolant that has circulated and removed heat from a device). The coolant input channel 530 and coolant output channel 540 are not limited to particular sizes or means for providing and removing coolant. The first blocking components 550 and second blocking component 560 are not limited to particular sizes or shapes. In some embodiments, the first blocking component 550 and second blocking component 560 each have a circular shape and a size that matches the diameter of the coolant input channel 530 and the coolant output channel 540. In some embodiments, the first blocking component 550 and second blocking component 560 are used to block the backflow of coolant to a certain region of the handle 500. In some embodiments, the blocking components are configured such that only a portion (e.g., 1%, 5%, 10%, 20%, 50%, 75%, 85%, 95%, 99%) of the channel is blocked. Blocking only a portion permits the user, for example, to vary the pressure gradients within the coolant channel 520.

Energy delivery devices having coolant passage channels allow for adjustment of the characteristic impedance of the coaxial transmission line. In particular, the dielectric properties of the coolant (or of a non-coolant material that is passed through the channel(s)) may be adjusted to alter the bulk complex permittivity of the dielectric medium separating the outer and inner conductors. As such, changes in the characteristic impedance are made during a procedure to, for example, optimize energy delivery, tissue effects, temperature, or other desired properties of the system, device, or application. In other embodiments, a flow material is selected prior to a procedure based on the desired parameters and maintained throughout the entire procedure. Thus, such devices provide an antenna radiating in a changing dielectric environment to be adjusted to resonate in the changing environment to, for example, allow adaptive tuning of the antenna to ensure peak efficiency of operation. As desired, the fluid flow also allows heat transfer to and from the coaxial cable. In some embodiments, the channels or hollowed out areas contain a vacuum or partial vacuum. In some embodiments, impedance is varied by filling the vacuum with a material (e.g., any material that provides the desired result). Adjustments may be made at one or more time points or continuously.

The energy delivery devices having coolant passage channels are not limited to particular aspects of the channels. In some embodiments, the channel is cut through only a portion of the outer or inner conductor and/or solid dielectric material so that the flowed material is in contact with either the inner or outer conductor and the remaining dielectric material. In some embodiments, the channels are linear along the length of the coaxial cable. In some embodiments, the channels are non-linear. In some embodiments, where more than one channel is used, the channels run parallel to one another. In other embodiments, the channels are not parallel. In some embodiments, the channels cross one another. In some embodiments, the channels remove over 50% (e.g., 60%, 70%, 80%, etc.) of the outer or inner conductor and/or solid dielectric material. In some embodiments, the channels remove substantially all of the outer or inner conductor and/or solid dielectric material. In some embodiments, two or more channels converge to allow mixing of fluid (e.g. to induce an endothermic reaction). In some embodiments, coolant channels comprise 1-100% of the dielectric space (e.g. 1% . . . 2% . . . 5% . . . 10% . . . 20% . . . 50% . . . 90% . . . 100%).

The energy delivery devices having coolant passage channels are not limited by the nature of the material that is flowed through the outer or inner conductor, collapsible channels, dielectric space, coolant channels, porous dielectric material, and/or solid dielectric material. In some embodiments, the material is selected to maximize the ability to control the characteristic impedance of the device, to maximize heat transfer to or from the coaxial cable, or to optimize a combination of control of the characteristic impedance and heat transfer. In some embodiments, the material that is flowed through the outer or inner conductor and/or solid dielectric material is a liquid. In some embodiments, the material is a gas. In some embodiments, the material is a combination of liquid or gas. The present invention is not limited to the use of liquids or gasses. In some embodiments, the material is a slurry, a gel, or the like. In some embodiments, a coolant fluid is used. Any coolant fluid now known or later developed may be used. Exemplary coolant fluids include, but are not limited to, one or more of or combinations of, water, glycol, air, inert gasses, carbon dioxide, nitrogen, helium, sulfur hexafluoride, ionic solutions (e.g., sodium chloride with or without potassium and other ions), dextrose in water, Ringer's lactate, organic chemical solutions (e.g., ethylene glycol, diethylene glycol, or propylene glycol), oils (e.g., mineral oils, silicone oils, fluorocarbon oils), liquid metals, freons, halomethanes, liquified propane, other haloalkanes, anhydrous ammonia, sulfur dioxide. In some embodiments, the coolant fluids are pre-cooled prior to delivery into the energy deliver device. In some embodiments, the coolant fluids are cooled with a cooling unit following entry into the energy delivery device. In some embodiments, the material passed through the dielectric material is designed to generate an endothermic reaction upon contact with an additional material.

The energy delivery devices having coolant passage channels are configured to permit control over the parameters of fluid infusion through the device. In some embodiments, the device is manually adjusted by the user (e.g., a treating physician or technician) as desired. In some embodiments, the adjustments are automated. In some embodiments, the devices are configured with or used with sensors that provide information to the user or the automated systems (e.g., comprising processors and/or software configured for receiving the information and adjusting fluid infusion or other device parameters accordingly). Parameters that may be regulated include, but are not limited to, speed of infusion of the fluid, concentration of ions or other components that affect the properties of the fluid (e.g., dielectric properties, heat transfer properties, flow rate, etc.), temperature of the fluid, type of fluid, mixture ratios (e.g., mixtures of gas/fluid for precise tuning or cooling). Thus, energy delivery devices having coolant passage channels are configured to employ a feed-back loop that can change one or more desired parameters to tune the device (e.g., antenna) more accurately, or speed up the infusion of the fluid if the device, portions of the device, or tissue of the subject reaches an undesired temperature (or a temperature for an undesired period of time).

The energy delivery devices having coolant passage channels provide numerous advantages over the currently available systems and devices. For example, by providing a coaxial or triaxial transmission line with channels carved out of, and that can substantially remove the volume of solid dielectric material, the transmission line may be designed such that it can fit within very small needles (e.g., 18-20 gauge needles or smaller). Likewise, using a portion or all of the dielectric space as both dielectric material and coolant, the diameter of the line can be reduced. Typically, medical devices configured to delivery microwave energy are designed to fit within large needles due to bulky dielectric materials. Other devices use a cooling external water jacket that also increases probe size and can increase tissue damage. These large probe sizes increase the risk of complications when used in the chest and abdomen. Further, these probes cannot access high circuitous and branched structures within a subject, due to their broad size and reduced flexibility. In some embodiments of the present invention, the maximum outer diameter of the portion of the device that enters a subject is 16-18 gauge or less (20 gauge or less).

FIG. 6 shows a transverse cross-section schematic of standard coaxial cable embodiments and embodiments of the present invention having coolant passages. As shown in FIG. 6, a conventional coaxial cable 600 and two exemplary coaxial cables of the present invention, 610 and 620 are provided. A coaxial cable is made, generally, of three separate spaces: a metallic inner conductor 630, a metallic outer conductor 650, and a space between them. The space between them is usually filled with a low-loss dielectric material 640 (e.g., polyfluorotetraethylene, or PTFE) to mechanically support the inner conductor and maintain it with the outer conductor. The characteristic impedance of a coaxial cable is fixed by the ratio of diameters of the inner conductor and dielectric material (i.e., inner diameter of the outer conductor) and the permittivity of the space between them. Usually, the permittivity is fixed because of the solid polymer comprising it. However, in embodiments of the present invention, a fluid with variable permittivity (or conductivity) at least partially occupies this space, permitting the characteristic impedance of the cable to be adjusted.

Still referring to FIG. 6, in one embodiment of the present invention, the coaxial cable 610 has the outer portion of the dielectric material removed to create a channel between the dielectric material 640 and the outer conductor 650. In the embodiments shown, the created space is separated into four distinct channels 670 by the addition of support lines 660 configured to maintain the space between the outer conductor 650 and the solid dielectric material 640. The support lines 660 may be made of any desired material and may be the same or a different material as the solid dielectric material 640. In some embodiments, so as to avoid undesired heating of the device (e.g., undesired heating of the outer conductor), the support lines 660 are made of a biocompatible and meltable material (e.g., wax). The presence of multiple channels permits one or more of the channels to permit flow in one direction (towards the proximal end of the cable) and one or more other channels to permit flow in the opposite direction (towards the distal end of the cable).

Still referring to FIG. 6, in another embodiment, the coaxial cable 620 has a substantial portion of the solid dielectric material 640 removed. Such an embodiment may be generated, for example, by stripping away the solid dielectric material 640 down to the surface of inner conductor 630 on each of four sides. In another embodiment, strips of dielectric material 640 are applied to an inner conductor 630 to create the structure. In this embodiment, four channels 670 are created. By removing a substantial amount of the dielectric material 640, the diameter of the outer conductor 650 is substantially reduced. The corners provided by the remaining dielectric material 640 provide the support to maintain the position of the outer conductor 650 with respect to the inner conductor 630. In this embodiment, the overall diameter of the coaxial cable 620 and the device is substantially reduced.

Figure 7:
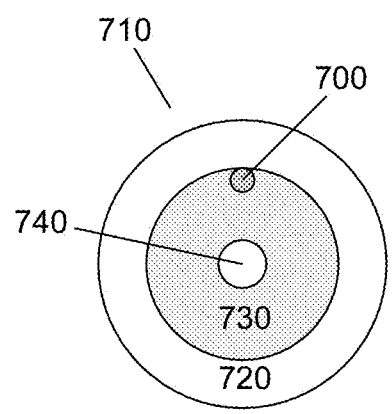
FIG. 7 shows a coolant circulating tube (e.g., coolant needle, catheter) positioned within an energy emission device having an outer conductor and a dielectric material.

In some embodiments, the devices have a coolant passage formed through insertion of a tube configured to circulate coolant through the dielectric portion or inner or outer conductors of any of the energy emission devices of the present invention. FIG. 7 shows a coolant circulating tube 700 (e.g., coolant needle, catheter) positioned within an energy emission device 710 having an outer conductor 720, a dielectric material 730, and an inner conductor 740. As shown in FIG. 7, the tube 700 is positioned along the outside edge of the dielectric material 730 and inside edge of the outer conductor 720, with the inner conductor 740 positioned approximately in the center of the dielectric material 730. In some embodiments, the tube 700 is positioned within the dielectric material 730 such that it does not contact the outer conductor 720. In some embodiments, the tube 700 has multiple channels (not shown) for purposes of recirculating the coolant within the tube 700 without passing the coolant into the dielectric material 730 and/or the outer conductor 720, thereby cooling the dielectric material 730 and/or the outer conductor 720 with the exterior of the tube 700.

In some embodiments, the energy delivery systems of the present invention utilize energy delivery devices employing a center fed dipole component (see, e.g., U.S. patent application Ser. No. 11/728,457; herein incorporated by reference in its entirety). The devices are not limited to particular configurations. In some embodiments, the devices have therein a center fed dipole for heating a tissue region through application of energy (e.g., microwave energy). In some embodiments, such devices have a coaxial cable or triaxial cable connected to a hollow tube (e.g., where the interior diameter is at least 50% of the exterior diameter; e.g., where the interior diameter is substantially similar to the exterior diameter). The coaxial or triaxial cable may be a standard coaxial or triaxial cable, or it may be a coaxial or triaxial cable having therein a dielectric component with a near-zero conductivity (e.g., air). The coaxial or triaxial transmission line may comprise one or more coolant channels within the dielectric space or between the second and third conductors. The tube is not limited to a particular design configuration. In some embodiments, the tube assumes the shape of (e.g., diameter of), for example, a 20-gauge needle. In some embodiments, transmission lines are of a gauge less than that of a 20-gauge needle. Preferably, the tube is made of a solid, conductive material (e.g., any number of metals, conductor-coated ceramics or polymers, etc.). In some embodiments, the tube is constructed of a braided material (e.g. braided metal) to provide both strength and flexibility. In some embodiments, a hollow tube is configured with a sharpened point or the addition of a stylet on its distal end to permit direct insertion of the device into a tissue region without the use of, for example, a cannula. The tube is not limited to a particular composition (e.g., metal, plastic, ceramic). In some embodiments, the tube comprises, for example, copper or copper alloys with other hardening metals, silver or silver alloys with other hardening metals, gold-plated copper, metal-plated Macor (machinable ceramic), metal-plated hardened polymers, and/or combinations thereof.

In some embodiments, the center fed dipole is configured to adjust the energy delivery characteristics in response to heating so as to provide a more optimal energy delivery throughout the time period of a process. In some embodiments, this is achieved by using a material that changes volume in response to temperature changes such that the change in the volume of the material changes to the energy delivery characteristics of the device. In some embodiments, for example, an expandable material is placed in the device such that the resonant portion of the center fed dipole component or the stylet is pushed distally along the device in response to heating. This changes the tuning of the device to maintain a more optimal energy delivery. The maximum amount of movement can be constrained, if desired, by, for example, providing a locking mechanism that prevents extension beyond a particular point.

The energy delivery devices employing a center fed dipole component are not limited by the manner in which the hollow tube is connected to the coaxial or triaxial cable. In some embodiments, a portion of the outer conductor at the distal end of the coaxial cable feedline is removed, exposing a region of solid dielectric material. The hollow tube can be positioned onto the exposed dielectric material and attached by any means. In some embodiments, a physical gap between the outer conductor and the hollow tube is provided. In some embodiments, the hollow tube is capacitively or conductively attached to the feedline at its center point such that the electrical length of the hollow tube comprises a frequency-resonant structure when inserted into tissue.

In use, the energy delivery devices employing a center fed dipole component are configured such that an electric field maximum is generated at the open distal end of the hollow tube. In some embodiments, the distal end of the hollow tube has a pointed shape so as to assist in inserting the device though a subject and into a tissue region. In some embodiments, the entire device is hard and rigid so as to facilitate linear and direct insertion directly to a target site.

In some embodiments, the structure resonates at, for example, ~2.45 GHz, as characterized by a minimum in the reflection coefficient (measured at the proximal end of the feedline) at this frequency. By changing the dimensions of the device (e.g., length, feed point, diameter, gap, etc.) and materials (dielectric materials, conductors, etc.) of the antenna, the resonant frequency may be changed. A low reflection coefficient at a desired frequency ensures efficient transmission of energy from the antenna to the medium surrounding it.

Preferably, the hollow tube is of length $\lambda/2$, where $\lambda$ is the electromagnetic field wavelength in the medium of interest (e.g., ~18 cm for 2.45 GHz in liver) to resonate within the medium. In some embodiments, the length of the hollow tube is approximately $\lambda/2$, where $\lambda$ is the electromagnetic field wavelength in the medium of interest to resonate within the medium, such that a minimum of power reflection at the proximal end is measured. However, deviations from this length may be employed to generate resonant wavelengths (e.g., as the surrounding materials are changed). Preferably, the inner conductor of a coaxial cable is extended with its distal end at the tube center (e.g., at $\lambda/4$ from the end of the tube) and configured such that the inner conductor maintains electrical contact at the tube center, although deviations from this position are permitted (e.g., to generate resonant wavelengths).

The hollow tube portion of the present invention may have a wide variety of shapes. In some embodiments, the tube is cylindrical throughout its length. In some embodiments, tube tapers from a center position such that it has a smaller diameter at its end as compared to its center. Some embodiments, having a smaller point at the distal end assists in penetrating a subject to arrive at the target region. In some embodiments, where the shape of the hollow tube deviates from a cylindrical shape, the tube maintains a symmetrical structure on either side of its longitudinal center. However, the devices are not limited by the shape of the hollow tube, so long as the functional properties are achieved (i.e., the ability to deliver desired energy to a target region).

In some embodiments, the center-fed dipole components may be added to the distal end of a wide variety of ablation devices to provide the benefits described herein. Likewise, a wide variety of devices may be modified to accept the center-fed dipole components of the present invention.

In some embodiments, the devices have a small outer diameter. In some embodiments, the center-fed dipole component of the invention is directly used to insert the invasive component of the device into a subject. In some such embodiments, the device does not contain a cannula, allowing for the invasive components to have a smaller outer diameter. For example, the invasive component can be designed such that it fits within or is the size of very small needles (e.g., 18-20 gauge needles or smaller).

Figure 8:
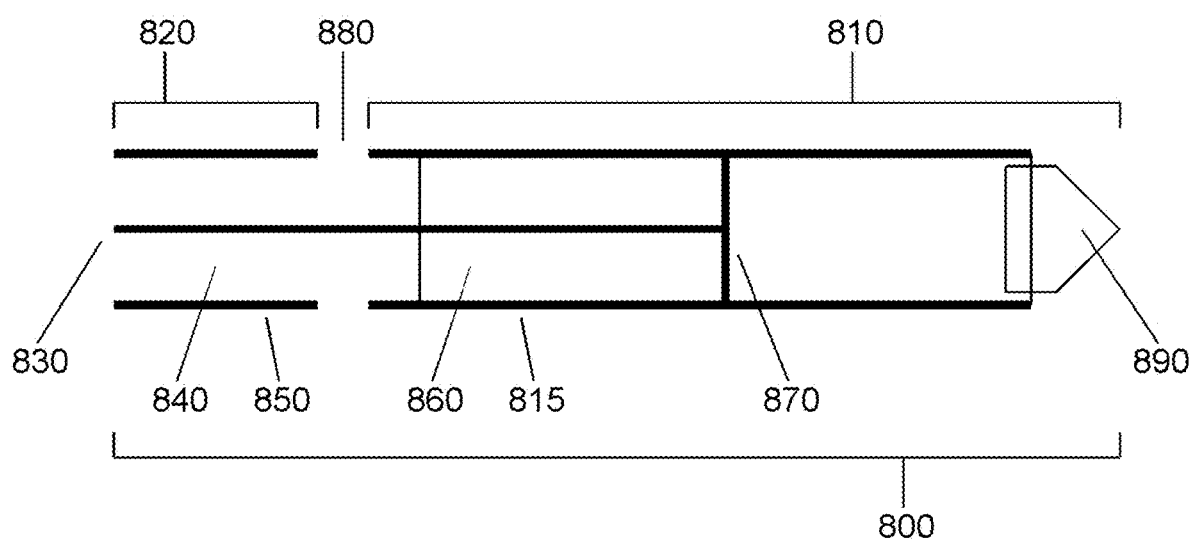
FIG. 8 schematically shows the distal end of a device (e.g., antenna of an ablation device) of the present invention that comprises a center fed dipole component of the present invention.

FIG. 8 schematically shows the distal end of a device 800 (e.g., antenna of an ablation device) of the present invention that comprises a center fed dipole component 810 of the present invention. One skilled in the art will appreciate any number of alternative configurations that accomplish the physical and/or functional aspects of the present invention. As shown, the center fed dipole device 800 has therein a hollow tube 815, a coaxial transmission line 820 (e.g., a coaxial cable), and a stylet 890. The center fed dipole device 800 is not limited to a particular size. In some embodiments, the size of the center fed dipole device 800 is small enough to be positioned at a tissue region (e.g., a liver) for purposes of delivering energy (e.g., microwave energy) to that tissue region.

Referring again to FIG. 8, the hollow tube 815 is not limited to a particular material (e.g., plastic, ceramic, metal, etc.). The hollow tube 815 is not limited to a particular length. In some embodiments, the length of the hollow tube is $\lambda/2$, where $\lambda$ is the electromagnetic field wavelength in the medium of interest (e.g., ~18 cm for 2.45 GHz in liver). The hollow tube 815 engages the coaxial transmission line 820 such that the hollow tube 815 is attached to the coaxial transmission line 820 (described in more detail below). The hollow tube 815 has therein a hollow tube matter 860. The hollow tube 815 is not limited to a particular type of hollow tube matter. In some embodiments, the hollow tube matter 860 is air, fluid or a gas.

Still referring to FIG. 8, the hollow tube 815 is not limited to a particular shape (e.g., cylindrical, triangular, squared, rectangular, etc.). In some embodiments, the shape of the hollow tube 815 is of a needle (e.g., a 20-gauge needle, an 18-gauge needle). In some embodiments, the hollow tube 815 is divided into two portions each of variable length. As shown, the hollow tube 815 is divided into two portions each of equal length (e.g., each portion having a length of $\lambda/4$). In such embodiments, the shapes of each portion are symmetrical. In some embodiments, the hollow tube has a diameter equal to or less than a 20-gauge needle, a 17-gauge needle, a 12-gauge needle, etc.

Still referring to FIG. 8, the distal end of the hollow tube 815 engages a stylet 890. The device 800 is not limited to a particular stylet 890. In some embodiments, the stylet 890 is designed to facilitate percutaneous insertion of the device 800. In some embodiments, the sytlet 890 engages the hollow tube 815 by sliding inside the hollow tube 815 such that the stylet 890 is secured.

Still referring to FIG. 8, the coaxial transmission line 820 is not limited to a particular type of material. In some embodiments, the proximal coaxial transmission line 820 is constructed from commercial-standard 0.047-inch semi-rigid coaxial cable. In some embodiments, the coaxial transmission line 820 is metal-plated (e.g., silver-plated, copper-plated), although the present invention is not so limited. The proximal coaxial transmission line 820 is not limited to a particular length.

Still referring to FIG. 8, in some embodiments, the coaxial transmission line 820 has a coaxial center conductor 830, a coaxial dielectric material 840, and a coaxial outer conductor 850. In some embodiments, the coaxial center conductor 830 is configured to conduct cooling fluid along its length. In some embodiments, the coaxial center conductor 830 is hollow. In some embodiments, the coaxial center conductor 830 has a diameter of, for example, 0.012 inches. In some embodiments, the coaxial dielectric material 840 is polyfluorotetraethylene (PTFE). In some embodiments, the coaxial dielectric material 840 has a near-zero conductivity (e.g., air, fluid, gas).

Still referring to FIG. 8, the distal end of the coaxial transmission line 820 is configured to engage the proximal end of the hollow tube 815. In some embodiments, the coaxial center conductor 830 and the coaxial dielectric material 840 extend into the center of the hollow tube 815. In some embodiments, the coaxial center conductor 820 extends further into the hollow tube 815 than the coaxial dielectric material 840. The coaxial center conductor 820 is not limited to a particular amount of extension into the hollow tube 815. In some embodiments, the coaxial center conductor 820 extends a length of λ/4 into the hollow tube 815. The distal end of the coaxial transmission line 820 is not limited to a particular manner of engaging the proximal end of the hollow tube 815. In some embodiments, the proximal end of the hollow tube engages the coaxial dielectric material 840 so as to secure the hollow tube 815 with the coaxial transmission line 820. In some embodiments, where the coaxial dielectric material 840 has a near-zero conductivity, the hollow tube 815 is not secured with the coaxial transmission line 820. In some embodiments, the distal end of the coaxial center conductor 830 engages the walls of the hollow tube 815 directly or though contact with a conductive material 870, which may be made of the same material as the coaxial center conductor or may be of a different material (e.g., a different conductive material).

Still referring to FIG. 8, in some embodiments, a gap 880 exists between the distal end of the coaxial transmission line outer conductor 850 and the hollow tube 815 thereby exposing the coaxial dielectric material 840. The gap 880 is not limited to a particular size or length. In some embodiments, the gap 880 ensures an electric field maximum at the proximal end of the coaxial transmission line 880 and the distal open end of the hollow tube 815. In some embodiments, the center fed dipole device 810 resonates at ~2.45 GHz, as characterized by a minimum in the reflection coefficient at this frequency. By changing the dimensions (length, feed point, diameter, gap, etc.) and materials (dielectric materials, conductors, etc.) of the device the resonant frequency may be changed. A low reflection coefficient at this frequency ensures efficient transmission of energy from the antenna to the medium surrounding it.

Still referring to FIG. 8, in some embodiments, the gap 880 is filled with a material (e.g., epoxy) so bridge the coaxial transmission line 820 and the hollow tube 815. The devices are not limited to a particular type or kind of substantive material. In some embodiments, the substantive material does not interfere with the generation or emission of an energy field through the device. In some embodiments, the material is biocompatible and heat resistant. In some embodiments, the material lacks or substantially lacks conductivity. In some embodiments, the material further bridges the coaxial transmission line 820 and the hollow tube 815 with the coaxial center conductor 830. In some embodiments, the substantive material is a curable resin. In some embodiments, the material is a dental enamel (e.g., XRV Herculite enamel; see, also, U.S. Pat. Nos. 6,924,325, 6,890,968, 6,837,712, 6,709,271, 6,593,395, and 6,395,803, each herein incorporated by reference in their entireties). In some embodiments, the substantive material is cured (e.g., cured with a curing light such as, for example, L.E. Demetron II curing light) (see, e.g., U.S. Pat. Nos. 6,994,546, 6,702,576, 6,602,074 and 6,435,872). Thus, the present invention provides ablation devices comprising a cured enamel resin. Such a resin is biocompatible and rigid and strong.

III. Processor

In some embodiments, the energy delivery systems of the present invention utilize processors that monitor and/or control and/or provide feedback concerning one or more of the components of the system. In some embodiments, the processor is provided within a computer module. The computer module may also comprise software that is used by the processor to carry out one or more of its functions. For example, in some embodiments, the systems of the present invention provide software for regulating the amount of microwave energy provided to a tissue region through monitoring one or more characteristics of the tissue region including, but not limited to, the size and shape of a target tissue, the temperature of the tissue region, and the like (e.g., through a feedback system) (see, e.g., U.S. patent application Ser. Nos. 11/728,460, 11/728,457, and 11/728,428; each of which is herein incorporated by reference in their entireties). In some embodiments, the software is configured to provide information (e.g., monitoring information) in real time. In some embodiments, the software is configured to interact with the energy delivery systems of the present invention such that it is able to raise or lower (e.g., tune) the amount of energy delivered to a tissue region. In some embodiments, the software is designed to prime coolants for distribution into, for example, an energy delivery device such that the coolant is at a desired temperature prior to use of the energy delivery device. In some embodiments, the type of tissue being treated (e.g., liver) is inputted into the software for purposes of allowing the processor to regulate (e.g., tune) the delivery of microwave energy to the tissue region based upon pre-calibrated methods for that particular type of tissue region. In other embodiments, the processor generates a chart or diagram based upon a particular type of tissue region displaying characteristics useful to a user of the system. In some embodiments, the processor provides energy delivering algorithms for purposes of, for example, slowly ramping power to avoid tissue cracking due to rapid out-gassing created by high temperatures. In some embodiments, the processor allows a user to choose power, duration of treatment, different treatment algorithms for different tissue types, simultaneous application of power to the antennas in multiple antenna mode, switched power delivery between antennas, coherent and incoherent phasing, etc. In some embodiments, the processor is configured for the creation of a database of information (e.g., required energy levels, duration of treatment for a tissue region based on particular patient characteristics) pertaining to ablation treatments for a particular tissue region based upon previous treatments with similar or dissimilar patient characteristics. In some embodiments, the processor is operated by remote control.

In some embodiments, the processor is used to generate, for example, an ablation chart based upon entry of tissue characteristics (e.g., tumor type, tumor size, tumor location, surrounding vascular information, blood flow information, etc.). In such embodiments, the processor could direct placement of the energy delivery device so as to achieve desired ablation based upon the ablation chart. In some embodiments, a processor communicates with positions sensors and/or steering mechanisms to provide appropriate placement of systems and devices of the present invention.

In some embodiments a software package is provided to interact with the processor that allows the user to input parameters of the tissue to be treated (e.g., type of tumor or tissue section to be ablated, size, where it is located, location of vessels or vulnerable structures, and blood flow information) and then draw the desired ablation zone on a CT or other image to provide the desired results. The probes may be placed into the tissue, and the computer generates the expected ablation zone based on the information provided. Such an application may incorporate feedback. For example, CT, MRI, or ultrasound imaging or thermometry may be used during the ablation. This data is fed back into the computer, and the parameters readjusted to produce the desired result.

As used herein, the terms "computer memory" and "computer memory device" refer to any storage media readable by a computer processor. Examples of computer memory include, but are not limited to, random access memory (RAM), read-only memory (ROM), computer chips, optical discs (e.g., compact discs (CDs), digital video discs (DVDs), etc.), magnetic disks (e.g., hard disk drives (HDDs), floppy disks, ZIP® disks, etc.), magnetic tape, and solid state storage devices (e.g., memory cards, "flash" media, etc.).

As used herein, the term "computer readable medium" refers to any device or system for storing and providing information (e.g., data and instructions) to a computer processor. Examples of computer readable media include, but are not limited to, optical discs, magnetic disks, magnetic tape, solid-state media, and servers for streaming media over networks.

As used herein, the terms "processor" and "central processing unit" or "CPU" are used interchangeably and refer to a device that is able to read a program from a computer memory device (e.g., ROM or other computer memory) and perform a set of steps according to the program.

IV. Imaging Systems

In some embodiments, the energy delivery systems of the present invention utilize imaging systems comprising imaging devices. The energy delivery systems are not limited to particular types of imaging devices (e.g., endoscopic devices, stereotactic computer assisted neurosurgical navigation devices, thermal sensor positioning systems, motion rate sensors, steering wire systems, intraprocedural ultrasound, interstitial ultrasound, microwave imaging, acoustic tomography, dual energy imaging, fluoroscopy, computerized tomography magnetic resonance imaging, nuclear medicine imaging devices triangulation imaging, thermoacoustic imaging, infrared and/or laser imaging, electromagnetic imaging) (see, e.g., U.S. Pat. Nos. 6,817,976, 6,577,903, and 5,697,949, 5,603,697, and International Patent Application No. WO 06/005,579; each herein incorporated by reference in their entireties). In some embodiments, the systems utilize endoscopic cameras, imaging components, and/or navigation systems that permit or assist in placement, positioning, and/or monitoring of any of the items used with the energy systems of the present invention.

In some embodiments, the energy delivery systems provide software is configured for use of imaging equipment (e.g., CT, MRI, ultrasound). In some embodiments, the imaging equipment software allows a user to make predictions based upon known thermodynamic and electrical properties of tissue, vasculature, and location of the antenna(s). In some embodiments, the imaging software allows the generation of a three-dimensional map of the location of a tissue region (e.g., tumor, arrhythmia), location of the antenna(s), and to generate a predicted map of the ablation zone.

In some embodiments, the imaging systems of the present invention are used to monitor ablation procedures (e.g., microwave thermal ablation procedures, radio-frequency thermal ablation procedures). The present invention is not limited to a particular type of monitoring. In some embodiments, the imaging systems are used to monitor the amount of ablation occurring within a particular tissue region(s) undergoing a thermal ablation procedure. In some embodiments, the monitoring operates along with the ablation devices (e.g., energy delivery devices) such that the amount of energy delivered to a particular tissue region is dependent upon the imaging of the tissue region. The imaging systems are not limited to a particular type of monitoring. The present invention is not limited to what is being monitored with the imaging devices. In some embodiments, the monitoring is imaging blood perfusion for a particular region so as to detect changes in the region, for example, before, during and after a thermal ablation procedure. In some embodiments, the monitoring includes, but is not limited to, MRI imaging, CT imaging, ultrasound imaging, nuclear medicine imaging, and fluoroscopy imaging. For example, in some embodiments, prior to a thermal ablation procedure, a contrast agent (e.g., iodine or other suitable CT contrast agent; gadolinium chelate or other suitable MRI contrast agent, microbubbles or other suitable ultrasound constrast agent, etc.) is supplied to a subject (e.g., a patient) and the contrast agent perfusing thorugh a particular tissue region that is undergoing the ablation procedure is monitored for blood perfusion changes. In some embodiments, the monitoring is qualitative information about the ablation zone properties (e.g., the diameter, the length, the cross-sectional area, the volume). The imaging system is not limited to a particular technique for monitoring qualitative information. In some embodiments, techniques used to monitor qualitative information include, but are not limited to, non-imaging techniques (e.g., time-domain reflectometry, time-of-flight pulse detection, frequency-modulated distance detection, eigenmode or resonance frequency detection or reflection and transmission at any frequency, based on one interstitial device alone or in cooperation with other interstitial devices or external devices). In some embodiments, the interstitial device provides a signal and/or detection for imaging (e.g., electro-acoustic imaging, electromagnetic imaging, electrical impedance tomography). In some embodiments, non-imaging techniques are used to monitor the dielectric properties of the medium surrounding the antenna, detect an interface between the ablated region and normal tissue through several means, including resonance frequency detection, reflectometry or distance-finding techniques, power reflection/transmission from interstitial antennas or external antennas, etc. In some embodiments, the qualitative information is an estimate of ablation status, power delivery status, and/or simple go/no-go checks to ensure power is being applied. In some embodiments, the imaging systems are designed to automatically monitor a particular tissue region at any desired frequency (e.g., per second intervals, per one-minute intervals, per ten-minute intervals, per hour-intervals, etc.). In some embodiments, the present invention provides software designed to automatically obtain images of a tissue region (e.g., MRI imaging, CT imaging, ultrasound imaging, nuclear medicine imaging, fluoroscopy imaging), automatically detect any changes in the tissue region (e.g., blood perfusion, temperature, amount of necrotic tissue, etc.), and based on the detection to automatically adjust the amount of energy delivered to the tissue region through the energy delivery devices. Likewise, an algorithm may be applied to predict the shape and size of the tissue region to be ablated (e.g., tumor shape) such that the system recommends the type, number, and location of ablation probes to effectively treat the region. In some embodiments, the system is configured to with a navigation or guidance system (e.g., employing triangulation or other positioning routines) to assist in or direct the placement of the probes and their use.

For example, such procedures may use the enhancement or lack of enhancement of a contrast material bolus to track the progress of an ablation or other treatment procedure. Subtraction methods may also be used (e.g., similar to those used for digital subtraction angiography). For example, a first image may be taken at a first time point. Subsequent images subtract out some or all of the information from the first image so that changes in tissue are more readily observed. Likewise, accelerated imaging techniques may be used that apply "under sampling" techniques (in contrast to Nyquist sampling). It is contemplated that such techniques provide excellent signal-to-noise using multiple low resolutions images obtained over time. For example, an algorithm called HYPER (highly constrained projection reconstruction) is available for MRI that may be applied to embodiments of the systems of the invention.

As thermal-based treatments coagulate blood vessels when tissue temperatures exceed, for example, 50° C., the coagulation decreases blood supply to the area that has been completely coagulated. Tissue regions that are coagulated do not enhance after the administration of contrast. In some embodiments, the present invention utilizes the imaging systems to automatically track the progress of an ablation procedure by giving, for example, a small test injection of contrast to determine the contrast arrival time at the tissue region in question and to establish baseline enhancement. In some embodiments, a series of small contrast injections is next performed following commencement of the ablation procedure (e.g., in the case of CT, a series of up to fifteen 10 ml boluses of 300 mgI/ml water soluble contrast is injected), scans are performed at a desired appropriate post-injection time (e.g., as determined from the test injection), and the contrast enhancement of the targeted area is determined using, for example, a region-of-interest (ROI) to track any one of a number of parameters including, but not limited to, attenuation (Hounsfield Units [HU]) for CT, signal (MRI), echogenicity (ultrasound), etc. The imaged data is not limited to a particular manner of presentation. In some embodiments, the imaging data is presented as color-coded or grey scale maps or overlays of the change in attenuation/signal/echogenicity, the difference between targeted and non-targeted tissue, differences in arrival time of the contrast bolus during treatment, changes in tissue perfusion, and any other tissue properties that can be measured before and after the injection of contrast material. The methods of the present invention are not limited to selected ROI's, but can be generalized to all pixels within any image. The pixels can be color-coded, or an overlay used to demonstrate where tissue changes have occurred and are occurring. The pixels can change colors (or other properties) as the tissue property changes, thus giving a near real-time display of the progress of the treatment. This method can also be generalized to 3d/4d methods of image display.

In some embodiments, the area to be treated is presented on a computer overlay, and a second overlay in a different color or shading yields a near real-time display of the progress of the treatment. In some embodiments, the presentation and imaging is automated so that there is a feedback loop to a treatment technology (RF, MW, HIFU, laser, cryo, etc) to modulate the power (or any other control parameter) based on the imaging findings. For example, if the perfusion to a targeted area is decreased to a target level, the power could be decreased or stopped. For example, such embodiments are applicable to a multiple applicator system as the power/time/frequency/duty cycle, etc. is modulated for each individual applicator or element in a phased array system to create a precisely sculpted zone of tissue treatment. Conversely, in some embodiments, the methods are used to select an area that is not to be treated (e.g., vulnerable structures that need to be avoided such as bile ducts, bowel, etc.). In such embodiments, the methods monitor tissue changes in the area to be avoided, and warn the user (e.g., treating physician) using alarms (e.g., visible and/or audible alarms) that the structure to be preserved is in danger of damage. In some embodiments, the feedback loop is used to modify power or any other parameter to avoid continued damage to a tissue region selected not to be treated. In some embodiments, protection of a tissue region from ablation is accomplished by setting a threshold value such as a target ROI in a vulnerable area, or using a computer overlay to define a "no treatment" zone as desired by the user.

V. Tuning Systems

In some embodiments, the energy delivery systems of the present invention utilize tuning elements for adjusting the amount of energy delivered to the tissue region. In some embodiments, the tuning element is manually adjusted by a user of the system. In some embodiments, a tuning system is incorporated into an energy delivery device so as to permit a user to adjust the energy delivery of the device as desired (see, e.g., U.S. Pat. Nos. 5,957,969, 5,405,346; each herein incorporated by reference in their entireties). In some embodiments, the device is pretuned to the desired tissue and is fixed throughout the procedure. In some embodiments, the tuning system is designed to match impedance between a generator and an energy delivery device (see, e.g., U.S. Pat. No. 5,364,392; herein incorporated by reference in its entirety). In some embodiments, the tuning element is automatically adjusted and controlled by a processor of the present invention (see, e.g., U.S. Pat. No. 5,693,082; herein incorporated by reference in its entirety). In some embodiments, a processor adjusts the energy delivery over time to provide constant energy throughout a procedure, taking into account any number of desired factors including, but not limited to, heat, nature and/or location of target tissue, size of lesion desired, length of treatment time, proximity to sensitive organ areas or blood vessels, and the like. In some embodiments, the system comprises a sensor that provides feedback to the user or to a processor that monitors the function of the device continuously or at time points. The sensor may record and/or report back any number of properties, including, but not limited to, heat at one or more positions of a components of the system, heat at the tissue, property of the tissue, and the like. The sensor may be in the form of an imaging device such as CT, ultrasound, magnetic resonance imaging, or any other imaging device. In some embodiments, particularly for research application, the system records and stores the information for use in future optimization of the system generally and/or for optimization of energy delivery under particular conditions (e.g., patient type, tissue type, size and shape of target region, location of target region, etc.).

VI. Temperature Adjustment Systems

In some embodiments, the energy delivery systems of the present invention utilize coolant systems so as to reduce undesired heating within and along an energy delivery device (e.g., tissue ablation catheter). The systems of the present invention are not limited to a particular cooling system mechanism. In some embodiments, the systems are designed to circulate a coolant (e.g., air, liquid, etc.) throughout an energy delivery device such that the coaxial transmission line(s) or triaxial transmission line(s) and antenna(e) temperatures are reduced. In some embodiments, the systems utilize energy delivery devices having therein channels designed to accommodate coolant circulation. In some embodiments, the systems provide a coolant sheath wrapped around the antenna or portions of the antenna for purposes of cooling the antenna externally (see, e.g., U.S. patent application Ser. No. 11/053,987; herein incorporated by reference in its entirety). In some embodiments, a coolant sheath comprises a collapsible material (e.g. boPET) which adopts a low cross-sectional profile when collapsed (e.g. for insertion and/or deployment) and is expanded upon flow of coolant through the sheath (SEE FIGS. 32I and 32J). In some embodiments, a coolant sheath also functions as the outer conductor of a coaxial cable, or the outer or second conductor (middle conductor) of a triaxial cable. In some embodiments, the systems utilize energy delivery devices having a conductive covering around the antenna for purposes of limiting dissipation of heat onto surrounding tissue (see, e.g., U.S. Pat. No. 5,358,515; herein incorporated by reference in its entirety). In some embodiments, upon circulation of the coolant, it is exported into, for example, a waste receptacle. In some embodiments, upon circulation of the coolant it is recirculated. In some embodiments, the coolant is a gas circulated at or near its critical point. In some embodiments, the gas delivered at or near its critical point is carbon dioxide gas. In some embodiments, the energy delivery devices are configured to compress transported coolants (e.g., carbon dioxide gas at or near its critical point) at a desired pressure so as to retain the coolant at or near its critical point.

In some embodiments, the systems utilize expandable balloons in conjunction with energy delivery devices for purposes of urging tissue away from the surface of the antenna(e) (see, e.g., U.S. patent application Ser. No. 11/053,987; herein incorporated by reference in its entirety).

In some embodiments, the systems utilize devices configured to attach onto an energy delivery device for purposes of reducing undesired heating within and along the energy delivery device (see, e.g., U.S. patent application Ser. No. 11/237,430; herein incorporated by reference in its entirety).

In some embodiments, coolant channels may be of any suitable configuration (SEE FIG. 32), and find use with any configuration of energy delivery device and/or system (e.g. coaxial, triaxial, multiple-catheter, etc.). In some embodiments, the dielectric material of a coaxial transmission line (or the dielectric material of the coaxial portion (e.g. inner conductor, dielectric material, second conductor) of a triaxial transmission line) comprises a fluid (e.g. gas (e.g. air, $CO_2$, etc.) or liquid) which also acts as a coolant for the transmission line (SEE FIG. 32A). In some embodiments, the coolant (dielectric material) is flowed through one or more regions between the inner conductor and a second conductor (e.g. outer conductor). In some embodiments, a transmission line comprises one or more coolant channels (e.g. 1 channel, 2 channels, 3, channels, 4 channels, 5 channels, 6 channels, 7, channels, 8 channels, 9 channels, 10 channels, etc.) through which dielectric material and/or coolant is flowed. In some embodiments, coolant channels converge and/or diverge to provide optimal cooling and/or mixing of two or more coolant components (e.g. to provide and endothermic cooling reaction).

In some embodiments, one or more channels provide coolant flow from the proximal end of a device to the distal end (coolant channel), and one or more channels provide coolant from the distal end of a device to the proximal end (e.g. return channel). In some embodiments, cooled dielectric material (e.g. coolant liquid, air, $CO_2$, etc.) is flowed from a pump located near the proximal end of a device or system through one or more coolant channels along the transmission line. In some embodiments, dielectric material flowed to the distal end of a transmission line is transferred to a return channel and flowed back to the proximal end. In some embodiments, dielectric material is capable of cooling a transmission line in both a coolant channel and return channel. In some embodiments, a coolant and/or dielectric material fills a channel without continuous flow. In some embodiments, a coolant and/or dielectric material is pumped into and out of a single channel. In some embodiments, dielectric material absorbs heat generated by energy transmission and carries it away from the transmission line as dielectric material is flowed along the transmission line and out the proximal end. In some embodiments, a porous dielectric material allows coolant to flow (e.g. mono-directionally, bi-directionally, etc.) directly through the dielectric material (SEE FIG. 32H).

In some embodiments, energy delivery devices utilize reduced temperature energy patterns to reduce undesired heating along the length of the transmission line. In some embodiments, constant low power energy transmission provides sufficient energy at the target site (e.g. sufficient for effective tumor ablation) without undue heating along the path of the transmission line. In some embodiments, energy is delivered in a pulse pattern to provide bursts of sufficient energy at the target site (e.g. sufficient for effective tumor ablation) with less heat build-up along the transmission line than continuous delivery. In some embodiments, the length and intensity of the pulse-pattern are set by monitoring temperature along the transmission line or in the tissue surrounding the transmission line. In some embodiments, a pulse pattern is predetermined to balance the amount of energy delivered to the target site with the amount of heat release along the transmission line. In some embodiments, any suitable pulse pattern will find use with the devices, systems, and methods of the present invention. In some embodiments, an ablation algorithm is calculated or determined based on a combination of time (e.g. of treatment, of pulses, of time between pulses), power (e.g. power generated, power delivered, power lost, etc.), and temperature monitoring.

In some embodiments, an energy delivery device comprises a capacitor and/or energy gate at the distal end of the transmission line. The capacitor and/or gate delivers energy (e.g. microwave energy) to the target site once a threshold of energy has built up behind the capacitor and/or gate. Low level energy is delivered along the transmission line, thereby reducing heat build-up along the pathway. Once sufficient energy has built up at the capacitor and/or gate, a high energy burst of energy (e.g. microwave energy) is delivered to the target site. The capacitor and/or gate delivery method has the advantage of reduced heating along the transmission path due to the low level energy transfer, as well as bursts of high energy being delivered at the target site (e.g. sufficient for tumor ablation).

In some embodiments, all or a portion of the energy generating circuitry is located at one or more points along the transmission line. In some embodiments, all or a portion of the microwave generating circuitry is located at one or more points along the transmission line. In some embodiments, generating energy (e.g. microwave energy) at one or more points along the transmission line reduces the distance the energy needs to travel, thereby reducing energy loss, and undesired heat generation. In some embodiments, generating energy (e.g. microwave energy) at one or more points along the transmission line allows for operating at reduced energy levels while providing the same energy level to the treatment site.

VII. Identification Systems

In some embodiments, the energy delivery systems of the present invention utilize identification elements (e.g., RFID elements, identification rings (e.g., fidicials), barcodes, etc.) associated with one or more components of the system. In some embodiments, the identification element conveys information about a particular component of the system. The present invention is not limited by the information conveyed. In some embodiments, the information conveyed includes, but is not limited to, the type of component (e.g., manufacturer, size, energy rating, tissue configuration, etc.), whether the component has been used before (e.g., so as to ensure that non-sterile components are not used), the location of the component, patient-specific information and the like. In some embodiments, the information is read by a processor of the present invention. In some such embodiments, the processor configures other components of the system for use with, or for optimal use with, the component containing the identification element.

In some embodiments, the energy delivery devices have thereon markings (e.g., scratches, color schemes, etchings, painted contrast agent markings, identification rings (e.g., fidicials), and/or ridges) so as to improve identification of a particular energy delivery device (e.g., improve identification of a particular device located in the vicinity of other devices with similar appearances). The markings find particular use where multiple devices are inserted into a patient. In such cases, particularly where the devices may cross each other at various angles, it is difficult for the treating physician to associate which proximal end of the device, located outside of the patient body, corresponds to which distal end of the device, located inside the patient body. In some embodiments, a marking (e.g., a number) a present on the proximal end of the device so that it is viewable by the physician's eyes and a second marking (e.g., that corresponds to the number) is present on the distal end of the device so that it is viewable by an imaging device when present in the body. In some embodiments, where a set of antennas is employed, the individual members of the set are numbered (e.g., 1, 2, 3, 4, etc.) on both the proximal and distal ends. In some embodiments, handles are numbered, a matching numbered detachable (e.g., disposable) antennas are connected to the handles prior to use. In some embodiments, a processor of the system ensures that the handles and antennas are properly matched (e.g., by RFID tag or other means). In some embodiments, where the antenna are disposable, the system provides a warning if a disposable component is attempted to be re-used, when it should have been discarded. In some embodiments, the markings improve identification in any type of detection system including, but not limited to, MRI, CT, and ultrasound detection.

The energy delivery systems of the present invention are not limited to particular types of tracking devices. In some embodiments, GPS and GPS related devices are used. In some embodiments, RFID and RFID related devices are used. In some embodiments, barcodes are used.

In such embodiments, authorization (e.g., entry of a code, scanning of a barcode) prior to use of a device with an identification element is required prior to the use of such a device. In some embodiments, the information element identifies that a components has been used before and sends information to the processor to lock (e.g. block) use of system until a new, sterile component is provided.

VIII. Temperature Monitoring Systems

In some embodiments, the energy delivering systems of the present invention utilize temperature monitoring systems. In some embodiments, temperature monitoring systems are used to monitor the temperature of an energy delivery device (e.g., with a temperature sensor). In some embodiments, temperature monitoring systems are used to monitor the temperature of a tissue region (e.g., tissue being treated, surrounding tissue). In some embodiments, the temperature monitoring systems are designed to communicate with a processor for purposes of providing temperature information to a user or to the processor to allow the processor to adjust the system appropriately. In some embodiments, temperatures are monitored at several points along the antenna to estimate ablation status, cooling status or safety checks. In some embodiments, the temperatures monitored at several points along the antenna are used to determine, for example, the geographical characteristics of the ablation zone (e.g., diameter, depth, length, density, width, etc.) (e.g., based upon the tissue type, and the amount of power used in the energy delivery device). In some embodiments, the temperatures monitored at several points along the antenna are used to determine, for example, the status of the procedure (e.g., the end of the procedure). In some embodiments, temperature is monitored using thermocouples or electromagnetic means through the interstitial antenna. In some embodiments, data collected from temperature monitoring is used to initiate one or more cooling procedures described herein (e.g. coolant flow, lowered power, pulse program, shutoff, etc.).

IX. Procedure Device Hubs

The system of the present invention may further employ one or more additional components that either directly or indirectly take advantage of or assist the features of the present invention. For example, in some embodiments, one or more monitoring devices are used to monitor and/or report the function of any one or more components of the system. Additionally, any medical device or system that might be used, directly or indirectly, in conjunction with the devices of the present invention may be included with the system. Such components include, but are not limited to, sterilization systems, devices, and components, other surgical, diagnostic, or monitoring devices or systems, computer equipment, handbooks, instructions, labels, and guidelines, robotic equipment, and the like.

Figure 13:
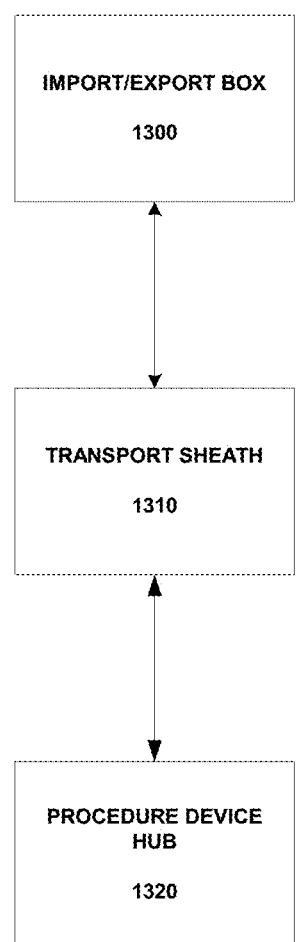
FIG. 13 shows a schematic view of an import/export box, a transport sheath, and a procedure device pod.

In some embodiments, the systems employ pumps, reservoirs, tubing, wiring, or other components that provide materials on connectivity of the various components of the systems of the present invention. For example, any type of pump may be used to supply gas or liquid coolants to the antennas of the present invention. Gas or liquid handling tanks containing coolant may be employed in the system. In some embodiments, more than one tank is used such that as one tank becomes empty, additional tanks will be used automatically so as to prevent a disruption in a procedure (e.g., as one $CO_2$ tank is drained empty, a second $CO_2$ tanks is used automatically thereby preventing procedure disruption). In certain embodiments, the energy delivery systems (e.g., the energy delivery device, the processor, the power supply, the imaging system, the temperature adjustment system, the temperature monitoring system, and/or the identification systems) and all related energy delivery system utilization sources (e.g., cables, wires, cords, tubes, pipes providing energy, gas, coolant, liquid, pressure, and communication items) are provided in a manner that reduces undesired presentation problems (e.g., tangling, cluttering, and sterility compromise associated with unorganized energy delivery system utilization sources). The present invention is not limited to a particular manner of providing the energy delivery systems and energy delivery system utilization sources such that undesired presentation problems are reduced. In some embodiments, as shown in FIG. 13, the energy delivery systems and energy delivery system utilization sources are organized with an import/export box 1300, a transport sheath 1310, and a procedure device pod 1320. In some embodiments, energy delivery systems and energy delivery system utilization sources organized with an import/export box, transport sheath, and procedure device pod provide several benefits. Such benefits include, but are not limited to, decreasing the number of cords traversing between a generator (e.g., a microwave generator) and a patient (e.g., decreasing the number of cords on the floor), de-cluttering the sterile environment and procedure room, increasing patient safety by having the energy delivery systems "move" with a patient thereby preventing device dislodgement (e.g., antenna dislodgement), increasing power delivery efficiency by reducing the energy travel distance within the energy delivery device, and reducing disposable costs by shortening the length of the disposable cables.

The present invention is not limited to a particular type or kind of import/export box. In some embodiments, the import/export box contains the power supply and coolant supply. In some embodiments, the import/export box is located outside of a sterile field in which the patient is being treated. In some embodiments, the import/export box is located outside of the room in which the patient is being treated. In some embodiments, one or more cables connect the import/export box to a procedure device pod. In some embodiments, a single cable is used (e.g., a transport sheath). For example, in some such embodiments, a transport sheath contains components for delivery of both energy and coolant to and/or from the import/export box. In some embodiments, the transport sheath connects to the procedure device pod without causing a physical obstacle for medical practitioners (e.g., travels under the floor, overhead, etc). In some embodiments, the cable is a low-loss cable (e.g., a low-loss cable attaching the power supply to the procedure device hub). In some embodiments, the low-loss cable is secured (e.g., to the procedure device hub, to a procedure table, to a ceiling) so as to prevent injury in the event of accidental pulling of the cable. In some embodiments, the cable connecting the power generator (e.g., microwave power generator) and the procedure device hub is low-loss reusable cable. In some embodiments, the cable connecting the procedure device hub to the energy delivery device is flexible disposable cable.

The present invention is not limited to a particular type or kind of procedure device pod. In some embodiments, the procedure device pod is configured to receive power, coolant, or other elements from the import/export box or other sources. In some embodiments, the procedure device pod provides a control center, located physically near the patient, for any one or more of: delivering energy to a medical device, circulating coolant to a medical device, collecting and processing data (e.g., imaging data, energy delivery data, safety monitoring data, temperature data, and the like), and providing any other function that facilitates a medical procedure. In some embodiments, the procedure device pod is configured to engage the transport sheath so as to receive the associated energy delivery system utilization sources. In some embodiments, the procedure device pod is configured to receive and distribute the various energy delivery system utilization sources to the applicable devices (e.g., energy delivery devices, imaging systems, temperature adjustment systems, temperature monitoring systems, and/or identification systems). For example, in some embodiments, the procedure device pod is configured to receive microwave energy and coolant from energy delivery system utilization sources and distribute the microwave energy and coolant to an energy delivery device. In some embodiments, the procedure device pod is configured to turn on or off, calibrate, and adjust (e.g., automatically or manually) the amount of a particular energy delivery system utilization source as desired. In some embodiments, the procedure device pod has therein a power splitter for adjusting (e.g., manually or automatically turning on, turning off, calibrating) the amount of a particular energy delivery system utilization source as desired. In some embodiments, the procedure device pod has therein software designed to provide energy delivery system utilization sources in a desired manner. In some embodiments, the procedure device pod has a display region indicating associated characteristics for each energy delivery system utilization source (e.g., which devices are presently being used/not used, the temperature for a particular body region, the amount of gas present in a particular $CO_2$ tank, etc.). In some embodiments, the display region has touch capability (e.g., a touch screen). In some embodiments, the processor associated with the energy delivery system is located in the procedure device pod. In some embodiments, the power supply associated with the energy delivery systems is located within the procedure device pod. In some embodiments, the procedure device pod has a sensor configured to automatically inhibit one or more energy delivery system utilization sources upon the occurrence of an undesired event (e.g., undesired heating, undesired leak, undesired change in pressure, etc.). In some embodiments, the weight of the procedure device hub is such that it could be placed onto a patient without causing discomfort and/or harm to the patient (e.g., less than 15 pounds, less than 10 pounds, less than 5 pounds).

The procedure device pods of the present invention are not limited to particular uses or uses within particular settings. Indeed, the procedure device pods are designed for use in any setting wherein the emission of energy is applicable. Such uses include any and all medical, veterinary, and research applications. In addition, the procedure device pods may be used in agricultural settings, manufacturing settings, mechanical settings, or any other application where energy is to be delivered. In some embodiments, the procedure device pods are used in medical procedures wherein patient mobility is not restricted (e.g., CT scanning, ultrasound imaging, etc.).

In some embodiments, the procedure device pod is designed for location within a sterile setting. In some embodiments, the procedure device pod is positioned on a patient's bed, a table that the patient is on (e.g., a table used for CT imaging, ultrasound imaging, MRI imaging, etc.), or other structure near the patient (e.g., the CT gantry). In some embodiments, the procedure device pod is positioned on a separate table. In some embodiments, the procedure device pod is attached to a ceiling. In some embodiments, the procedure device pod is attached to a ceiling such that a user (e.g., a physician) may move it into a desired position (thereby avoiding having to position the energy delivery system utilization sources (e.g., cables, wires, cords, tubes, pipes providing energy, gas, coolant, liquid, pressure, and communication items) on or near a patient while in use). In some embodiments, the procedure device hub is positioned to lay on a patient (e.g., on a patient's legs, thighs, waist, chest). In some embodiments, the procedure device hub is positioned above a patient's head or below a patient's feet. In some embodiments, the procedure device hub has Velcro permitting attachment onto a desired region (e.g., a procedure table, a patient's drape and/or gown).

Figure 18:
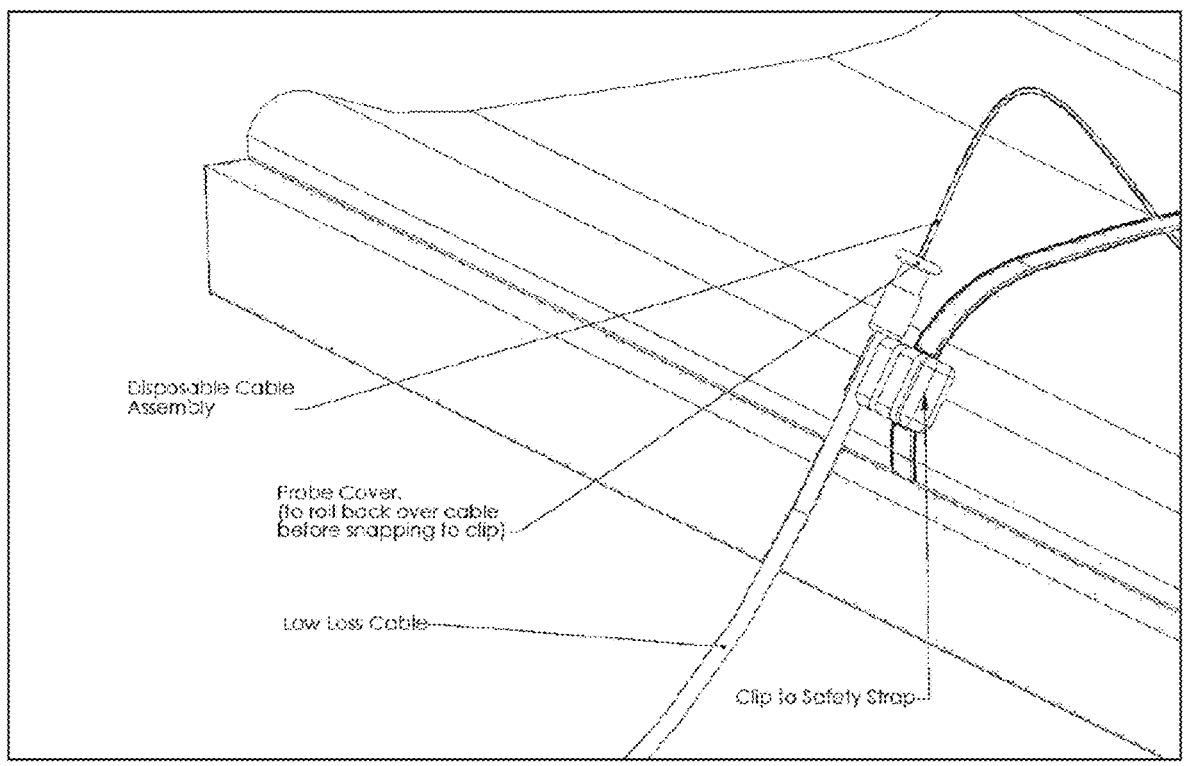
FIG. 18 shows a procedure device hub connected to a procedure table strap.

In some embodiments, the procedure device hub is configured for attachment to a procedure strap used for medical procedures (e.g., a CT safety strap). In some embodiments, the procedure strap attaches to a procedure table (e.g., a CT table) (e.g., through a slot on the sides of the procedure table, through Velcro, through adhesive, through suction) and is used to secure a patient to the procedure table (e.g., through wrapping around the patient and connecting with, for example, Velcro). The procedure device hub is not limited to a particular manner of attachment with a procedure strap. In some embodiments, the procedure device hub is attached to the procedure strap. In some embodiments, the procedure device hub is attached to a separate strap permitting replacement of the procedure strap. In some embodiments, the procedure device hub is attached to a separate strap configured to attach to the procedure strap. In some embodiments, the procedure device hub is attached to a separate strap configured to attach to any region of the procedure table. In some embodiments, the procedure device hub is attached to a separate strap having insulation and/or padding to ensure patient comfort. FIG. 18 shows a procedure device hub connected to a procedure table strap.

In some embodiments, the procedure device hub is configured for attachment to a procedure ring. The present invention is not limited to a particular type or kind of procedure ring. In some embodiments, the procedure ring is configured for placement around a patient (e.g., around a patient's torso, head, feet, arm, etc.). In some embodiments, the procedure ring is configured to attach to a procedure table (e.g., a CT table). The procedure device ring is not limited to a particular shape. In some embodiments, the procedure device ring is, for example, oval, circular, rectangular, diagonal, etc. In some embodiments, the procedure device ring is approximately half of a cyclical shape (e.g., 25% of a cyclical shape, 40% of a cyclical shape, 45% of a cyclical shape, 50% of a cyclical shape, 55 of a cyclical shape, 60 of a cyclical shape, 75 of a cyclical shape). In some embodiments, the procedure ring is, for example, metal, plastic, graphite, wood, ceramic, or any combination thereof. The procedure device hub is not limited to a particular manner of attachment to the procedure ring. In some embodiments, the procedure device hub attaches onto the procedure ring (e.g., with Velcro, with snap-ons, with an adhesive agent). In some embodiments utilizing low-loss cables, the low-loss cables additional attach onto the procedure ring. In some embodiments, the size of the procedure ring can be adjusted (e.g., retracted, extended) to accommodate the size of a patient. In some embodiments, additional items may be attached to the procedure ring. In some embodiments, the procedure ring may be easily moved to and from the vicinity of a patient.

Figure 19:
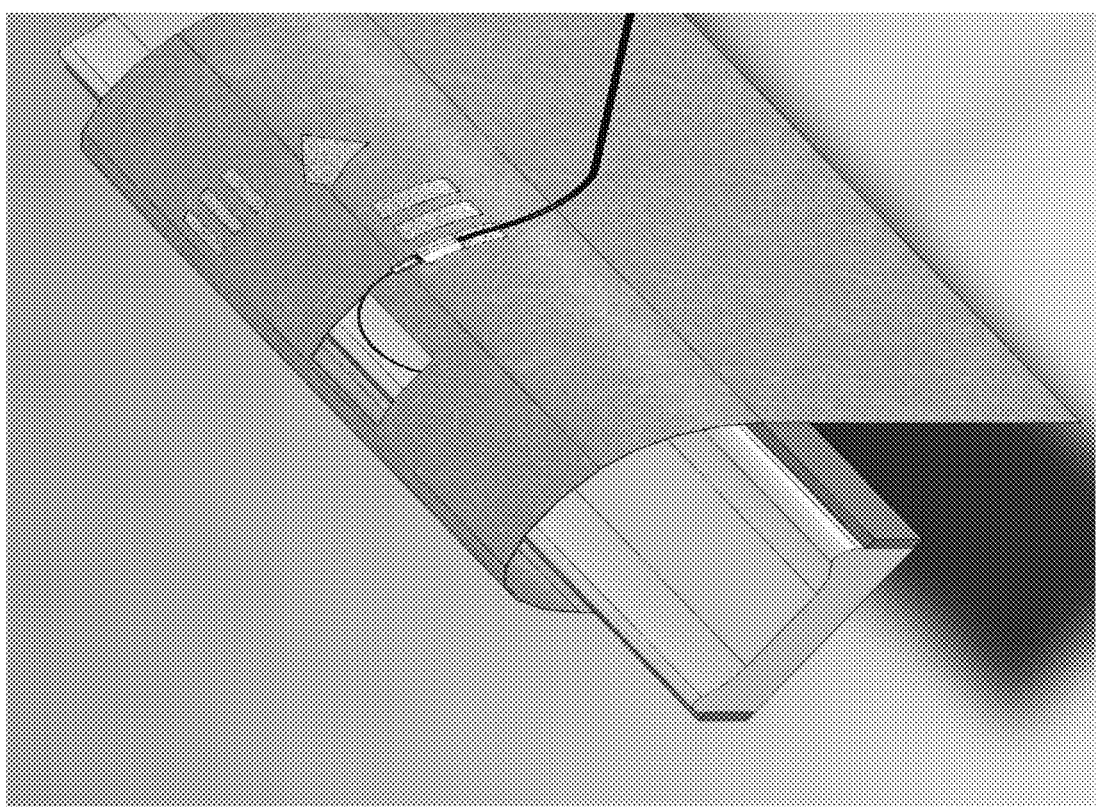
FIG. 19 shows a custom sterile drape with a fenestration and a cable inserted through the fenestration.
Figure 20:
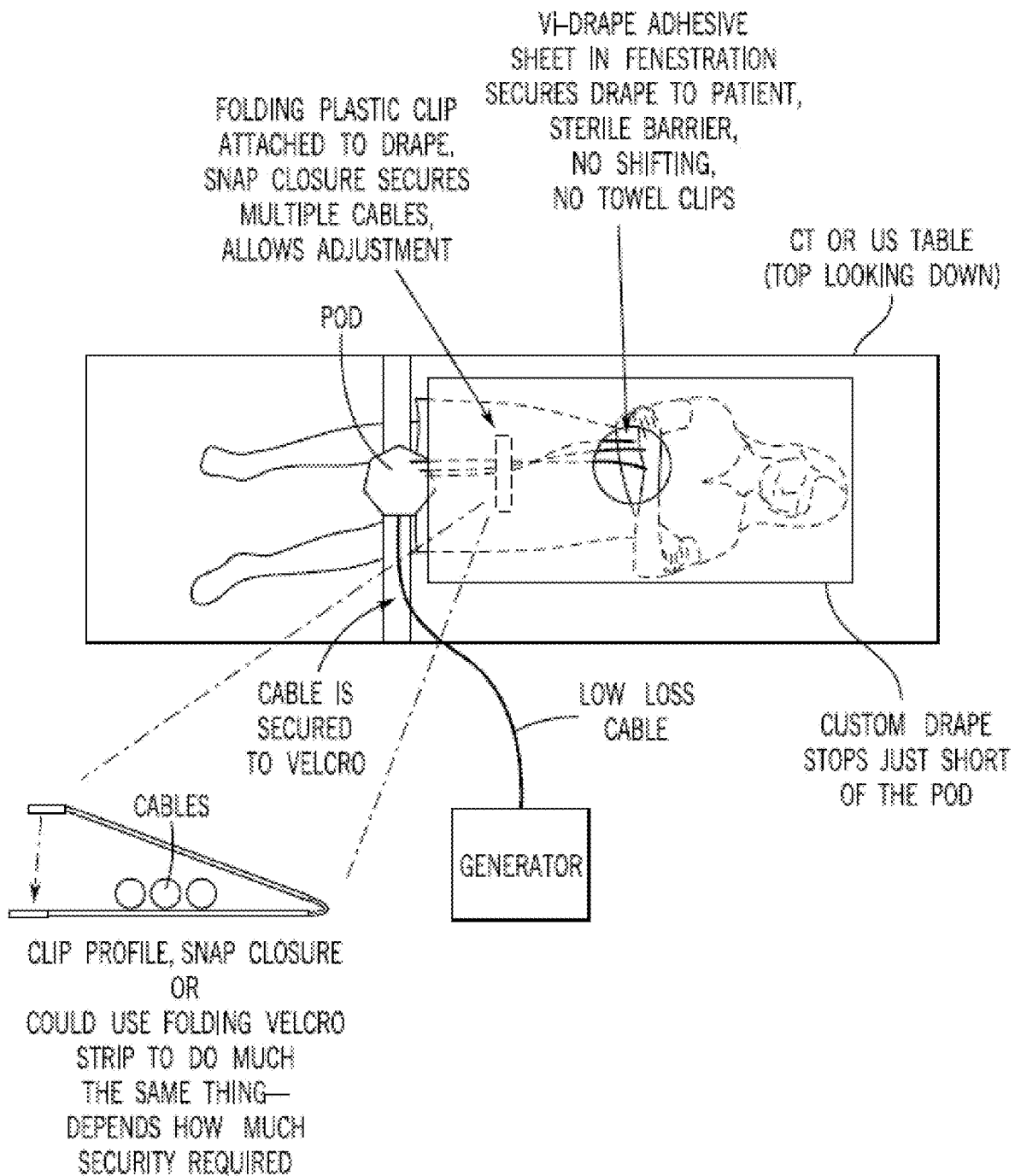
FIG. 20 shows an energy delivery system of the present invention having a generator connected to a procedure device hub via a cable, where the procedure device hub is secured to a procedure table.
Figure 22:
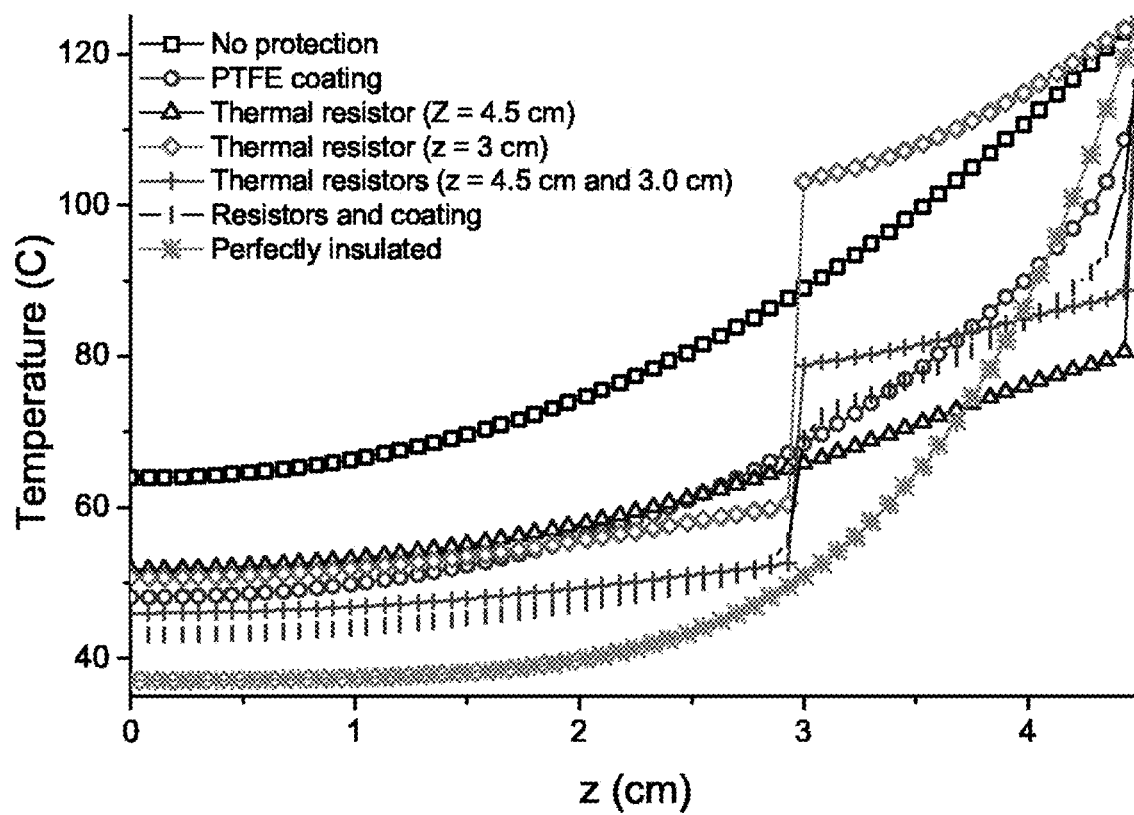
FIG. 22 shows a simulated temperature distribution along an antenna shaft with various passive cooling techniques. A combination of thermal resistors and insulating sheath reduced proximal temperatures most significantly.
Figure 23:
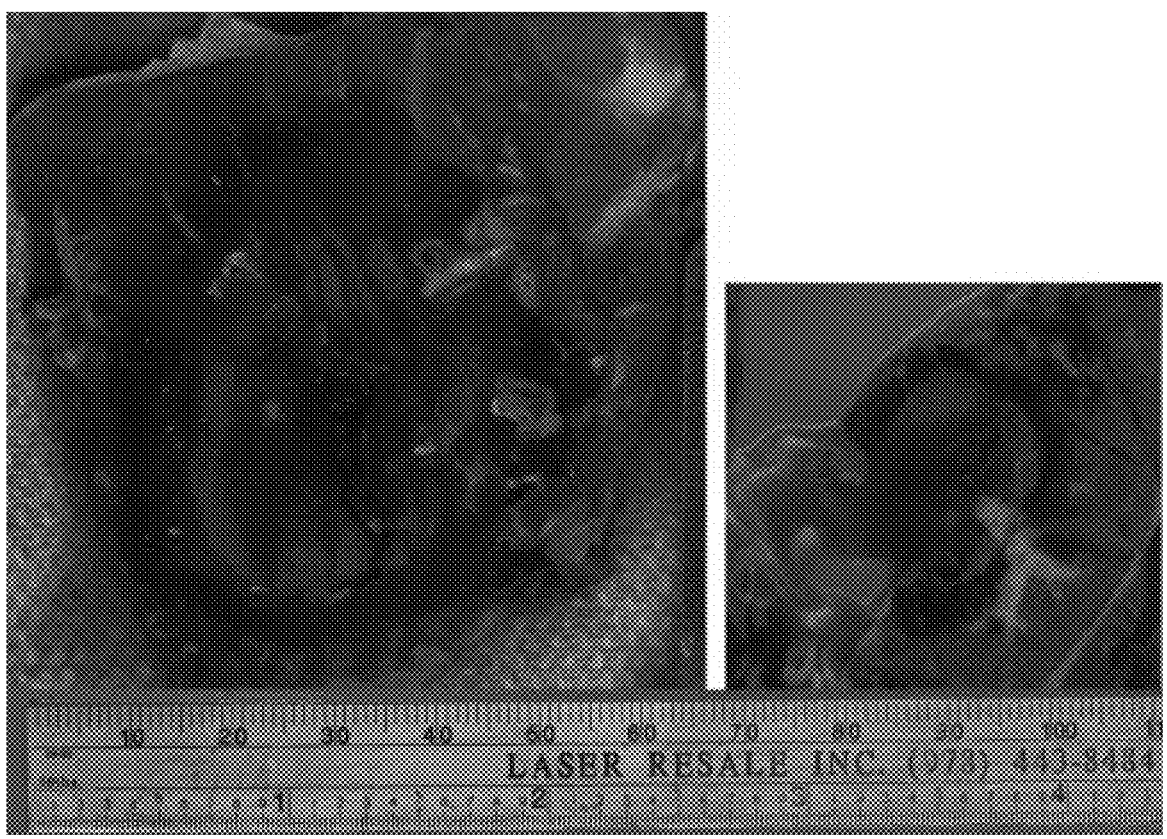
FIG. 23 shows microwave (left) and RF (right) ablations created in 10 min in normal porcine lung shown at equal scale. Microwave ablations were larger and more spherical than RF ablations.

In some embodiments, the procedure device hub is configured for attachment onto a custom sterile drape. The present invention is not limited to a particular type or kind of custom sterile drape. In some embodiments, the custom sterile drape is configured for placement onto a patient (e.g., onto a patient's torso, head, feet, arm, entire body, etc.). In some embodiments, the custom sterile drape is configured to attach to a procedure table (e.g., a CT table). The custom sterile drape is not limited to a particular shape. In some embodiments, the custom sterile drape is, for example, oval, circular, rectangular, diagonal, etc. In some embodiments, the shape of the custom sterile drape is such that it accommodates a particular body region of a patient. In some embodiments, the procedure ring is, for example, cloth, plastic, or any combination thereof. The procedure device hub is not limited to a particular manner of attachment to the custom sterile drape. In some embodiments, the procedure device hub attaches onto the custom sterile drape (e.g., with Velcro, with snap-ons, with an adhesive agent, clamps (e.g., alligator clamps)). In some embodiments utilizing low-loss cables, the low-loss cables additional attach onto the custom sterile drape. In some embodiments, additional items may be attached to the custom sterile drape. In some embodiments, the custom sterile drape may be easily moved to and from the vicinity of a patient. In some embodiments, the custom sterile drape has one more fenestrations for purposes of performing medical procedures. FIG. 19 shows a custom sterile drape with a fenestration and a cable inserted through the fenestration. FIG. 20 shows an energy delivery system of the present invention having a generator connected to a procedure device hub via a cable, where the procedure device hub is secured to a procedure table (e.g., via a procedure table strap). Moreover, as shown in FIG. 20, a custom sterile drape is positioned over a patient lying on the procedure table, where the custom sterile drape has a fenestration.

In some embodiments, the procedure device hub is configured with legs for positioning the hub in the vicinity of a patient. In some embodiments, the procedure device hub has adjustable legs (e.g., thereby allowing positioning of the procedure device hub in a variety of positions). In some embodiments, the procedure device hub has three adjustable legs thereby allowing the device to be positioned in various tri-pod positions. In some embodiments, the legs have therein Velcro permitting attachment onto a desired region (e.g., a procedure table, a patient's drape and/or gown). In some embodiments, the legs are formed from a springy material configured to form an arc over the procedure table (e.g., CT table) and squeeze the rails of the procedure table. In some embodiments, the legs are configured to attach onto the rails of the procedure table.

In some embodiments, the procedure device pod is configured to communicate (wirelessly or via wire) with a processor (e.g., a computer, with the Internet, with a cellular phone, with a PDA). In some embodiments, the procedure device hub may be operated via remote control. In some embodiments, the procedure device pod has thereon one or more lights. In some embodiments, the procedure device hub provides a detectable signal (e.g., auditory, visual (e.g., pulsing light)) when power is flowing from the procedure device hub to an energy delivery device. In some embodiments, the procedure device hub has an auditory input (e.g., an MP3 player). In some embodiments, the procedure device hub has speakers for providing sound (e.g., sound from an MP3 player). In some embodiments, the procedure device hub has an auditory output for providing sound to an external speaker system. In some embodiments, the use of a procedure device pod permits the use of shorter cables, wires, cords, tubes, and/or pipes (e.g., less than 4 feet, 3 feet, 2 feet). In some embodiments, the procedure device pod and/or one more components connected to it, or portions thereof are covered by a sterile sheath. In some embodiments, the procedure device hub has a power amplifier for supplying power (e.g., to an energy delivery device).

In some embodiments, the procedure device pod is configured to compress transported coolants (e.g., $CO_2$) at any desired pressure so as to, for example, retain the coolant at a desired pressure (e.g., the critical point for a gas) so as to improve cooling or temperature maintenance. For example, in some embodiments, a gas is provided at or near its critical point for the purpose of maintaining a temperature of a device, line, cable, or other component at or near a constant, defined temperature. In some such embodiments, a component is not cooled per se, in that its temperature does not drop from a starting temperature (e.g., room temperature), but instead is maintained at a constant temperature that is cooler than where the component would be, but for the intervention. For example, $CO_2$ may be used at or near its critical point (e.g., 31.1 Celsius at 78.21 kPa) to maintain temperature so that components of the system are sufficiently cool enough not to burn tissue, but likewise are not cooled or maintained significantly below room temperature or body temperature such skin in contact with the component freezes or is otherwise damaged by cold. Using such configurations permits the use of less insulation, as there are not "cold" components that must be shielded from people or from the ambient environment. In some embodiments, the procedure device pod has a retracting element designed to recoil used and/or unused cables, wires, cords, tubes, and pipes providing energy, gas, coolant, liquid, pressure, and/or communication items. In some embodiments, the procedure device pod is configured to prime coolants for distribution into, for example, an energy delivery device such that the coolant is at a desired temperature prior to use of the energy delivery device. In some embodiments, the procedure device pod has therein software configured to prime coolants for distribution into, for example, an energy delivery device such that the system is at a desired temperature prior to use of the energy delivery device. In some embodiments, the circulation of coolants at or near critical point permits cooling of the electronic elements of the energy delivery devices without having to use additional cooling mechanisms (e.g., fans).

In one illustrative embodiment, an import/export box contains one or more microwave power sources and a coolant supply (e.g., pressurized carbon dioxide gas). This import/export box is connected to a single transport sheath that delivers both the microwave energy and coolant to a procedure device pod. The coolant line or the energy line within the transport sheath may be wound around one another to permit maximum cooling of the transport sheath itself. The transport sheath is run into the sterile field where a procedure is to take place along the floor in a location that does not interfere with the movement of the medical team attending to the patient. The transport sheath connects to a table located near an imaging table upon which a patient lays. The table is portable (e.g., on wheels) and connectable to the imaging table so that they move together. The table contains arm, which may be flexible or telescoping, so as to permit positioning of the arm above and over the patient. The transport sheath, or cables connected to the transport sheath, run along the arm to the overhead position. At the end of the arm is the procedure device pod. In some embodiments, two or more arms are provided with two or more procedure device pods or two or more sub-components of a single procedure device pod. The procedure device pod is small (e.g., less than 1 foot cube, less than 10 cm cube, etc.) to allow easy movement and positioning above the patient. The procedure device pod contains a processor for controlling all computing aspects of the system. The device pod contains one or more connections ports for connecting cables that lead to energy delivery devices. Cables are connected to the ports. The cables are retractable and less than three feet in length. Use of short cables reduces expense and prevents power loss. When not in use, the cables hang in the air above the patient, out of contact with the patient's body. The ports are configured with a dummy load when not in use (e.g., when an energy delivery device is not connected to a particular port). The procedure device pod is within reach of the treating physician so that computer controls can be adjusted and displayed information can be viewed, in real-time, during a procedure.

X. Uses for Energy Delivery Systems

The systems of the present invention are not limited to particular uses. Indeed, the energy delivery systems of the present invention are designed for use in any setting wherein the emission of energy is applicable. Such uses include any and all medical, veterinary, and research applications. In addition, the systems and devices of the present invention may be used in agricultural settings, manufacturing settings, mechanical settings, or any other application where energy is to be delivered.

In some embodiments, the systems are configured for open surgery, percutaneous, intravascular, intracardiac, endoscopic, intraluminal, laparoscopic, or surgical delivery of energy. In some embodiments, the energy delivery devices may be positioned within a patient's body through a catheter, through a surgically developed opening, and/or through a body orifice (e.g., mouth, ear, nose, eyes, vagina, penis, anus) (e.g., a N.O.T.E.S. procedure). In some embodiments, the systems are configured for delivery of energy to a target tissue or region. In some embodiments, a positioning plate is provided so as to improve percutaneous, intravascular, intracardiac, laparoscopic, and/or surgical delivery of energy with the energy delivery systems of the present invention. The present invention is not limited to a particular type and/or kind of positioning plate. In some embodiments, the positioning plate is designed to secure one or more energy delivery devices at a desired body region for percutaneous, intravascular, intracardiac, laparoscopic, and/or surgical delivery of energy. In some embodiments, the composition of the positioning plate is such that it is able to prevent exposure of the body region to undesired heat from the energy delivery system. In some embodiments, the plate provides guides for assisted positioning of energy delivery devices. The present invention is not limited by the nature of the target tissue or region. Uses include, but are not limited to, treatment of heart arrhythmia, tumor ablation (benign and malignant), control of bleeding during surgery, after trauma, for any other control of bleeding, removal of soft tissue, tissue resection and harvest, treatment of varicose veins, intraluminal tissue ablation (e.g., to treat esophageal pathologies such as Barrett's Esophagus and esophageal adenocarcinoma), treatment of bony tumors, normal bone, and benign bony conditions, intraocular uses, uses in cosmetic surgery, treatment of pathologies of the central nervous system including brain tumors and electrical disturbances, sterilization procedures (e.g., ablation of the fallopian tubes) and cauterization of blood vessels or tissue for any purposes. In some embodiments, the surgical application comprises ablation therapy (e.g., to achieve coagulative necrosis). In some embodiments, the surgical application comprises tumor ablation to target, for example, metastatic tumors. In some embodiments, the device is configured for movement and positioning, with minimal damage to the tissue or organism, at any desired location, including but not limited to, the lungs, brain, neck, chest, abdomen, and pelvis. In some embodiments, the systems are configured for guided delivery, for example, by computerized tomography, ultrasound, magnetic resonance imaging, fluoroscopy, and the like.

In certain embodiments, the present invention provides methods of treating a tissue region, comprising providing a tissue region and a system described herein (e.g., an energy delivery device, and at least one of the following components: a processor, a power supply, a temperature monitor, an imager, a tuning system, a temperature reduction system, and/or a device placement system); positioning a portion of the energy delivery device in the vicinity of the tissue region, and delivering an amount of energy with the device to the tissue region. In some embodiments, the tissue region is a tumor. In some embodiments, the delivering of the energy results in, for example, the ablation of the tissue region and/or thrombosis of a blood vessel, and/or electroporation of a tissue region. In some embodiments, the tissue region is a tumor. In some embodiments, the tissue region comprises one or more of the lung, heart, liver, genitalia, stomach, lung, large intestine, small intestine, brain, neck, bone, kidney, muscle, tendon, blood vessel, prostate, bladder, and spinal cord.

In some embodiments, the present invention provides systems that access to a difficult to reach region of the body (e.g. the periphery of the lungs). In some embodiments, the system navigates through a branched body structure (e.g. bronchial tree) to reach a target site. In some embodiments, systems, devices, and methods of the present invention provide delivery of energy (e.g. microwave energy, energy for tissue ablation) to difficult to reach regions of a body, organ, or tissue (e.g. the periphery of the lungs). In some embodiments, the system delivers energy (e.g. microwave energy, energy for tissue ablation) to a target site though a branched structure (e.g. bronchial tree). In some embodiments, the system delivers energy (e.g. microwave energy, energy for tissue ablation) to the periphery of the lungs through the bronchi (e.g. primary bronchi, secondary bronchi, tertiary bronchi, bronchioles, etc.). In some embodiments, accessing the lungs through the bronchi provides a precise and accurate approach while minimizing collateral damage to the lungs. Accessing the lung (e.g. lung periphery) from outside the lung requires puncturing or cutting the lung, which can be avoided by bronchial access. Insertion through the lung has medical complications that are avoided by the systems and methods of embodiments of the present invention.

In some embodiments, a primary catheter (e.g. endoscope, bronchoscope, etc.), containing a channel catheter and steerable navigation catheter is advanced into the bronchial tree (e.g. via the trachea) until the decreasing circumference of the bronchi will not allow further advancement of the primary catheter. In some embodiments, a primary catheter (e.g. endoscope, bronchoscope, etc.), containing a channel catheter and steerable navigation catheter is advanced into the bronchial tree (e.g. via the trachea) up to the desired point for deployment of the channel catheter. In some embodiments, the primary catheter is advanced into the trachea, primary bronchi, and/or secondary bronchi, but not further. In some embodiments, a channel catheter containing a steerable navigation catheter is advanced through the primary catheter, and beyond the distal tip of the primary catheter, into the bronchial tree (e.g. via the trachea, via the primary bronchi, via secondary bronchi, via tertiary bronchi, via bronchioles, etc.) up to the target location (e.g. treatment site, tumor, etc.). In some embodiments, a channel catheter containing a steerable navigation catheter is advanced into the bronchial tree (e.g. via the trachea, primary bronchi, etc.) until the decreasing size of the bronchi will not allow further advancement (e.g. in the tertiary bronchi, in the bronchioles, at the treatment site). In some embodiments, the channel catheter is advanced into the trachea, primary bronchi, secondary bronchi, tertiary bronchi, and/or bronchioles. In some embodiments, the steerable navigation catheter is advanced into the trachea, primary bronchi, secondary bronchi, tertiary bronchi, and/or bronchioles to the treatment site. In some embodiments, the steerable navigation catheter is withdrawn through the channel catheter, leaving the open channel lumen extending from the point of insertion (e.g. into the subject, into the trachea, into the bronchial tree, etc.), through the bronchial tree (e.g. through the trachea, primary bronchi, secondary bronchi, tertiary bronchi, bronchioles, etc.) to the target site (e.g. treatment site, tumor, peripheral lunch tumor). In some embodiments, an energy delivery device (e.g. microwave ablation device) is inserted through the open channel lumen to access the target site. In some embodiments, the present invention provides systems, devices, and method to access peripheral lung tumors through the bronchial tree with a microwave ablation device.

In some embodiments, the present invention provides systems, methods, and devices for placement of an energy delivery device at a difficult to access tissue region within a subject. In some embodiments, the present invention provides placement of an energy delivery device for tissue ablation therapy (e.g. tumor ablation). In some embodiments, the present invention provides access to, and/or treatment of, tumors, growths, and/or nodules on the periphery of the lungs. In some embodiments, the present invention provides access to, and ablation of, peripheral pulmonary nodules. Peripheral pulmonary nodules are difficult to access through the bronchial tree because of their location near the tertiary bronchi and bronchioles, beyond the reach of conventional devices and techniques. In some embodiments, devices, systems, and methods of the present invention provide access to peripheral pulmonary nodules through the bronchial tree. Peripheral pulmonary nodules are generally less than 25 mm in diameter (e.g. <25 mm, <20 mm, <10 mm, <5 mm, <2 mm, <1 mm, etc.). In some embodiments, peripheral pulmonary nodules are 0.1 mm-25 mm in diameter (e.g. 0.1 mm . . . 0.2 mm . . . 0.5 mm . . . 1.0 mm . . . 1.4 mm . . . 2.0 mm . . . 5.0 mm . . . 10 mm . . . 20 mm . . . 25 mm, and diameters therein). In some embodiments, the present invention provides access and treatment of tumors, growths, and nodules of any size and any location within a subject (e.g. within the lungs of a subject). In some embodiments, the present invention provides curative treatment and/or palliative treatment of tumors (e.g. nodules) in the peripheral lung.

XI. Device Placement Systems

In some embodiments, the present invention provides a primary catheter (e.g. endoscope, bronchoscope, etc.). In some embodiments, any suitable endoscope or bronchoscope known to those in the art finds use as a primary catheter in the present invention. In some embodiments, a primary catheter adopts characteristics of one or more endoscopes and/or bronchoscopes known in the art, as well as characteristics described herein. One type of conventional flexible bronchoscope is described in U.S. Pat. No. 4,880,015, herein incorporated by reference in its entirety. The bronchoscope measures 790 mm in length and has two main parts, a working head and an insertion tube. The working head contains an eyepiece; an ocular lens with a diopter adjusting ring; attachments for suction tubing, a suction valve, and light source; and an access port or biopsy inlet, through which various devices and fluids can be passed into the working channel and out the distal end of the bronchoscope. The working head is attached to the insertion tube, which typically measures 580 mm in length and 6.3 mm in diameter. The insertion tube contains fiberoptic bundles, which terminate in the objective lens at the distal tip, light guides, and a working channel. Other endoscopes and bronchoscopes which may find use in embodiments of the present invention, or portions of which may find use with the present invention, are described in U.S. Pat. Nos. 7,473,219; 6,086,529; 4,586,491; 7,263,997; 7,233,820; and 6,174,307.

In some embodiments, the present invention provides a channel catheter (a.k.a. guide catheter, sheath, sheath catheter, etc.). In some embodiments, a guide catheter is configured to fit within the lumen of a primary catheter and contains a channel lumen of sufficient diameter (e.g. 1 mm . . . 2 mm . . . 3 mm . . . 4 mm . . . 5 mm) to accommodate a steerable navigation catheter and/or one or more suitable tools (e.g. energy delivery device). In some embodiments, a channel catheter is of sufficient length to extend from an insertion site (e.g. mouth, incision into body of subject, etc.) through the trachea and/or bronchial tree to a treatment site in the peripheral lung (e.g. 50 cm . . . 75 cm . . . 1 m . . . 1.5 m . . . 2 m). In some embodiments, a channel catheter is of sufficient length to extend beyond the reach of a primary catheter to reach a treatment site (e.g. peripheral lung tissue). In some embodiments, a channel catheter is highly flexible to access a circuitous route through a subject (e.g. through a branched structure, through the bronchial tree, etc.). In some embodiments, a channel catheter is constructed of braided material to provide both strength and flexibility, as is understood in the art. In some embodiments, a channel catheter comprises the outer conductor of a triaxial transmission line. In some embodiments, a channel catheter comprises a navigation and/or steering mechanism. In some embodiments, a channel catheter is without an independent means of navigation, position recognition, or maneuvering. In some embodiments, a channel catheter relies upon the primary catheter or steerable navigation catheter for placement.

In some embodiments, the present invention provides a steerable navigation catheter. In some embodiments, a steerable navigation catheter is configured to fit within the lumen of a channel catheter. In some embodiments, a steerable navigation catheter has a similar diameter to energy transmission lines described herein (e.g. 0.2 mm . . . 0.5 mm . . . 1.0 mm . . . 1.5 mm . . . 2.0 mm). In some embodiments, a steerable navigation catheter is of sufficient length to extend from an insertion site (e.g. mouth, incision into body of subject, etc.) to a treatment site (e.g. through the trachea and/or bronchial tree to a treatment site in the peripheral lung (e.g. 50 cm . . . 75 cm . . . 1 m . . . 1.5 m . . . 2 m). In some embodiments, a channel catheter is of sufficient length to extend beyond the reach of a primary catheter to reach a treatment site (e.g. peripheral lung tissue). In some embodiments, a steerable navigation catheter engages a channel catheter such that movement of the steerable navigation catheter results in synchronous movement of the channel catheter. In some embodiments, as a steerable navigation catheter is inserted along a path in a subject, the channel catheter surrounding the steerable navigation catheter moves with it. In some embodiments, a channel catheter is placed within a subject by a steerable navigation catheter. In some embodiments, a steerable navigation catheter can be disengaged from a channel catheter. In some embodiments, disengagement of a steerable navigation catheter and channel catheter allows movement of the steerable navigation catheter further along a pathway without movement of the channel catheter. In some embodiments, disengagement of a steerable navigation catheter and channel catheter allows retraction of the steerable navigation catheter through the channel catheter without movement of the channel catheter.

In some embodiments, all inserted components of a system or device are configured for movement along a narrow and circuitous path through a subject (e.g. through a branched structure, through the bronchial tree, etc.). In some embodiment, components comprise a flexible material configured for tight turning radiuses. In some embodiment, necessarily rigid components are reduced in size (e.g. short length) to allow for tight turning radiuses.

EXPERIMENTAL

Example I

Figure 9:
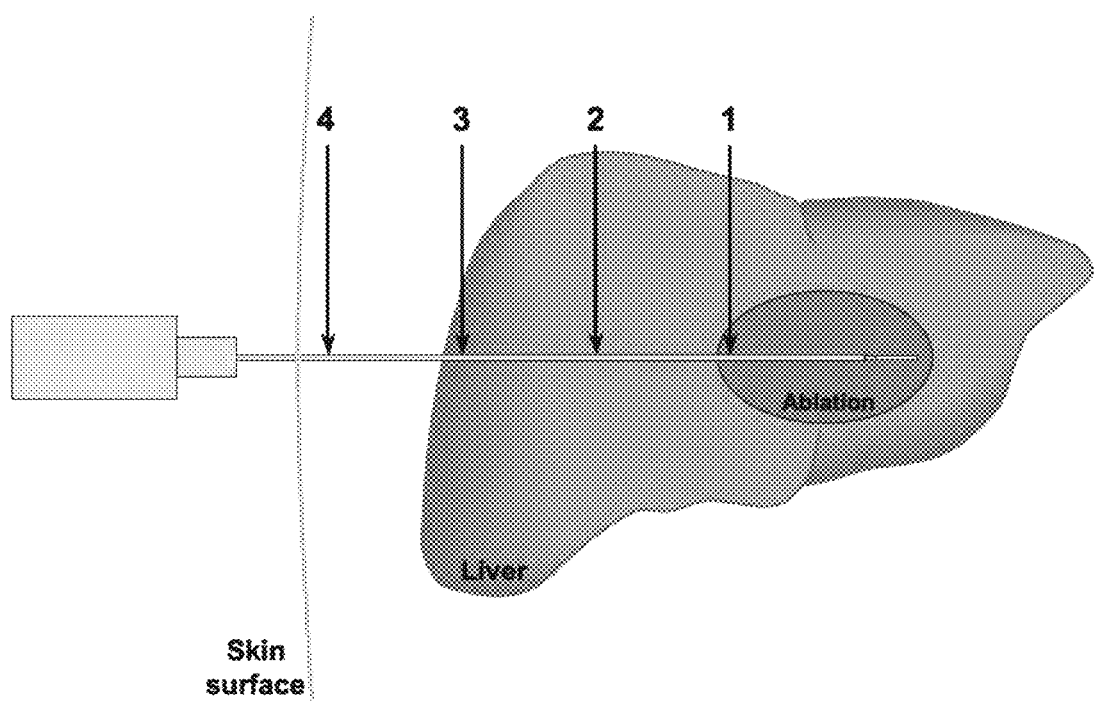
FIG. 9 shows the test setup and position of temperature measurement stations. As shown, the ablation needle shaft for all experiments was 20.5 cm. Probes 1, 2 and 3 were located 4, 8 and 12 cm proximal to the tip of the stainless needle.

This example demonstrates the avoidance of undesired tissue heating through use of an energy delivery device of the present invention circulating coolant through coolant channels. The ablation needle shaft for all experiments was 20.5 cm. There was minimal cooling of the handle assembly indicating that handle-cooling effects were well-isolated. Temperature probes 1, 2 and 3 were located at 4, 8 and 12 cm proximal to the tip of the stainless needle (see FIG. 9). Temperature measurements were taken for 35% power measurement following insertion into a pig liver and 45% power measurement following insertion into a pig liver. For the 35% power measurement, Probe 4 was on the handle itself. For the 45% power measurements, Probe 4 was located at the needle-skin interface, approximately 16 cm back from the stainless needle tip.

Figure 10:
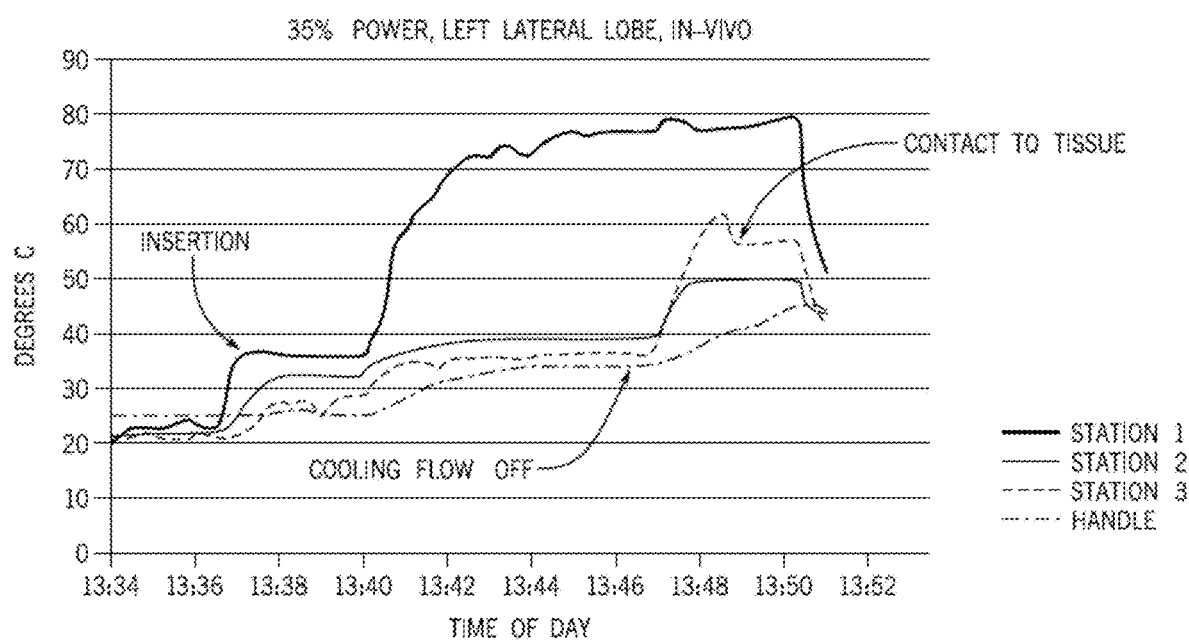
FIG. 10 shows treatment at 35% (microwaves "on" from 13:40 to 13:50) with anomalously high (6.5%) reflected power. Probe 3 was initially placed just outside of the liver tissue, in air.

As shown in FIG. 10, treatment at 35% power for 10 minutes with anonymously high (6.5%) reflected power demonstrated maintenance of the device at a non-tissue damaging temperature at Probes 1, 2, 3 and the handle.

Figure 11:
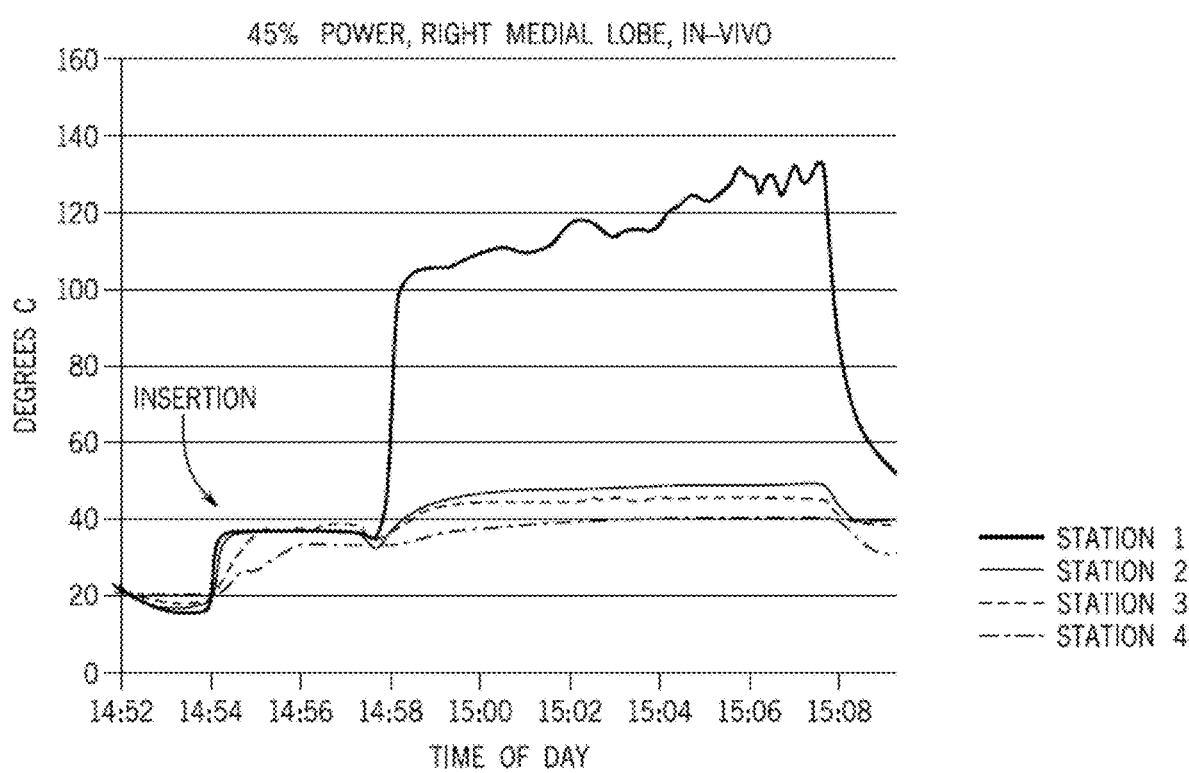
FIG. 11 shows 10 minute treatment at 45% (microwaves on from 14:58 to 15:08) with anomalously high (6.5%) reflected power. Peak temperature at Station 4 was 40.25° C.
Figure 12:
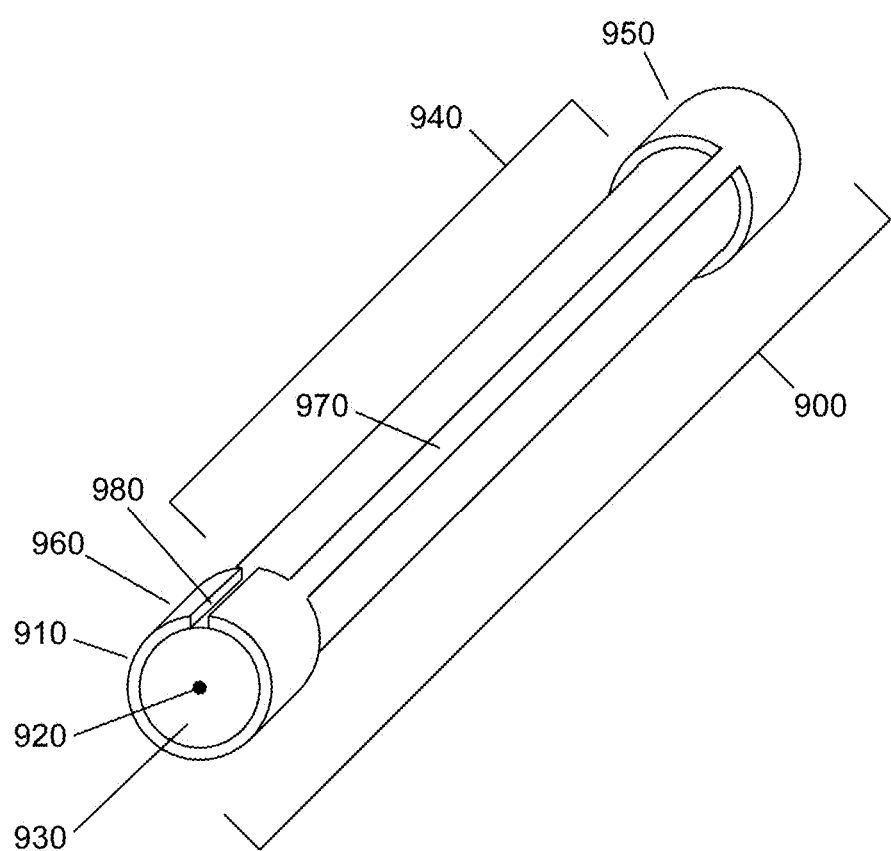
FIG. 12 shows one a coaxial cable having a region of its outer conductor removed to create space for coolant flow in one embodiment of the present invention.

As shown in FIG. 11, treatment at 45% power for 10 minutes with anonymously high (6.5%) reflected power demonstrated maintenance of the device at a non-tissue damaging temperature at Probes 1, 2, 3 and 4. Observation of the skin and fat layers after 10 minutes ablation at 45% power for 10 minutes with anonymously high (6.5%) reflected power demonstrating no visible burns or thermal damage.

Example II

This example demonstrates generator calibration. Generator calibration was done by Cober-Muegge at the factory and was set to be most accurate for powers greater than 150 W. The magnetron behaved much like a diode: increasing cathode voltage did not increase vacuum current (proportional to output power) until a critical threshold was reached, at which point vacuum current increased rapidly with voltage. Control of the magnetron source relied on accurate control of the cathode voltage near that critical point. As such, the generator was not specified for powers from 0-10% and correlation between the output power and theoretical power percentage input was poor below 15%.

To test the generator calibration, the power control dial was changed from 0.25% in 1% increments (corresponding to theoretical output powers of 0-75 W in 3 W increments) and the generator's output power display was recorded and power output measured. The measured power output was adjusted for the measured losses of the coaxial cable, coupler and load at room temperature. The output display was also adjusted for offset error (i.e., the generator read 2.0% when the dial was set to 0.0%).

The error between the dial and generator output power display was large for low-power dial settings. These two values quickly converged to a percent error of less than 5% for dial settings above 15%. Similarly, the measured output power was significantly different from the theoretical output power for dial settings below 15% but more accurate for dial settings above 15%.

Example III

This example describes the setup and testing of an antenna during manufacturing. This provides a method for setup and tested in a manufacturing environment. The method employs a liquid, tissue-equivalent phantom rather than tissue.

From the numerical and experimental measurements already made on the antenna, it was known that changes in L2 of ~1 mm will increase the reflected power from <−30 dB to ~−20-25 dB. This increase was likely made less significant by the changes in tissue properties that occurred during ablation and so we would consider at relative tolerance of 0.5 mm on the length L2 is reasonable. Likewise, a tolerance of 0.5 mm on the length L1 is used, even though the total reflection coefficient depends less on L1 than L2.

Testing of the antenna tuning for quality control purposes can be achieved using a liquid solution designed to mimic the dielectric properties of liver, lung or kidney (see, e.g., Guy A W (1971) IEEE Trans. Microw. Theory Tech. 19:189-217; herein incorporated by reference in its entirety). The antenna is immersed in the phantom and the reflection coefficient recorded using a 1-port measurement device or full vector network analyzer (VNA). Verification of a reflection coefficient below −30 dB is selected to ensure proper tuning.

Example IV

This example compared the efficiency, heating ability, and manufacturability of the triaxial and center-fed dipole antennas. Modification of the original triaxial design was required to create a more rigid, sharp tip that could be easily inserted. Computer modeling was initially used to determine what changes in antenna length might be required with the addition of an alumina sheath and faceted metallic tip. After modeling confirmed that the antenna would need to be lengthened and the metallic tip would not degrade performance, antennas were constructed for testing in ex vivo liver tissue. This testing showed that the modified design retained its high efficiency while providing enough mechanical strength for percutaneous placement. Computer modeling of the center-fed dipole design yielded marginal results and subsequent device fabrication proved difficult to reproduce. Accordingly, the insertable triaxial device was chosen as a lead antenna design.

Computer modeling revealed that both thermally-resistive coatings and serious thermal breaks can reduce the amount of heat that is allowed to flow from the distal antenna tip to proximal sections of the antenna. However, an effective water cooling solution was able to increase the power throughput of a 0.020" coaxial cable from ~8 W to over 150 W. Water cooling also eliminated any shaft heating extending proximally from the antenna tip when using 150 W input power (FIG. 21). However, implementation required the use of expensive 0.020" coaxial cable to provide sufficient water flow rates (~30 ml/min). In addition, 0.020" cable is 2-3× more lossy than the 0.047" cable used previously, which decreased power throughput by as much as 15 W and required cooling of that additional power loss. The final antenna design incorporated a PEEK sheath around the entire assembly to reduce sticking that can occur between a metallic antenna and surrounding tissue while also providing the thermal buffer shown to reduce thermally conductive heating.

A study was performed percutaneously using either the cooled, 17-gauge prototype antenna or 17-gauge cooled RF electrode from Valleylab/Covidien to create ablations in a normal, in vivo porcine lung model. Ablations were performed for 10 min using the clinical standard of 200 W with impedance control for RF and 135 W for the microwave group. Ablations created in the microwave group were significantly larger than in the RF group with a mean ablation diameter (mean±standard deviation) of 3.32±0.19 cm and 2.7±0.27 cm, respectively ($P<0.0001$, FIG. 9). Ablation circularity was also significantly higher in the microwave group than in the RF group (0.90±0.06 vs. 0.82±0.09, $P<0.05$). No major complications were observed throughout the entire study. Minor pneumothoraces were observed in one animal during two ablations, both from the RF group. Both remained stable without intervention. From this study, it was concluded that microwaves are more effective and typically faster than RF current for heating lung tissue.

Example V

Figure 24:
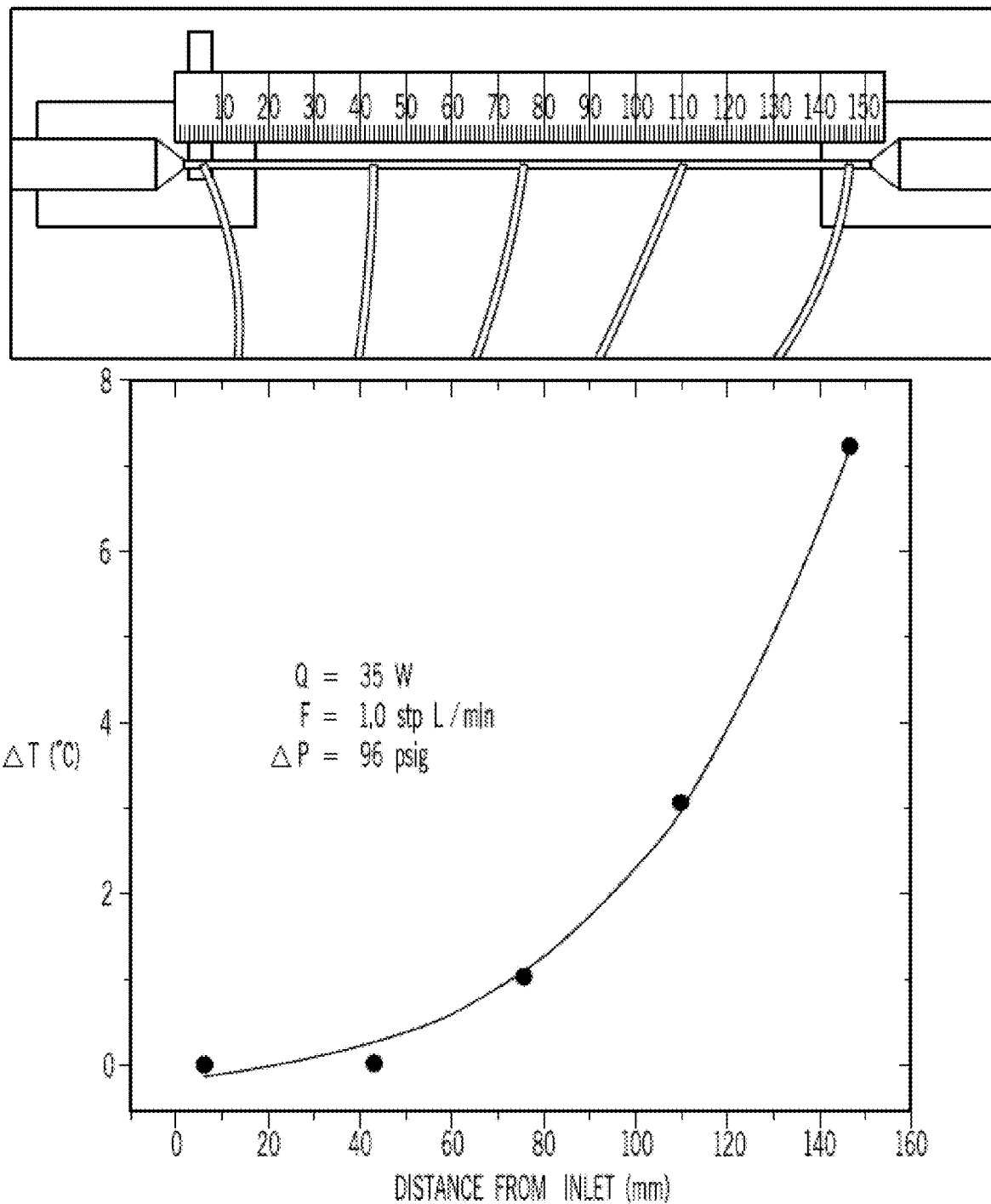
FIG. 24 shows the experimental setup (top) and results for temperatures measured along an antenna shaft while 35 W of heat are generated inside the antenna shaft (bottom). Only 1.0 stp L/min $CO_2$ flow was required to keep temperatures from rising more than 8° C. at any point along the shaft. 10 stp L/min was able to offset 50 W of heating power.

This example investigated cooling in a simulated heating environment. A heater coil was passed through a 17-gauge stainless needle nearly identical to the third conductor of the triaxial antenna. Four thermocouples were placed along the outside of the needle and the entire system thermally isolated with closed-cell foam. This setup was considered worst-case, since blood flow and the high thermal conductivity of biological tissues will tend to provide some antenna cooling. The coil was heated with 0-50 W and temperatures recorded with $NC-CO_2$ operating at 0-10 stp L/min flow rates. Test results showed that a moderate flow of $CO_2$ was sufficient to cool the entire 50 W input power so that the heated tube remained at ambient temperature (FIG. 24).

Temperatures recorded on the outer surface of the needle without cooling present exceeded 100° C., but cooling with 10-20 stp L/min of $NC-CO_2$ reduced the surface temperature to below 30° C. (FIG. 24). These tests showed that moderate amounts of NC—$CO_2$ (~10 stp L/min) can effectively cool as much as 50 W from the inside of an ablation antenna.

Example VI

This experiment measured the effects of thermal conduction proximally from the heated antenna tip. A modified antenna—with the ceramic radiating segment replaced with a thermally-conductive copper tube—was placed into an electric heater with thermal paste to ensure a good thermal contact between the heater and antenna (FIG. 25). Thermocouples were placed along the outer surface of the antenna at several points to measure temperature versus NC—$CO_2$ flow rate.

Before cooling, temperatures along the outer conductor exceeded 80° C. 1 cm proximal to the heater. When cooling was initiated even at a modest rate of 13 stp L/min, temperatures dropped to the input temperature of the NC—$CO_2$ gas: ~0° C. (FIG. 25). Increasing the flow rate decreased temperatures even further. Gas was precooled slightly in a heat-exchanger to test the possibility of a "stick" function on the needle shaft, similar to that employed by cryoablation probes. This precooling led to the lower-than-required temperature of 31° C. for near-critical operation and additional implementation was beyond the scope of this investigation.

Figure 26:
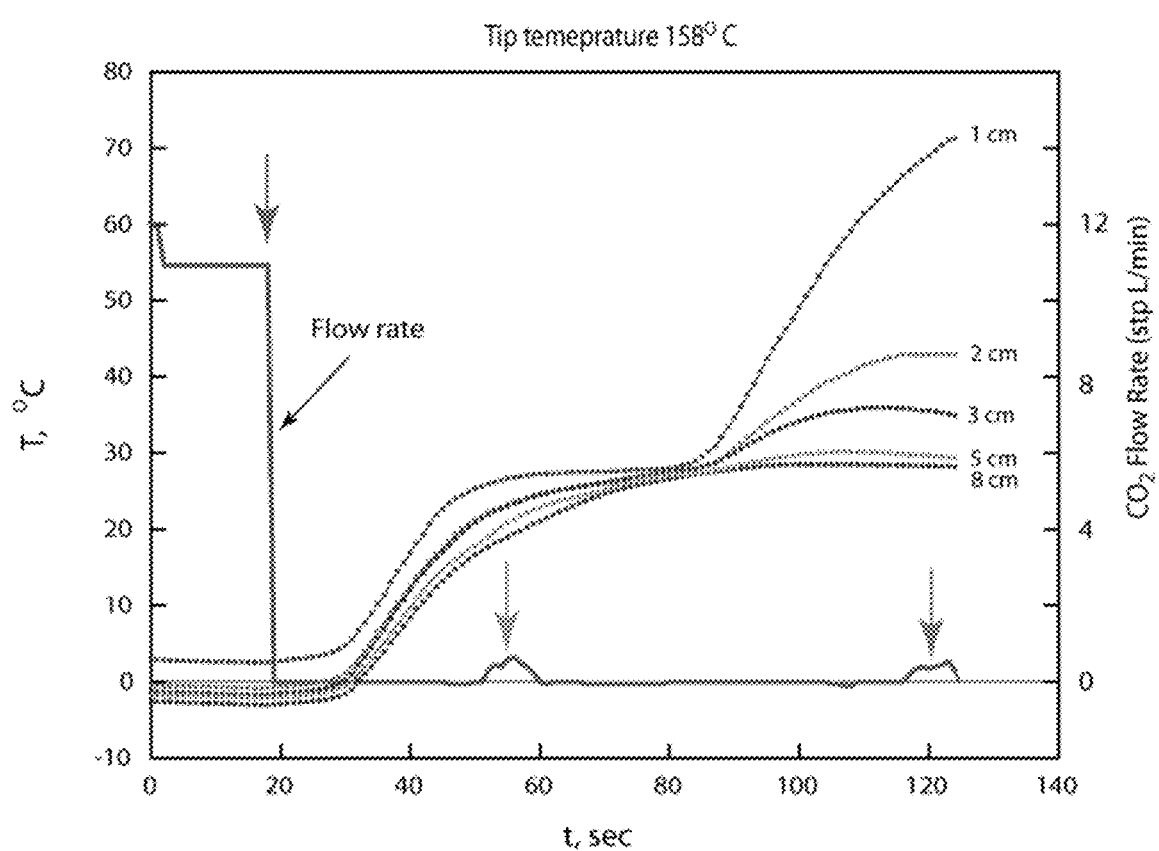
FIG. 26 shows that pulses of $CO_2$ as small as 1 stp L/min for 10 s counterbalance the thermally conductive heating from the tip of the antenna.

Follow-up tests using the same setup and heater was also performed to evaluate the lower-limit of cooling power required. In this study, an initial flow of 10 stp L/min was shown to decrease temperatures to ~0° C. That flow was then removed and pulses of $CO_2$ at 1 stp L/min were injected for approximately 10 s when the shaft temperature rose more than 30° C. Despite rapid rises in temperature without cooling, only small pulses of $CO_2$ were required to eliminate temperature rise and keep the system at ambient temperature (FIG. 26). These results suggest, for example, that small amounts of $CO_2$ may be able to be used to keep the antenna below ISO 60601-1 standards during the procedure. A temperature feedback/monitoring system could be employed to minimize the use of $CO_2$ during the procedure. Near-critical $CO_2$ is a feasible and effective alternative to liquid cooling inside microwave ablation antennas. The increased heat capacity of NC—$CO_2$ ensures that only small volumes of fluid are required to cool the ablation antenna to safe levels. It was shown that modest flow rates ~10 stp L/min were sufficient to cool antennas generating as much as 50 W.

Example VII

This example assessed the feasibility of using small, periodic injections of iodinated contrast material over the course of the ablation with a new reconstruction technique to improve ablation zone visualization while reducing contrast material dose. The lack of a ubiquitous and effective intra-procedural imaging technique is a critical limitation to the field of thermal tumor ablation. Ultrasound imaging can be obscured by bubbles formed while heating, and contrast-enhanced CT is typically limited to one scan with a large injection of contrast material.

Female domestic swine were prepared and anesthetized. RF ablation was performed for 20 min using three internally-cooled, switched electrodes. During ablation, 15 ml iodinated contrast material (300 mg/ml) was delivered every 2 min and an abdominal CT collected at the pre-determined liver enhancement time following each injection (90 s). CT images were created using both conventional online reconstruction and offline reconstruction with HighlY-constrained backPRojection (HYPR). Conventional and HYPR-reconstructed images were compared for imaging contrast between the ablation zone and background liver and signal to noise ratios.

Figure 27:
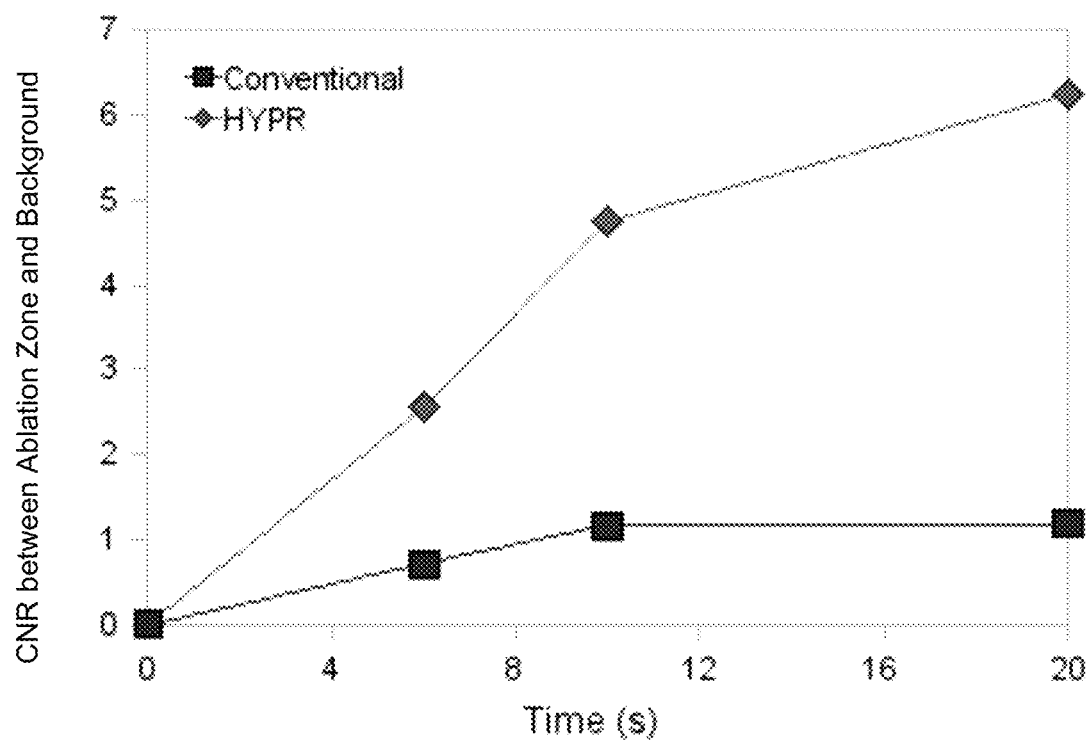
FIG. 27 shows conventional and HighlY-contstrained backPRojection (HYPR) image resolution as a function of time
Figure 28:
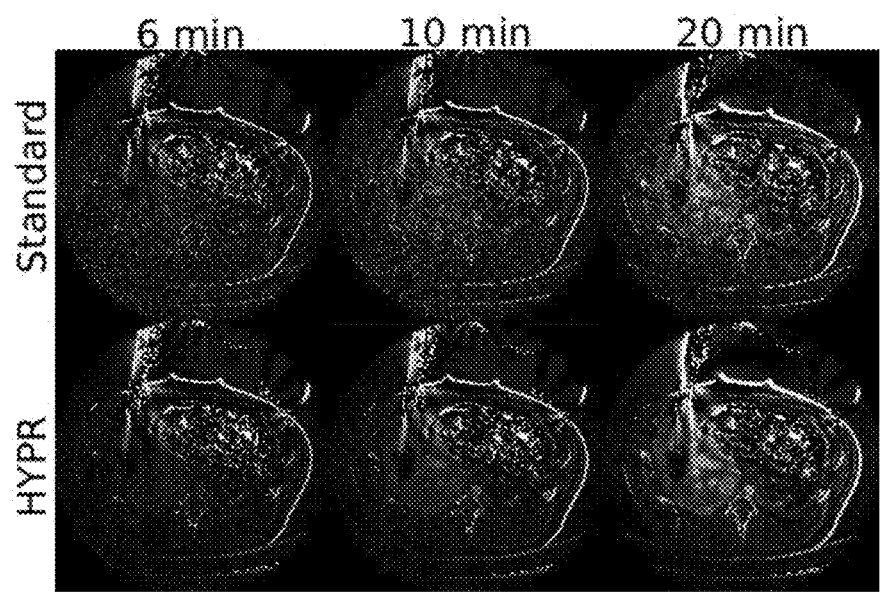
FIG. 28 shows standard and HighlY-contstrained back-PRojection (HYPR) tumor images over periods of time.

Ablation zone growth was able to be visualized with 2 min temporal resolution. The ablation zone became readily apparent in 2-6 min with a cumulative contrast dose of 15-45 ml. Image quality improved with cumulative contrast dose. SNR in HYPR-reconstructed images was ~3-4× better than standard reconstructions and HYPR improved signal contrast between the ablation zone and background liver by up to 6× (FIGS. 27 and 28).

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating a peripheral lung tissue in a subject, comprising
    steering a microwave energy delivery device through the subject's lung and positioning a microwave energy delivery device at a target peripheral lung tissue, and ablating the target peripheral lung tissue with energy from the microwave energy delivery device,
    wherein the steering is through the subject's mouth, through the subject's trachea, and through the subject's lung,
    wherein the microwave energy delivery device comprises an inner conductor and an outer conductor, the inner conductor comprises a proximal end and a distal end, the outer conductor comprises a proximal end and a distal end, the microwave energy delivery device is formed such that coolant can circulate via the proximal end of the inner conductor, through a cooling channel of the inner conductor, out from a distal end of the inner conductor, via a region between the distal end of the inner conductor and the distal end of the outer conductor, through space which is formed in the outer conductor, and extends from the distal side of the outer conductor to a proximal side of the outer conductor, and via a region between the proximal end of the inner conductor and the proximal end of the outer conductor.

2. The method of claim 1, wherein said microwave delivery device is inserted through the bronchial tree of the subject.

3. The method of claim 1, further comprising a handle for manipulation of the microwave energy delivery device.

4. The method of claim 1, further comprising a processor capable of operating the microwave energy delivery device.

5. The method of claim 1, wherein the steering comprises
    advancing a hollow primary catheter having a hollow channel catheter therein through the subject's mouth, through the subject's trachea, and through the subject's lung until further advance is constrained by the diameter of the hollow primary catheter, wherein the hollow channel catheter has therein a steerable navigation catheter,
    advancing the hollow channel catheter having the steerable navigation catheter therein beyond the distal end of the hollow primary catheter and extending the hollow channel catheter having the steerable navigation catheter therein through the subject's lung and to the target peripheral lung tissue, withdrawing the steerable navigation catheter from the hollow channel catheter, inserting the microwave energy delivery device through the hollow channel catheter such that it is positioned at the target peripheral lung tissue region.

6. The method of claim 5, wherein advancing the hollow channel catheter having the steerable navigation catheter therein beyond the distal end of the hollow primary catheter and extending the hollow channel catheter having the steerable navigation catheter therein through the subject's lung comprises extending the hollow channel catheter having the steerable navigation catheter therein through one or more of primary bronchial tissue, secondary bronchial tissue, tertiary bronchial tissue, and bronchiole tissue.

7. The method of claim 5, wherein the steerable navigation catheter controls the advancing.

8. The method of claim 1, wherein the microwave energy delivery device comprises a braided material.

9. The method of claim 1, wherein ablating the target peripheral lung tissue region with energy from the microwave energy delivery device is controlled with a processor.

10. The method of claim 1, wherein the microwave energy delivery device is in electrical communication with an energy power supply.

11. The method of claim 1, wherein the target peripheral lung tissue region comprises lung nodule tissue.

12. The method of claim 1, wherein the target peripheral lung tissue region comprises lung tumor tissue.

13. The method of claim 1, wherein the target peripheral lung tissue region comprises lung lesion tissue.

14. The method of claim 1, wherein the target peripheral lung tissue region comprises cancerous tissue.

15. The method of claim 1, wherein the microwave energy delivery device is configured to detect an undesired rise in temperature within the microwave energy delivery device and automatically or manually reduce such an undesired temperature rise through flowing of coolant through the one or more coolant channels.

\* \* \* \* \*